US012770229B2

(12) United States Patent
Chiang et al.

(10) Patent No.: US 12,770,229 B2
(45) Date of Patent: Oct. 20, 2026

(54) HYPERSPECTRAL IMAGING SYSTEM WITH HYBRID UNMIXING

(71) Applicant: UNIVERSITY OF SOUTHERN CALIFORNIA, Los Angeles, CA (US)

(72) Inventors: Hsiao-Ju Chiang, Los Angeles, CA (US); Eun Sang Koo, Los Angeles, CA (US); Scott E. Fraser, Los Angeles, CA (US); Francesco Cutrale, Los Angeles, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 347 days.

(21) Appl. No.: 18/694,889

(22) PCT Filed: Sep. 22, 2022

(86) PCT No.: PCT/US2022/076883
§ 371 (c)(1),
(2) Date: Mar. 22, 2024

(87) PCT Pub. No.: WO2024/039406
PCT Pub. Date: Feb. 22, 2024

(65) Prior Publication Data

US 2024/0412338 A1 Dec. 12, 2024

Related U.S. Application Data

(60) Provisional application No. 63/247,688, filed on Sep. 23, 2021.

(51) Int. Cl.
*G06T 5/70* (2024.01)
*A61B 5/00* (2006.01)
(Continued)

(52) U.S. Cl.
CPC .............. *G06T 5/70* (2024.01); *A61B 5/0075* (2013.01); *G01J 3/2823* (2013.01); *G06T 5/10* (2013.01);
(Continued)

(58) Field of Classification Search
None
See application file for complete search history.

(56) References Cited

U.S. PATENT DOCUMENTS

2012/0082362 A1* 4/2012 Diem ...................... G16Z 99/00 382/133
2012/0276578 A1* 11/2012 Stringari ............ G01N 21/6486 435/288.7

(Continued)

FOREIGN PATENT DOCUMENTS

WO WO-2021183967 A1 * 9/2021 ........... A61B 5/0075

OTHER PUBLICATIONS

Amat, et al., "Fast, Accurate Reconstruction of Cell Lineages from Large-scale Fluorescence Microscopy Data", Nature Methods, vol. 11, No. 9, pp. 951-964, Sep. 2014.

(Continued)

*Primary Examiner* — Mark R Milia
(74) *Attorney, Agent, or Firm* — Meunier Carlin & Curfman LLC

(57) ABSTRACT

Hybrid unmixing technique (HyU) of this disclosure may provide enhanced imaging of multiplexed fluorescence labels, enabling longitudinal imaging of multiple fluorescent signals with reduced illumination intensities. This disclosure generally relates to imaging systems. This disclosure relates to hyperspectral imaging systems. This disclosure further relates to hyperspectral imaging systems that generate an unmixed color image of a target. This disclosure further relates to a hyperspectral imaging system that is configured (Continued)

to use a hybrid unmixing technique to provide enhanced imaging of a target. This disclosure further relates to a hyperspectral imaging system that is configured to use a hybrid unmixing technique to provide enhanced imaging of multiplexed fluorescence labels, enabling longitudinal imaging of multiple fluorescent signals with reduced illumination intensities. This disclosure further relates to hyperspectral imaging systems that are used in diagnosing a health condition.

20 Claims, 43 Drawing Sheets

(51) Int. Cl.

| | |
|---|---|
| ***G01J 3/28*** | (2006.01) |
| ***G06T 5/10*** | (2006.01) |
| ***G06V 10/58*** | (2022.01) |
| ***G06V 20/69*** | (2022.01) |

(52) U.S. Cl.

CPC ............ *G06V 10/58* (2022.01); *G06V 20/695* (2022.01); *G01J 2003/2826* (2013.01); *G06T 2207/10036* (2013.01); *G06T 2207/10064* (2013.01)

(56) References Cited

U.S. PATENT DOCUMENTS

| | | | | |
|---|---|---|---|---|
| 2016/0238532 | A1* | 8/2016 | Freudiger | G02B 21/16 |
| 2019/0287222 | A1* | 9/2019 | Cutrale | G02B 21/08 |
| 2021/0199582 | A1* | 7/2021 | Fereidouni | G01N 21/6428 |
| 2022/0108430 | A1* | 4/2022 | Shi | G06T 5/73 |

OTHER PUBLICATIONS

Andrews, et al., "Spectral Phasor Analysis of Pyronin Y Labeled RNA Microenvironments in Living Cells", Biomedical Optics Express, vol. 4, No. 1, pp. 171-177, Jan. 1, 2013.
Bird, et al., "Metabolic Mapping of MCF10A Human Breast Cells via Multiphoton Fluorescence Lifetime Imaging of the Coenzyme NADH", Cancer Research, vol. 65, No. 19, 9 pages, Oct. 1, 2005.
Chen, et al., "Lattice Light Sheet Microscopy: Imaging Molecules to Embryos at High Spatiotemporal Resolution", Science, vol. 346, No. 6208, 28 pages, Oct. 24, 2014.
Costa, et al., "Asymmetric Division Coordinates Collective Cell Migration in Angiogenesis", Nature Cell Biology, vol. 18, No. 12, pp. 1292-1301, Dec. 2016.
Cutrale, et al., "Hyperspectral Phasor Analysis Enables Multi-Plexed 5D in Vivo Imaging", Ntaure Methods, vol. 14, pp. 149-152, 2017.
Dalal, et al., "Determination of Particle No. and Brightness Using a Laser Scanning Confocal Microscope Operating in the Analog Mode", Microscopy Research and Technique, vol. 71, pp. 69-81, 2008.
Datta, et al., "Interactions with Stromal Cells Promote a More Oxidized Cancer Cell Redox State in Pancreatic Tumors", Science Advances, vol. 8, 12 pages, Jan. 21, 2022.
Denk, et al., "Two-photon Laser Scanning Fluorescence Microscopy", Science, vol. 248, No. 4951, pp. 73-76, Apr. 6, 1990.
Depasquale, Joseph A, "Actin Microridges", The Anatomical Record, vol. 301, pp. 2037-2050, 2018.
Digman, et al., "Mapping the Number of Molecules and Brightness in the Laser Scanning Microscope", Biophysical Journal, vol. 94, pp. 2320-2332, Mar. 2008.
Digman, et al., "The Phasor Approach to Fluorescence Lifetime Imaging Analysis", Biophysical Journal: Biophysical Letters, 3 pages, 2008.
Dobigeon, et al., "Linear and Nonlinear Unmixing in Hyperspectral Imaging", Data Handling in Science and Technology, vol. 30, pp. 185-224, 2016.
Entenberg, et al., "Setup and Use of a Two-laser Multiphoton Microscope for Multichannel Intravital Fluorescence Imaging", Nature Protocols, vol. 6, No. 10, 22 pages, Sep. 8, 2011.
Fereidouni, et al., "Phasor Analysis of Multiphoton Spectral Images Distinguishes Autofluorescence Components of in Vivo Human Skin", Journal of Biophotonics, vol. 7, No. 8, pp. 589-596, 2014.
Fereidouni, et al., "Spectral Phasor Analysis Allows Rapid and Reliable Unmixing of Fluorescence Microscopy Spectral Images.", Optics Express, vol. 20, No. 12, pp. 12729-12741, Jun. 4, 2012.
Fevotte, et al., "Nonlinear Hyperspectral Unmixing with Robust Nonnegative Matrix Factorization", IEEE Transactions on Image Processing, vol. 24, No. 12, pp. 4810-4819, Dec. 2015.
Garini, et al., "Spectral Imaging: Principles and Applications", International Society for Analytical Cytology, vol. 69A, pp. 735-747, 2006.
Hass, et al., "Single-Cell Biochemical Multiplexing by Multidimensional Phasor Demixing and Spectral Fluorescence Lifetime Imaging Microscopy", Frontiers in Physics, vol. 9, 14 pages, May 2021.
Hedde, et al., "Phasor-based Hyperspectral Snapshot Microscopy Allows Fast Imaging of Live, Three-dimensional Tissues for Biomedical Applications", Communications Biology, vol. 4, No. 721, 11 pages, 2021.
Heslop, et al., "Using Non-negative Matrix Factorization in the "unmixing" of Diffuse Reflectance Spectra", Marine Geology, vol. 241, pp. 63-78, Jun. 25, 2007.
Huang, et al., "Video-rate Nanoscopy Enabled by sCOMS Camera-specific Single-molecule Localization Algorithms", Nature Methods, vol. 10, No. 7, pp. 653-658, Jul. 2013.
Islam, et al., "pH Dependence of the FLuorescence Lifetime of FAD in Solution and in Cells", International Journal of Molecular Sciences, vol. 14, pp. 1952-1963, Jan. 18, 2013.
Isogai, et al., "Angiogenic Network Formation in the Developing Vertebrate Trunk", Development, vol. 130, No. 21, pp. 5281-5290, 2003.
Jahr, et al., "Hyperspectral Light Sheet Microscopy", Nature Communications, vol. 6, pp. 1-7, 2015.
Jeong, et al., "Time-resolved Fluorescence Microscopy with Phasor Analysis for Visualizing Multicomponent Topical Drug Distribution Within Human Skin", Scientific Reports, vol. 10, No. 5360, 12 pages, 2020.
Keshava, et al., "Spectral Unmixing", IEEE Signal Processing Magazine, pp. 44-57, Jan. 2002.
Kredel, et al., "mRuby, a Bright Monomeric Red Fluorescent Protein for Labeling of Subcellular Structures", PLOS ONE, vol. 4, Issue 2, 7 pages, Feb. 2009.
Lakowicz, et al., "Fluorescence Lifetime Imaging of Free and Protein-bound NADH", Proceedings of the National Academy of Sciences of the United States of America, vol. 89, pp. 1271-1275, Feb. 1992.
Lanzano, et al., "Encoding and Decoding Spatio-temporal Information for Super-resolution Microscopy", Nature Communications, vol. 6, No. 6701, 9 pages, Apr. 2, 2015.
Lichtman, et al., "Fluorescence Microscopy", Nature Methods, vol. 2, No. 12, pp. 910-919, Dec. 2005.
Ma, et al., "Label-free Assessment of Preimplantation Embryo Quality by the Fluorescence Lifetime Imaging Microscopy (Flim)-phasor Approach", Scientific Reports, vol. 9, No. 13206, 13 pages, Sep. 12, 2019.
Malacrida, et al., "The Phasor Plot: A Universal Circle to Advance Fluorescence Lifetime Analysis and Interpretation", Annual Review of Biophysics, vol. 50, 22 pages, 2021.
Okuda, et al., "Endothelial Cell Dynamics in Vascular Development: Insights From Live-Imaging in Zebrafish", Frontiers in Physiology, vol. 11, 16 pages, Jul. 2020.
Parichy, et al., "An Orthologue of the Kit-related Gene Fms is Required for Development of Neural Crest-derived Xanthophores and a Subpopulation of Adult Melanocytes in the Zebrafish, *Danio rerio*", Development, vol. 127, pp. 3031-3044, 2000.

(56) References Cited

OTHER PUBLICATIONS

Parslow, et al., "Sample Drift Correction Following 4D Confocal Time-lapse Imaging", Journal of Visualized Experimens, vol. 86, April, 4 pages, 2014.
Rakhymzhan, et al., "Synergistic Strategy for Multicolor Two-photon Microscopy: Application to the Analysis of Germinal Center Reactions in Vivo", Scientific Reports, vol. 7, No. 7101,16 pages, Aug. 2, 2017.
Ranjit, et al., "Fit-free Analysis of Fluorescence Lifetime Imaging Data Using the Phasor Approach", Nature Protocols, 35 pages, 2018.
Ranjit, et al., "Multicomponent Analysis of Phasor Plot in a Single Pixel to Calculate Changes of Metabolic Trajectory in Biological Systems", The Journal of Physical Chemistry A, vol. 123, Oct. 22, 2019.
Sakaguchi, et al., "Bright Multicolor Labeling of Neuronal Circuits with Fluorescent Proteins and Chemical Tags", ELife, vol. 7, 28 pages, 2018.
Sawano Sakaue, et al., "Visualizing Spatiotemporal Dynamics of Multicellular Cell-Cycle Progression", Cell, vol. 132, pp. 487-498, Feb. 8, 2008.
Schindelin, et al., "Fiji—An Open Source Platform for Biological Image Analysis", Nature Methods, vol. 9, No. 7, 15 pages, 2019.
Scipioni, et al., "Phasor S-Flim: A New Paradigm for Fast and Robust Spectral Fluorescence Lifetime Imaging", Nature Methods, vol. 18, No. 5, pp. 542-550, May 2021.
Sharick, et al., "Protein-bound NAD(P)H Lifetime is Sensitive to Multiple Fates of Glucose Carbon", Scientific Reports, vol. 8, No. 5456, 13 pages, Apr. 3, 2018.
Shi, et al., "Pre-processing Visualization of Hyperspectral FLuorescent Data with Spectrally Encoded Enhanced Representations", Nature Communications, vol. 11, No. 726, 15 pages, 2020.
Shimozono, et al., "Visualization of an Endogenous Retinoic Acid Gradient Across Embryonic Development", Nature, vol. 496, pp. 363-366, 2013.
Sinclair, et al., "Hyperspectral Confocal Microscope", Applied Optics, vol. 45, No. 24, pp. 6283-6291, Aug. 20, 2006.
Skala, et al., "In Vivo Multiphoton Microscopy of NADH and FAD Redox States, Fluorescence Lifetimes, and Cellular Morphology in Precancerous Epithelia", PNAS, vol. 104, No. 49, pp. 19494-19499, Dec. 4, 2007.
Strauss, et al., "Up to 100-fold Speed-up and Multiplexing in Optimized DNA-Paint", Nature Methods, vol. 17, No. 8, pp. 789-791, Aug. 1, 2020.
Stringari, et al., "Metabolic Trajectory of Cellular Differentiation in Small Intestine by Phasor Fluorescence Lifetime Microscopy of NADH", Scientific Reports, vol. 2, No. 568, 9 pages, Aug. 10, 2012.
Stringari, et al., "Phasor Approach to FLuorescence Lifetime Microscopy Distinguishes Different Metabolic States of Germ Cells in a Live Tissue", PNAS, vol. 108, No. 33, pp. 13582-13587, Aug. 16, 2011.
Trinh, et al., "A Versatile Gene Trap to Visualize and Interrogate the Function of the Vertebrate Proteome", Genes & Development, vol. 25, pp. 2306-2320, 2011.
Truong, et al., "Deep and Fast Live Imaging with Two-photon Scanned Light-sheet Microscopy", Nature Methods, vol. 8, No. 9, 6 pages, Sep. 2011.
Tsurui, et al., "Seven-color Fluorescence Imaging of Tissue Samples Based on Fourier Spectroscopy and Singular Value Decomposition", The Journal of Histochemistry & Cytochemistry, vol. 48, No. 5, pp. 653-662, 2000.
Ueno, et al., "Fluorescent Probes for Sensing and Imaging", Nature Methods, vol. 8, pp. 642-645, 2011.
Valm, et al., "Applying Systems-level Spectral Imaging and Analysis to Reveal the Organelle Interactome", Nature, vol. 546, No. 7656, pp. 162-167, Jun. 1, 2017.
Wade, et al., "124-Color Super-resolution Imaging by Engineering DNA-Paint Blinking Kinetics", Nano Letters, vol. 19, pp. 2641-2646, 2019.
Wagnieres, et al., "In Vivo Fluorescence Spectroscopy and Imaging for Oncological Applications", Photochemistry and Photobiology, vol. 68, No. 5, pp. 603-632, 1998.
Wei, et al., "An Overview on Linear Unmixing of Hyperspectral Data", Mathematical Problems in Engineering, Article ID 3735403, 12 pages, 2020.
Yao, et al., "Multiplexed Bioluminescence Microscopy via Phasor Analysis", Nature Methods, vol. 19, No. 7. pp. 893-898, 2022.
Zimmermann, Timo, "Spectral Imaging and Linear Unmixing in Light Microscopy", Advances in Biochemical Engineering/Biotechnology, vol. 95, pp. 245-265, 2005.
Zimmermann, et al., "Spectral Imaging and its Applications in Live Cell Microscopy", FEBS Letters, vol. 546, pp. 87-92, 2003.
Zipfel, et al., "Live Tissue Intrinsic Emission Microscopy Using Multiphoton-excited Native Fluorescence and Second Harmonic Generation", Department of Applied and Engineering Physics, vol. 100, No. 12, pp. 7075-7080, Jun. 10, 2003.
Zeiss, "Introduction to Spectral Imaging and Linear Unmixing", Zeiss Microscopy Online Campus, 13 pages, 2010.
Neel-Dey, "Robust-NMF", Online Available on at URL-[https://github.com/neel-dey/robust-nmf], 4 pages, retreived on Jan. 3, 2025.
Dickinson, et al., "Multi-Spectral Imaging and Linear Unmixing Add a Whole New Dimension to Laser Scanning Fluorescence Microscopy", BioTechniques, vol. 31, No. 6, 7 pages, 2001.
Pysptools, "Abundance Maps", Online Available on at URL—[https://pysptools.sourceforge.io/abundance_maps.html], 6 pages, retreived on Jan. 3, 2025.

* cited by examiner

HYPERSPECTRAL IMAGING SYSTEM WITH HYBRID UNMIXING

CROSS-REFERENCE TO RELATED APPLICATION

This application is a U.S. National Phase Application of International Patent Application Number PCT/US2022/076883 filed on Sep. 22, 2022, which, is based upon and claims priority to U.S. provisional patent application 63/247,688, entitled "A Hyperspectral Imaging System with Hybrid Unmixing," filed Sep. 23, 2021. The entire content of the aforementioned patent applications are incorporated herein by reference.

STATEMENT REGARDING FEDERALLY SPONSORED RESEARCH

This invention was made with government support under Grant No. DGE-1842487, which was awarded by the National Science Foundation Graduate Research Fellowship, and under Grant No. PR150666, which was awarded by the Department of Defense. The government has certain rights in the invention.

TECHNICAL FIELD

This disclosure generally relates to imaging systems. This disclosure relates to hyperspectral imaging systems. This disclosure further relates to hyperspectral imaging systems that generate an unmixed color image of a target. This disclosure further relates to a hyperspectral imaging system that is configured to use a hybrid unmixing technique to provide enhanced imaging of a target. This disclosure further relates to a hyperspectral imaging system that is configured to use a hybrid unmixing technique to provide enhanced imaging of multiplexed fluorescence labels, enabling longitudinal imaging of multiple fluorescent signals with reduced illumination intensities. This disclosure further relates to hyperspectral imaging systems that are used in diagnosing a health condition.

BACKGROUND

The expanded application of fluorescence imaging in biomedical and biological research towards more complex systems and geometries may require tools that can analyze a multitude of components at widely varying time- and length-scales. A major challenge in such complex imaging experiments may be to cleanly separate multiple fluorescent labels with overlapping spectra from one another and background autofluorescence, without perturbing the sample with high levels of light. Thus, there is a requirement for efficient and robust analysis tools capable of quantitatively separating these signals.

In recent years, high-content imaging approaches have been refined for decoding the complex and dynamical orchestration of biological processes. Fluorescence, with its high contrast, high specificity and multiple parameters, has become the reference technique for imaging. Continuous improvements in fluorescent microscopes and the ever-expanding palette of genetically-encoded and synthesized fluorophores have enabled the labeling and observation of a large number of molecular species. Such fluorescence techniques may offer the potential of using multiplexed imaging to follow multiple labels simultaneously in the same specimen, but these techniques have fallen short of their fully imagined capabilities. Standard fluorescence microscopes may collect multiple images sequentially, employing different excitation and detection bandpass filters for each label.

Recently developed fluorescence techniques may allow for massive multiplexing by utilizing sequential labeling of fixed samples but are not suitable for in vivo imaging. These approaches may be ill-suited to separating overlapping fluorescence emission signals, and the narrow bandpass optical filters used to increase selectivity, decrease the photon efficiency of the imaging. (FIGS. 7-8) These limitations have restricted the number of imaged fluorophores per sample (usually up to 4) and risk exposing the specimen to damaging levels of exciting light. Such limitations have been a significant obstacle for dynamic imaging, preventing in vivo and intravital imaging from reaching its full potential with a broader impact on research/application, from developmental biology, cancer research and immunology to neuroimaging.

Hyperspectral Fluorescent Imaging (HFI) potentially overcomes the limitations of overlapping emissions by expanding signal detection into the spectral domain. HFI captures a spectral profile from each (image) pixel, resulting in a hyperspectral cube (x,y, wavelength) of data, that can be processed to deduce the labels present in that pixel. Linear unmixing (LU) has been widely utilized to analyze HFI data, and has performed well with bright samples emitting strong signals from fully-characterized, extrinsic fluorophores such as fluorescent proteins and dyes. However, in vivo fluorescence microscopy is almost always limited in the number of photons collected per pixel (due to the expression levels, the bio-physical fluorescent properties, and the sensitivity of the detection system), which reduces the quality of the spectra acquired.

A further challenge which affects the quality of spectra is the presence of multiple forms of noise in the imaging of the sample. Two examples of instrumental noise may be photon noise and read noise.

The photon noise, also known as Poisson noise, may be an inherent property related to the statistical variation of photons emission from a source and of detection. Poisson noise may be inevitable when imaging fluorescent dyes and is more pronounced in the low-photon regime. Such noise may pose challenges, especially in live and time lapse imaging, where the power of the exciting laser is reduced to avoid photo-damage to the sample, decreasing the amount of fluorescent signal.

The read noise may arise from voltage fluctuations in microscopes operating in analog mode during the conversion from photon to digital levels intensity and commonly affects fluorescence imaging acquisition.

Most biological samples used for in vivo microscopy are labeled using extrinsic signals from fluorescent proteins or probes but often include intrinsic signals (autofluorescence). Autofluorescence may contribute to photons that are undesired, difficult to identify and to account for in LU.

The cumulative presence of noise may inevitably lead to a degradation of acquired spectra during imaging. As a result, the spectral separation by LU may often be compromised, and the Signal to Noise ratio (SNR) of the final unmixing is often reduced by the weakest of the signals detected.

Increasing the amount of laser excitation may partially overcome these challenges, but the higher energy deposition in the sample may cause photo-bleaching and photo-damage, affecting both the integrity of the live sample and the duration of the observation.

Also, traditional unmixing strategies such as LU may computationally be demanding, requiring long analyses times and often slowing the interrogation.

Combined, above potential compromises and shortcomings have reduced both the overall multiplexing capability and the adoption of HFI multiplexing technologies.

RELATED ART REFERENCES

The following publications are related art for the background of this disclosure. One digit or two-digit numbers in the box brackets before each reference correspond to the numbers in the box brackets used in the other parts of this disclosure.

[1] Valm, A. M. et al. Applying systems-level spectral imaging and analysis to reveal the organelle interactome. Nature 546, 162-167 (2017).
[2] Tsurui, H. et al. Seven-color fluorescence imaging of tissue samples based on fourier spectroscopy and singular value decomposition. Journal of Histochemistry and Cytochemistry 48, 653-662 (2000).
[3] Amat, F. et al. Fast, accurate reconstruction of cell lineages from large-scale fluorescence microscopy data. Nature Methods 11, 951-958 (2014).
[4] Ueno, T. & Nagano, T. Fluorescent probes for sensing and imaging. Nature Methods vol. 8 642-645 Preprint at https://doi.org/10.1038/nmeth.1663 (2011).
[5] Lichtman, J. W. & Conchello, J. A. Fluorescence microscopy. Nature Methods vol. 2 910-919 Preprint at https://doi.org/10.1038/nmeth817 (2005).
[6] Sinclair, M. B., Haaland, D. M., Timlin, J. A. & Jones, H. D. T. Hyperspectral confocal microscope. 45, 6283-6291 (2006).
[7] Jahr, W., Schmid, B., Schmied, C., Fahrbach, F. O. & Huisken, J. Hyperspectral light sheet microscopy. Nature Communications 6, 1-7 (2015).
[8] Truong, T. V, Supatto, W., Koos, D. S., Choi, J. M. & Fraser, S. E. Deep and fast live imaging with two-photon scanned light-sheet microscopy. 8, (2011).
[9] Chen, B. C. et al. Lattice light-sheet microscopy: Imaging molecules to embryos at high spatiotemporal resolution. Science (1979) 346, (2014).
[10] Kredel, S. et al. mRuby, a bright monomeric red fluorescent protein for labeling of subcellular structures. PLoS ONE 4, 1-7 (2009).
[11] Sakaue-Sawano, A. et al. Visualizing Spatiotemporal Dynamics of Multicellular Cell-Cycle Progression. Cell 132, 487-498 (2008).
[12] Wade, O. K. et al. 124-Color Super-resolution Imaging by Engineering DNA-PAINT Blinking Kinetics. Nano Letters 19, 2641-2646 (2019).
[13] Strauss, S. & Jungmann, R. Up to 100-fold speed-up and multiplexing in optimized DNA-PAINT. Nature Methods 17, 789-791 (2020).
[14] Costa, G. et al. Asymmetric division coordinates collective cell migration in angiogenesis. Nature Cell Biology 18, 1292-1301 (2016).
[15] Entenberg, D. et al. Setup and use of a two-laser multiphoton microscope for multichannel intravital fluorescence imaging. Nature Protocols 6, (2011).
[16] Sakaguchi, R., Leiwe, M. N. & Imai, T. Bright multicolor labeling of neuronal circuits with fluorescent proteins and chemical tags. Elife 7, (2018).
[17] Zimmermann, T., Rietdorf, J. & Pepperkok, R. Spectral imaging and its applications in live cell microscopy. FEBS Letters 546, 87-92 (2003).
[18] Paddock, S. Multi-Spectral Imaging and Linear Unmixing Add a Whole New Dimension to. Biotechniques 31, 1272-1278 (2001).
[19] Zimmermann, T. Spectral imaging and linear unmixing in light microscopy. Advances in Biochemical Engineering/Biotechnology 95, 245-265 (2005).
[20] Garini, Y., Young, I. T. & McNamara, G. Spectral imaging: Principles and applications. Cytometry Part A vol. 69 Preprint at https://doi.org/10.1002/cyto.a.20311 (2006).
[21] Rakhymzhan, A. et al. Synergistic Strategy for Multicolor Two-photon Microscopy: Application to the Analysis of Germinal Center Reactions in Vivo. Scientific Reports 7, (2017).
[22] Bass, M. Handbook of Optics, vol 3. Geometric Optics, General Principles Spherical Surfaces, 2nd ed., Optical Society of America, New York (1995).
[23] Hamamatsu Photonics, K. K. P. T. H. PHOTOMULTIPLIER TUBES Basics and Applications FOURTH EDITION. (1994).
[24] Pawley, J. B. Confocal and two-photon microscopy: Foundations, applications and advances. Microscopy Research and Technique 59, (2002).
[25] Huang, F. et al. Video-rate nanoscopy using sCMOS camera-specific single-molecule localization algorithms. Nature Methods 10, (2013).
[26] Digman, M. A., Caiolfa, V. R., Zamai, M. & Gratton, E. The Phasor Approach to Fluorescence Lifetime Imaging Analysis. Biophysical Journal 94, L14-L16 (2008).
[27] Fereidouni, F., Bader, A. N., Colonna, A. & Gerritsen, H. C. Phasor analysis of multiphoton spectral images distinguishes autofluorescence components of in vivo human skin. Journal of Biophotonics 7, 589-596 (2014).
[28] Scipioni, L., Rossetta, A., Tedeschi, G. & Gratton, E. Phasor S-FLIM: a new paradigm for fast and robust spectral fluorescence lifetime imaging. Nature Methods 18, 542-550 (2021).
[29] Ranjit, S., Malacrida, L., Jameson, D. M. & Gratton, E. Fit-free analysis of fluorescence lifetime imaging data using the phasor approach. Nature Protocols 13, 1979-2004 (2018).
[30] Shi, W. et al. Pre-processing visualization of hyperspectral fluorescent data with Spectrally Encoded Enhanced Representations. Nature Communications 11, 1-15 (2020).
[31] Keshava, N. & Mustard, J. F. Spectral unmixing. IEEE Signal Processing Magazine 19, 44-57 (2002).
[32] Dobigeon, N., Altmann, Y., Brun, N. & Moussaoui, S. Linear and Nonlinear Unmixing in Hyperspectral Imaging. in Data Handling in Science and Technology vol. 30 (2016).
[33] Zeiss, C. & Online, M. Introduction to Spectral Imaging and Linear Unmixing. Imaging 1, 1-13 (2010).
[34] Hedde, P. N., Cinco, R., Malacrida, L., Kamaid, A. & Gratton, E. Phasor-based hyperspectral snapshot microscopy allows fast imaging of live, three-dimensional tissues for biomedical applications. Communications Biology 4, (2021).
[35] Cutrale, F. et al. Hyperspectral phasor analysis enables multi-plexed 5D in vivo imaging. Nature Publishing Group (2017) doi:10.1038/nmeth.4134.
[36] Stringari, C. et al. Metabolic trajectory of cellular differentiation in small intestine by Phasor Fluorescence Lifetime Microscopy of NADH. Scientific Reports 2, (2012).
[37] Ranjit, S., Datta, R., Dvornikov, A. & Gratton, E. Multicomponent Analysis of Phasor Plot in a Single Pixel to Calculate Changes of Metabolic Trajectory in Biological Systems. Journal of Physical Chemistry A 123, (2019).
[38] Jeong, S. et al. Time-resolved fluorescence microscopy with phasor analysis for visualizing multicomponent topical drug distribution within human skin. Scientific Reports 10, (2020).
[39] Haas, K. T., Fries, M. W., Venkitaraman, A. R. & Esposito, A. Single-Cell Biochemical Multiplexing by Multidimensional Phasor Demixing and Spectral Fluorescence Lifetime Imaging Microscopy. Frontiers in Physics 9, (2021).
[40] Lanzanó, L. et al. Encoding and decoding spatio-temporal information for super-resolution microscopy. Nature Communications 6, (2015).
[41] Yao, Z. et al. Multiplexed bioluminescence microscopy via phasor analysis. Nature Methods 2022 19:7 19, 893-898 (2022).
[42] Depasquale, J. A. Actin Microridges. Anat Rec (Hoboken) 301, 2037-2050 (2018).
[43] Okuda, K. S., Hogan, B. M., Cantelmo, A. R. & Hogan, B. M. Endothelial Cell Dynamics in Vascular Development: Insights From Live-Imaging in Zebrafish. 11, (2020).
[44] Isogai, S., Lawson, N. D., Torrealday, S., Horiguchi, M. & Weinstein, B. M. Angiogenic network formation in the developing vertebrate trunk. (2003) doi:10.1242/dev.00733.
[45] Denk, W., Strickler, J. H. & Webb, W. W. Two-photon laser scanning fluorescence microscopy. Science (1979) 248, (1990).
[46] Zipfel, W. R. et al. Live tissue intrinsic emission microscopy using multiphoton-excited native fluorescence and second harmonic generation. Proceedings of the National Academy of Sciences 100, 7075-7080 (2003).
[47] Datta, R. et al. Interactions with stromal cells promote a more oxidized cancer cell redox state in pancreatic tumors. Science Advances 8, (2022).
[48] Ma, N. et al. Label-free assessment of pre-implantation embryo quality by the Fluorescence Lifetime Imaging Microscopy (FLIM)-phasor approach. Scientific Reports 9, (2019).
[49] Zipfel, W. R. et al. Live tissue intrinsic emission microscopy using multiphoton-excited native fluorescence and second harmonic generation. Proc Natl Acad Sci USA 100, 7075-7080 (2003).
[50] Bird, D. K. et al. Metabolic mapping of MCF10A human breast cells via multiphoton fluorescence lifetime imaging of the coenzyme NADH. Cancer Research 65, (2005).
[51] Lakowicz, J. R., Szmacinski, H., Nowaczyk, K. & Johnson, M. L. Fluorescence lifetime imaging of free and protein-bound NADH. Proc Natl Acad Sci USA 89, (1992).
[52] Skala, M. C. et al. In vivo multiphoton microscopy of NADH and FAD redox states, fluorescence lifetimes, and cellular morphology in precancerous epithelia. Proc Natl Acad Sci USA 104, 19494-19499 (2007).
[53] Sharick, J. T. et al. Protein-bound NAD(P)H Lifetime is Sensitive to Multiple Fates of Glucose Carbon. Scientific Reports 8, (2018).
[54] Stringari, C. et al. Phasor approach to fluorescence lifetime microscopy distinguishes different metabolic states of germ cells in a live tissue. Proc Natl Acad Sci USA 108, (2011).
[55] Wagnieres, G. A., Star, W. M. & Wilson, B. C. Invited Review In Vivo Fluorescence Spectroscopy and Imaging for Oncological Applications. 68, 603-632 (1998).
[56] Févotte, C. & Dobigeon, N. Nonlinear hyperspectral unmixing with robust nonnegative matrix factorization. IEEE Transactions on Image Processing 24, (2015).
[57] Heslop, D., von Dobeneck, T. & Höcker, M. Using non-negative matrix factorization in the "unmixing" of diffuse reflectance spectra. Marine Geology 241, 63-78 (2007).
[58] Paddock, S. W. Confocal Microscopy, Methods and Protocols, Second Edition. Humana Press 1075, 388 (2014).
[59] M., W. The zebrafish book. (University of Oregon Press, 1994).
[60] Trinh, L. A. et al. A versatile gene trap to visualize and interrogate the function of the vertebrate proteome. Genes and Development 25, 2306-2320 (2011).
[61] Shi, W. et al. Pre-processing visualization of hyperspectral fluorescent data with Spectrally Encoded Enhanced Representations. Nature Communications 11, 1-15 (2020).
[62] Parichy, D. M., Ransom, D. G., Paw, B., Zon, L. I. & Johnson, S. L. An orthologue of the kit-related gene fms is required for development of neural crest-derived xanthophores and a subpopulation of adult melanocytes in the zebrafish, *Danio rerio*. Development (2000).
[63] Digman, M. A., Dalal, R., Horwitz, A. F. & Gratton, E. Mapping the number of molecules and brightness in the laser scanning microscope. Biophys J 94, 2320-2332 (2008).
[64] Dalal, R. B., Digman, M. A., Horwitz, A. F., Vetri, V. & Gratton, E. Determination of particle number and brightness using a laser scanning confocal microscope operating in the analog mode. Microsc Res Tech 71, 69-81 (2008).
[65] Wagnieres, G. A., Star, W. M. & Wilson, B. C. Invited Review In Vivo Fluorescence Spectroscopy and Imaging for Oncological Applications. 68, 603-632 (1998).
[66] Cutrale, F. et al. Hyperspectral phasor analysis enables multi-plexed 5D in vivo imaging. Nature Publishing Group (2017) doi:10.1038/nmeth.4134.
[67] Taylor, R. C. Experiments in physical chemistry (Shoemaker, David P.; Garland, Carl W.). Journal of Chemical Education 45, (1968).
[68] Févotte, C. & Dobigeon, N. Nonlinear hyperspectral unmixing with robust nonnegative matrix factorization. IEEE Transactions on Image Processing 24, (2015).
[69] Parslow, A., Cardona, A. & Bryson-Richardson, R. J. Sample drift correction following 4D confocal time-lapse Imaging. Journal of Visualized Experiments (2014) doi:10.3791/51086.
[70] Schindelin, J. et al. Fiji: An open-source platform for biological-image analysis. Nature Methods vol. 9 Preprint at https://doi.org/10.1038/nmeth.2019 (2012).
[71] Shimozono, S., Iimura, T., Kitaguchi, T., Higashijima, S. I. & Miyawaki, A. Visualization of an endogenous retinoic acid gradient across embryonic development. Nature 496, 363-366 (2013).
[72] Islam, M. S., Honma, M., Nakabayashi, T., Kinjo, M. & Ohta, N. pH dependence of the fluorescence lifetime of FAD in solution and in cells. International Journal of Molecular Sciences 14, (2013).
[73] Islam, M. S., Honma, M., Nakabayashi, T., Kinjo, M. & Ohta, N. pH dependence of the fluorescence lifetime of FAD in solution and in cells. International Journal of Molecular Sciences 14, (2013).

[74] Andrews, L. M., Jones, M. R., Digman, M. A. & Gratton, E. Spectral phasor analysis of Pyronin Y labeled RNA microenvironments in living cells. Biomedical Optics Express 4, (2013).
[75] Fereidouni, F., Bader, A. N. & Gerritsen, H. C. Spectral phasor analysis allows rapid and reliable unmixing of fluorescence microscopy spectral images. Optics Express 20, (2012).
[76] Cutrale, F. et al. Hyperspectral phasor analysis enables multiplexed 5D in vivo imaging. Nature Methods 14, (2017).
[77] Stringari, C. et al. Phasor approach to fluorescence lifetime microscopy distinguishes different metabolic states of germ cells in a live tissue. Proc Natl Acad Sci USA 108, 13582-7 (2011).
[78] Lanzanó, L. et al. Encoding and decoding spatio-temporal information for super-resolution microscopy. Nature Communications 6, (2015).
[79] Fereidouni, F., Bader, A. N. & Gerritsen, H. C. Spectral phasor analysis allows rapid and reliable unmixing of fluorescence microscopy spectral images. Opt Express 20, 12729-12741 (2012).
[80] Scipioni, L., Rossetta, A., Tedeschi, G. & Gratton, E. Phasor S-FLIM: a new paradigm for fast and robust spectral fluorescence lifetime imaging. Nature Methods 18, (2021).
[81] Malacrida, L., Ranjit, S., Jameson, D. M. & Gratton, E. The Phasor Plot: A Universal Circle to Advance Fluorescence Lifetime Analysis and Interpretation. Annual Review of Biophysics vol. 50 Preprint at https://doi.org/10.1146/annurev-biophys-062920-063631 (2021).
[82] Ranjit, S., Malacrida, L., Jameson, D. M. & Gratton, E. Fit-free analysis of fluorescence lifetime imaging data using the phasor approach. Nature Protocols 13, 1979-2004 (2018).
[83] Digman, M. A., Caiolfa, V. R., Zamai, M. & Gratton, E. The Phasor Approach to Fluorescence Lifetime Imaging Analysis. Biophysical Journal 94, L14-L16 (2008).

The entire content of each of the above publications is incorporated herein by reference.

SUMMARY

Examples described herein generally relate to imaging systems. The examples of this disclosure also relates to hyperspectral imaging systems. The examples further relate to hyperspectral imaging systems that generate an unmixed color image of a target. The examples further relate to a hyperspectral imaging system that is configured to use a hybrid unmixing technique to provide enhanced imaging of a target. The examples further relate to a hyperspectral imaging system that is configured to use a hybrid unmixing technique to provide enhanced imaging of multiplexed fluorescence labels, enabling longitudinal imaging of multiple fluorescent signals with reduced illumination intensities. The examples further relate to hyperspectral imaging systems that are used in diagnosing a health condition.

In this disclosure, the hyperspectral imaging system may include an image forming system. The image forming system may have a configuration to acquire a detected radiation of the target, wherein the detected radiation comprises at least two (target) waves, each target wave having a detected intensity and a different detected wavelength; to form a target image using the detected target radiation, wherein the target image comprises at least two (image) pixels, and wherein each image pixel corresponds to one physical point on the target; to form at least one (intensity) spectrum for each image pixel using the (detected) intensity and the (detected) wavelength of each target wave; to transform the intensity spectrum of each image pixel using a Fourier transform into a complex-valued function based on the intensity spectrum of each image pixel, wherein each complex-valued function has at least one real component and at least one imaginary component; to form one phasor point on a phasor plane for each image pixel by plotting value of the real component against value of the imaginary component, wherein the value of the real component is referred as the real value hereafter, and wherein the value of the imaginary component is referred as the imaginary value hereafter; and to form a (phasor) histogram comprising at least two phasor bins, wherein each (phasor) bin comprises at least one phasor point.

In this disclosure, the image forming system may have a (further) configuration to aggregate the detected spectra belonging to the image pixels of each phasor bin, to generate a representative intensity spectrum for each phasor bin; to unmix representative intensity spectra of the phasor bins by using an unmixing technique, thereby determining abundance of each spectral endmember of the detected radiation; to assign a color to a corresponding image pixel of the target by using the abundance of each spectral endmember in the representative intensity spectra and the detected intensity belonging to the image pixel; and to generate a representative image of the target representing the abundance of each spectral endmember.

In this disclosure, the intensity spectra aggregated in each phasor bin may have an essentially similar spectral shape or a substantially same spectral shape. Or, the intensity spectra aggregated in each phasor bin may have essentially similar spectral features or a substantially same spectral features. Such spectral features may include detected spectral intensities and/or detected wavelengths of each detected spectrum. For example, when each detected spectrum's detected intensities are normalized using a standard (e.g., a maximum detected intensity of said spectrum), the relative (normalized) detected intensities of all intensity spectra aggregated in the same bin may have an essentially similar spectral shape or a substantially same spectral shape. In one example of such configuration of the image forming system, each detected spectrum belonging to the image pixels of the same bin may have at least two detected intensities and a detected wavelength for each detected intensity. In another example of such configuration of the image forming system, the relative detected intensity values of each spectrum belonging to the same spectral bin may be substantially same to those of the other spectra aggregated in the same bin. Yet, in another example of such configuration of the image forming system, the said system may discretize the phasor plane to discrete phasor plane areas (wherein these phasor plane areas may have similar or same areal size and/or similar or same areal shape), and may treat the phasor points as phasor points that belong to essentially similar detected spectra or substantially same detected spectra. Yet, in another example of such configuration of the image forming system, the said system may form at least four phasor bins by discretizing a phasor plot along its real dimension and its imaginary dimension. For any such configurations, each phasor bin may have a phasor bin area on each phasor plot; wherein the phasor bin area may be 4/(total number of phasor bins), and wherein the total number of phasor bins may be a product of number of discretizations along real dimension of the phasor plot and number of discretizations along imaginary dimension of the phasor plot.

Summing or averaging these essentially similar or substantially same detected intensity spectra effectively averages the intensity spectra to generate a representative (or average) intensity spectrum for that phasor position. Summing or averaging these substantially similar intensity spectra may be achieved by any mathematical conventional or known manner. That is, any summing or averaging mathematical technique that may yield the representative intensity spectrum is within the scope of this disclosure.

In this disclosure, any (spectral) unmixing technique that may unmix a detected target radiation, intensity spectra, and/or representative intensity spectra is within the scope of this disclosure. The unmixing technique may be a linear unmixing technique. The unmixing technique may be a fully constrained least squares unmixing technique, a matrix inversion unmixing technique, non-negative matrix factorization unmixing technique, geometric unmixing technique, Bayesian unmixing technique, sparse unmixing technique, or any combination thereof.

The image forming system of this disclosure may have a further configuration that applies a denoising filter to reduce a Poisson noise and/or instrumental noise of the detected radiation. The image forming system may also have a further configuration that applies a denoising filter on the real component and/or the imaginary component of each complex-valued function at least once so as to produce a denoised real value and a denoised imaginary value for each image pixel. The denoising filter may be applied after the image forming system transforms the formed intensity spectrum belonging to each image pixel using the Fourier transform into the complex-valued function; and/or before the image forming system forms one phasor point on the phasor plane for each image pixel. The image forming system may also have a further configuration that may apply a denoising filter to the value of the real component and/or the value of the imaginary component after the image forming system forms one phasor point on the phasor plane for each image pixel. The denoised real value may be used as the real value for each image pixel and the denoised imaginary value for each image pixel may be used as the imaginary value to form one phasor point on the phasor plane for each image pixel.

The hyperspectral imaging system may further comprise an optics system. The optics system may include at least one optical component. The at least one optical component may include at least one optical detector. The at least one optical detector may have a configuration that may detect electromagnetic radiation absorbed, transmitted, refracted, reflected, and/or emitted from at least one physical point on the target, thereby forming the target radiation; wherein the target radiation comprises at least two target waves, each target wave having an intensity and a different wavelength. The at least one optical detector may have a further configuration that may detect the intensity and the wavelength of each target wave. The at least one optical detector may also have a further configuration that may transmit the detected target radiation, and each target wave's detected intensity and detected wavelength to the image forming system to be acquired. The image forming system may further comprise a control system, a hardware processor, a memory, and a display. The image forming system may have a further configuration that may display the representative image of the target on the image forming system's display.

The unmixing technique of this disclosure may be any unmixing technique. For example, the unmixing technique may be a linear unmixing technique. For example, the unmixing technique may be a fully constrained least squares unmixing technique, a matrix inversion unmixing technique, non-negative matrix factorization unmixing technique, geometric unmixing technique, Bayesian unmixing technique, sparse unmixing technique, or any combination thereof.

The image forming system of this disclosure may have a further configuration that applies a denoising filter to reduce a Poisson noise and/or instrumental noise of the detected radiation. The denoising filter may be any denoising filter applied at least once. Each applied denoising filter may be the same denoising filter or a different denoising filter. The denoising filter may be applied, for example, to an intensity of the target radiation, an intensity of an intensity spectrum, the real component and/or the imaginary component of each complex-valued function, an intensity of a representative intensity spectrum, and or a combination thereof. For example, the image forming system of this disclosure may have a configuration that applies a denoising filter on the real component and/or the imaginary component of each complex-valued function at least once so as to produce a denoised real value and a denoised imaginary value for each image pixel. For example, the image forming system of this disclosure may have a configuration that applies a denoising filter on both the real component and the imaginary component of each complex-valued function at least once so as to produce a denoised real value and a denoised imaginary value for each image pixel; wherein the denoising filter is applied: (1) after the image forming system transforms the formed intensity spectrum belonging to each image pixel using the Fourier transform into the complex-valued function; and/or (2) before the image forming system forms one phasor point on the phasor plane for each image pixel; and uses the denoised real value as the real value for each image pixel and the denoised imaginary value for each image pixel as the imaginary value to form one phasor point on the phasor plane for each image pixel. For example, the image forming system of this disclosure may have a configuration that applies a denoising filter to the value of the real component and/or the value of the imaginary component after the image forming system forms one phasor point on the phasor plane for each image pixel.

The image forming system of this disclosure may have a further configuration that may aggregate the detected spectra belonging to the image pixels of each phasor bin, wherein the detected spectra belonging to the image pixels of the same bin have substantially the same detected intensity and the detected wavelength.

The image forming system of this disclosure may have a further configuration that may use at least one harmonic of the Fourier transform to generate the representative image of the target. The at least one harmonic may be a first harmonic and/or a second harmonic. Such system may also use only one harmonic. The only one harmonic may be a first harmonic or a second harmonic. Such system may also use only a first harmonic and only a second harmonic.

In this disclosure, the at least one optical component may further include at least one illumination source to illuminate the target, wherein the illumination source generates an illumination source radiation that comprises at least one illumination wave. Such system may also further include at least one illumination source, wherein the illumination source generates an illumination source radiation that comprises at least two illumination waves, and wherein each illumination wave has a different wavelength.

In this disclosure, the image forming system may further include a control system, a hardware processor, a memory, and a display.

In this disclosure, the image forming system may have a further configuration that may display the representative image of the target on the image forming system's display.

In this disclosure, the image forming system may further include a control system, a hardware processor, a memory, and an information conveying system; wherein the information conveying system conveys the representative image of the target to a user in any manner. The information conveying system may convey the representative image of the target to a user as an image, a numerical value, a color, a sound, a mechanical movement, a signal, or a combination thereof.

In this disclosure, the at least one optical component may further include an optical lens, an optical filter, a dispersive optic system, or a combination thereof.

In this disclosure, the detected target radiation may be a fluorescence radiation.

Disclosed herein is a hyperspectral imaging system for generating a representative image of a target. The hyperspectral imaging system may comprise an image forming system. The image forming system may be configured to acquire a detected radiation of the target. The image forming system may be configured to form a target image using the detected target radiation, wherein the target image comprises at least two image pixels, and wherein each image pixel corresponds to one physical point on the target. The image forming system may be configured to form at least one intensity spectrum for each image pixel. The image forming system may be configured to transform the intensity spectrum of each image pixel based on the intensity spectrum of each image pixel. The image forming system may be configured to form one phasor point on a phasor plane for each image pixel. The image forming system may be configured to form a phasor histogram comprising at least two phasor bins, wherein each phasor bin comprises at least one phasor point. The image forming system may be configured to aggregate the detected spectra belonging to the image pixels of each phasor bin. The image forming system may be configured to generate a representative intensity spectrum for each phasor bin. The image forming system may be configured to unmix representative intensity spectra of the phasor bins using one or more unmixing techniques. The image forming system may be configured to determine an abundance of spectral endmembers in the representative intensity spectra. The image forming system may be configured to generate a representative intensity image of the target representing the abundance of the spectral endmembers.

Disclosed herein is a method for generating a representative image of a target. The method may comprise forming at least one intensity spectrum for image pixels of a target image, wherein the target image is based on a detected radiation. The method may comprise implementing a hyperspectral phasor system. The hyperspectral phasor system may be configured to form one phasor point on a phasor plane for each image pixel. The hyperspectral phasor system may be configured to form a phasor histogram comprising at least two phasor bins, wherein each phasor bin comprises at least one phasor point. The hyperspectral phasor system may be configured to aggregate the detected spectra of the image pixels of the at least two phasor bins. The hyperspectral phasor system may be configured to generate at least one representative intensity spectrum for the at least two phasor bins. The method may further comprise implementing an unmixing system. The unmixing system may be configured to unmix the at least one representative intensity spectrum of the at least two phasor bins using one or more unmixing techniques. The method may further comprise generating a representative intensity image of the target based on at least the representative intensity spectra and a detected intensity corresponding to the detected radiation.

Disclosed herein is a method for generating a representative image of a target. The method may comprise forming at least one intensity spectrum for image pixels of a target image, wherein the target image is based on a detected radiation. The method may comprise generating at least one representative intensity spectrum based on phasor points on a phasor plane corresponding to the image pixels. The method may comprise unmixing the at least one representative intensity spectrum using one or more linear unmixing techniques. The method may comprise generating a representative intensity image of the target based on at least the unmixed representative intensity spectrum.

Any combination of above features/configurations is within the scope of the instant disclosure.

These, as well as other components, steps, features, objects, benefits, and advantages, will now become clear from a review of the following detailed description of illustrative implementations, the accompanying drawings, and the claims.

BRIEF DESCRIPTION OF DRAWINGS

The drawings are illustrative implementations. They do not illustrate all implementations. Other implementations may be used in addition or instead. Details that may be apparent or unnecessary may be omitted to save space or for more effective illustration. Some implementations may be practiced with additional components or steps and/or without all of the components or steps that are illustrated. When the same numeral appears in different drawings, it refers to the same or like components or steps.

The colors disclosed in the following brief description of drawings and other parts of this disclosure refer to the color drawings and photos as originally filed with the U.S. provisional patent application 63/247,688, entitled "A Hyperspectral Imaging System with Hybrid Unmixing," filed Sep. 23, 2021. The entire content of the aforementioned provisional patent application is incorporated herein by reference.

DETAILED DESCRIPTION

Figure 1:
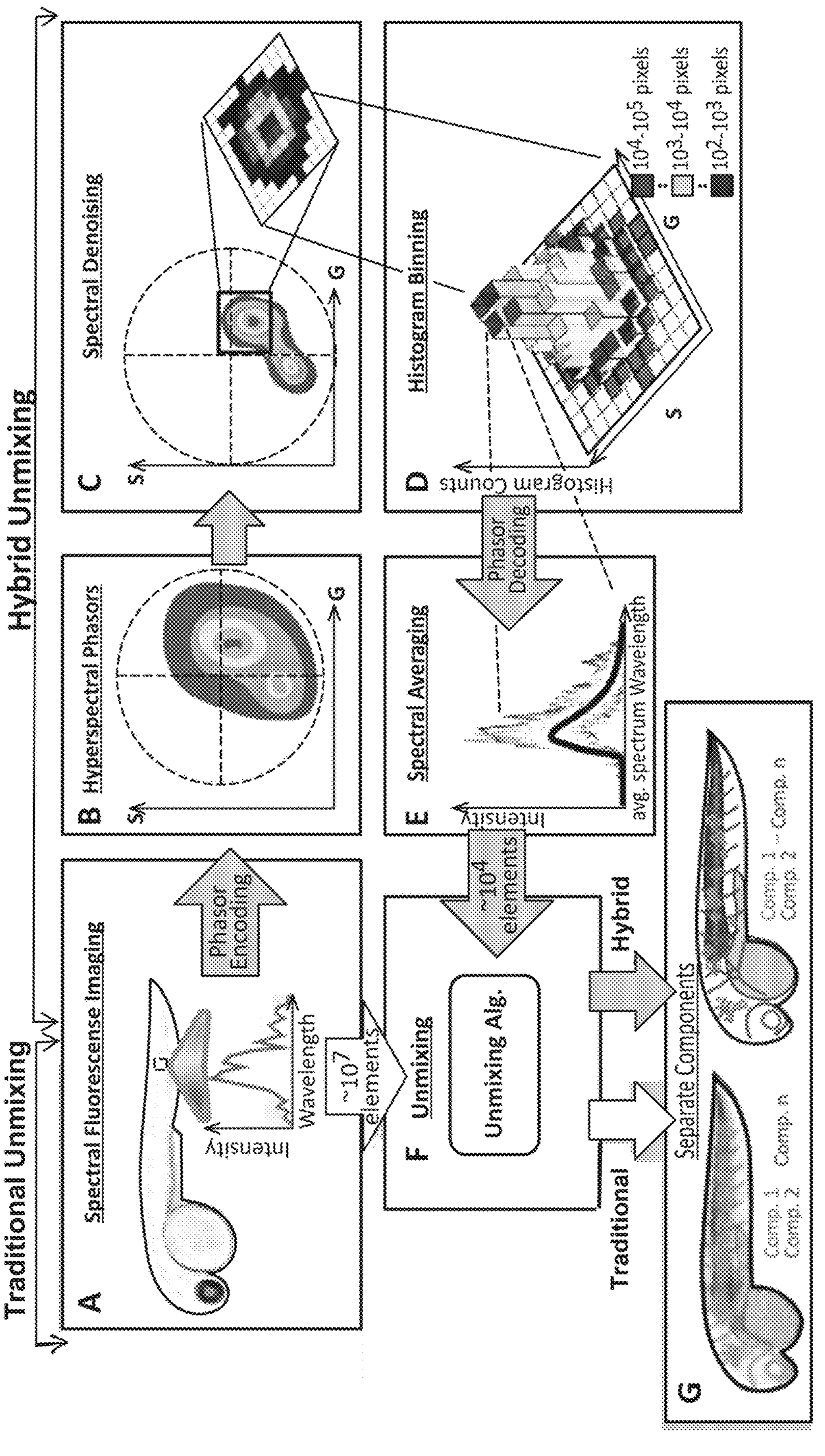
FIG. 1 schematically illustrates how the systems and methods discussed herein, such as those describing Hybrid Unmixing (HyU) may enhance analysis of multiplexed hyperspectral fluorescent signals in vivo. In this example, (A) Multicolor fluorescent biological sample (here a zebrafish embryo) is imaged in hyperspectral mode, collecting the fluorescence spectrum of each voxel in the specimen; (B) HyU represents spectral data as a phasor plot, a 2D histogram of the real and imaginary Fourier components (at a single harmonic); (C) spectral denoising filter may reduce the Poisson and instrumental noise on the phasor histogram, providing the first signal improvement; (D) the phasor may act as an encoder, where each histogram-bin corresponds to a number n of pixels, each with a relatively similar spectrum (E). Summing these spectra effectively averages the spectra for that phasor position. This denoising results in cleaner average spectrum for this set of pixels, which are ideally suited for analytical decomposition through unmixing algorithms (F). (G) Unmixing results in images that separated into spectral components. Here, linear unmixing (LU) is used for unmixing, but HyU is compatible with any unmixing algorithm. Note that HyU may offer a major reduction in data size and complexity of the LU (or any other unmixing) computation, because the calculation is applied to the $10^4$ histogram bins (D), rather the the ~$10^7$ voxels in the specimen (A). This reduces the number of calculations required for LU dramatically.

Illustrative implementations are now described. Other implementations may be used in addition or instead. Details that may be apparent or unnecessary may be omitted to save space or for a more effective presentation. Some implementations may be practiced with additional components or steps and/or without all the components or steps that are described.

This disclosure generally relates to imaging systems. This disclosure relates to hyperspectral imaging systems. This disclosure further relates to hyperspectral imaging systems that generate an unmixed color image of a target. This disclosure further relates to a hyperspectral imaging system that is configured to use a hybrid unmixing technique to provide enhanced imaging of a target. This disclosure further relates to a hyperspectral imaging system that is configured to use a hybrid unmixing technique to provide enhanced imaging of multiplexed fluorescence labels, enabling longitudinal imaging of multiple fluorescent signals with reduced illumination intensities. This disclosure further relates to hyperspectral imaging systems that are used in diagnosing a health condition.

This disclosure also relates to a hyperspectral imaging system for generating a representative image of a target. The hyperspectral imaging system may be configured to implement one or more hybrid unmixing technique(s). For example, one or more hardware computer processors may be configured to execute program instructions to cause the hyperspectral imaging system to perform one or more operations relating to hybrid unmixing. Hybrid unmixing, or operations relating thereto, such as those executed by a hardware computer processor and/or performed by a hyperspectral imaging system may be referred to herein, collectively or individually, as hybrid unmixing (HyU).

In this disclosure, the hyperspectral imaging system may include an image forming system. The image forming system may have a configuration to acquire a detected radiation of the target, wherein the detected radiation comprises at least two (target) waves, each target wave having a detected intensity and a different detected wavelength; to form a target image using the detected target radiation, wherein the target image comprises at least two (image) pixels, and wherein each image pixel corresponds to one physical point on the target; to form at least one (intensity) spectrum for each image pixel using the (detected) intensity and the (detected) wavelength of each target wave; to transform the intensity spectrum of each image pixel using a Fourier transform into a complex-valued function based on the intensity spectrum of each image pixel, wherein each complex-valued function has at least one real component and at least one imaginary component; to form one phasor point on a phasor plane for each image pixel by plotting value of the real component against value of the imaginary component, wherein the value of the real component is referred as the real value hereafter, and wherein the value of the imaginary component is referred as the imaginary value hereafter; and to form a (phasor) histogram comprising at least two phasor bins, wherein each (phasor) bin comprises at least one phasor point.

In this disclosure, the image forming system may have a (further) configuration to aggregate the detected spectra belonging to the image pixels of each phasor bin, to generate a representative intensity spectrum for each phasor bin; to unmix representative intensity spectra of the phasor bins by using an unmixing technique, thereby determining abundance of each spectral endmember of the detected radiation; to assign a color to a corresponding image pixel of the target by using the abundance of each spectral endmember in the representative intensity spectra and the detected intensity belonging to the image pixel; and to generate a representative image of the target representing the abundance of each spectral endmember.

In this disclosure, the intensity spectra aggregated in each phasor bin may have a relatively similar intensity spectrum or a substantially same intensity spectrum. Summing or averaging these substantially similar intensity spectra effectively averages the intensity spectra to generate a representative (or average) intensity spectrum for that phasor position. Summing or averaging these substantially similar intensity spectra may be achieved by any mathematical conventional or known manner. That is, any summing or averaging mathematical technique that may yield the representative intensity spectrum is within the scope of this disclosure.

In this disclosure, the image forming system may also have a (further) configuration that may aggregate the detected spectra belonging to the image pixels of each phasor bin. The detected spectra belonging to the image pixels of the same bin may have substantially the same detected intensity and the detected wavelength.

In this disclosure, any (spectral) unmixing technique that may unmix a detected target radiation, intensity spectra, and/or representative intensity spectra is within the scope of this disclosure. The unmixing technique may be a linear unmixing technique. The unmixing technique may be a fully constrained least squares unmixing technique, a matrix inversion unmixing technique, non-negative matrix factorization unmixing technique, geometric unmixing technique, Bayesian unmixing technique, sparse unmixing technique, or any combination thereof.

The image forming system of this disclosure may have a further configuration that applies a denoising filter to reduce a Poisson noise and/or instrumental noise of the detected radiation. The image forming system may also have a further configuration that applies a denoising filter on both the real component and the imaginary component of each complex-valued function at least once so as to produce a denoised real value and a denoised imaginary value for each image pixel. The denoising filter may be applied after the image forming system transforms the formed intensity spectrum belonging to each image pixel using the Fourier transform into the complex-valued function; and/or before the image forming system forms one phasor point on the phasor plane for each image pixel. The image forming system may also have a further configuration that may apply a denoising filter to the value of the real component and/or the value of the imaginary component after the image forming system forms one phasor point on the phasor plane for each image pixel. The denoised real value may be used as the real value for each image pixel and the denoised imaginary value for each image pixel may be used as the imaginary value to form one phasor point on the phasor plane for each image pixel.

An exemplary HyU hyperspectral imaging system, which may enhance analysis of multiplexed hyperspectral fluorescent signals in vivo, is shown in FIG. 1. In this example, a multicolor fluorescent biological sample (here a zebrafish embryo) may be imaged in a hyperspectral mode, collecting the fluorescence spectrum of each voxel in the specimen FIG. 1A; the fluorescence spectral data are transformed to a phasor plot, a 2D histogram of the real and imaginary Fourier components (at a single harmonic) (FIG. 1B); spectral denoising filters may be applied to the values of the phasor points to reduce the Poisson noise and instrumental noise on the phasor histogram, providing a signal improvement (FIG. 1C); the phasor transformation may act as an encoder such that each histogram-bin corresponds to a number n of (image) pixels, each with a relatively similar spectrum (FIG. 1D); summing or averaging these (intensity) spectra effectively averages the (intensity) spectra to generate a representative intensity spectrum for that phasor position (FIG. 1E). Such generation of the representative intensity spectrum may further denoises the detected image radiation, which may be suited for analytical decomposition through unmixing algorithms (FIG. 1F). Unmixing may result in images that are separated into spectral components (FIG. 1G). Here, a linear unmixing (LU) technique is used for unmixing, but HyU is compatible with any unmixing technique. Note that HyU may offer a major reduction in data size and complexity of an unmixing computation, because, for example, the computation may be applied to the $10^4$ histogram bins (FIG. 1D), rather the ~$10^7$ voxels in the specimen (FIG. 1A). This HyU approach may reduce the number of calculations required for the conventional unmixing computations dramatically.

The hyperspectral imaging system may further comprise an optics system. The optics system may include at least one optical component. The at least one optical component may include at least one optical detector. The at least one optical detector may have a configuration that may detect electromagnetic radiation absorbed, transmitted, refracted, reflected, and/or emitted from at least one physical point on the target, thereby forming the target radiation; wherein the target radiation comprises at least two target waves, each target wave having an intensity and a different wavelength. The at least one optical detector may have a further configuration that may detect the intensity and the wavelength of each target wave. The at least one optical detector may also have a further configuration that may transmit the detected target radiation, and each target wave's detected intensity and detected wavelength to the image forming system to be acquired. The image forming system may further comprise a control system, a hardware processor, a memory, and a display. The image forming system may have a further configuration that may display the representative image of the target on the image forming system's display.

Figure 37:
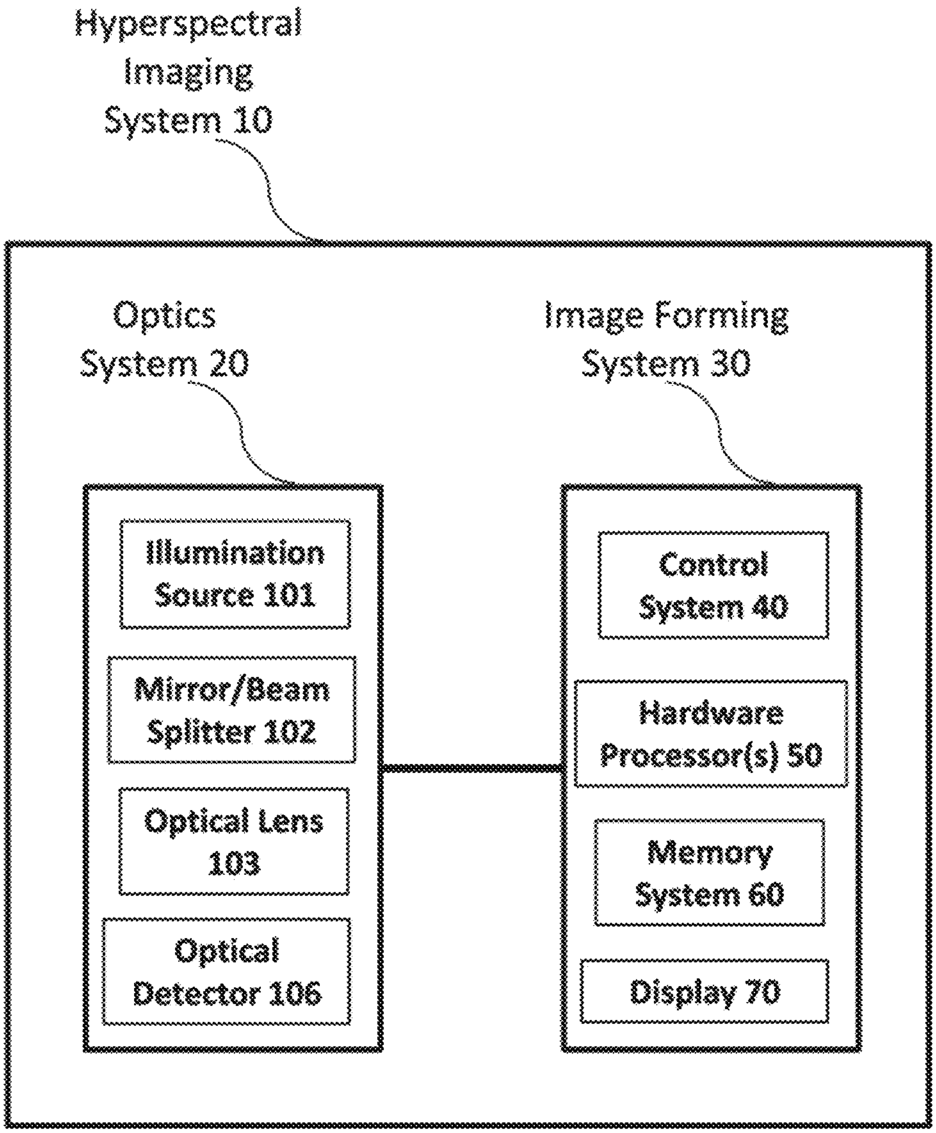
FIG. 37 illustrates an exemplary hyperspectral imaging system comprising an exemplary optics system and an exemplary image forming system.
Figure 45:
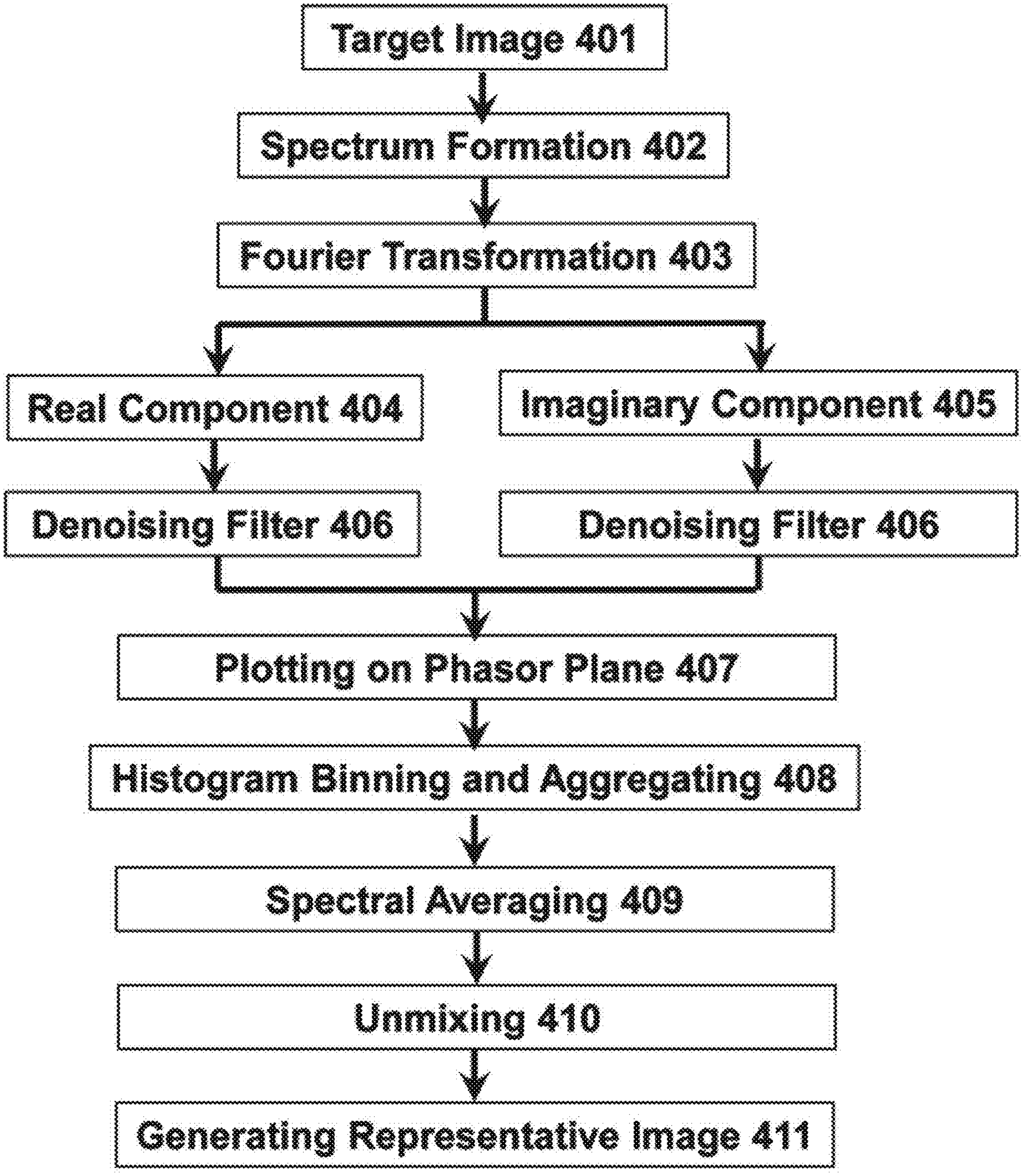
FIG. 45 illustrates example features of an exemplary image forming system that may be used to generate an unmixed color image of a target.
Figure 46:
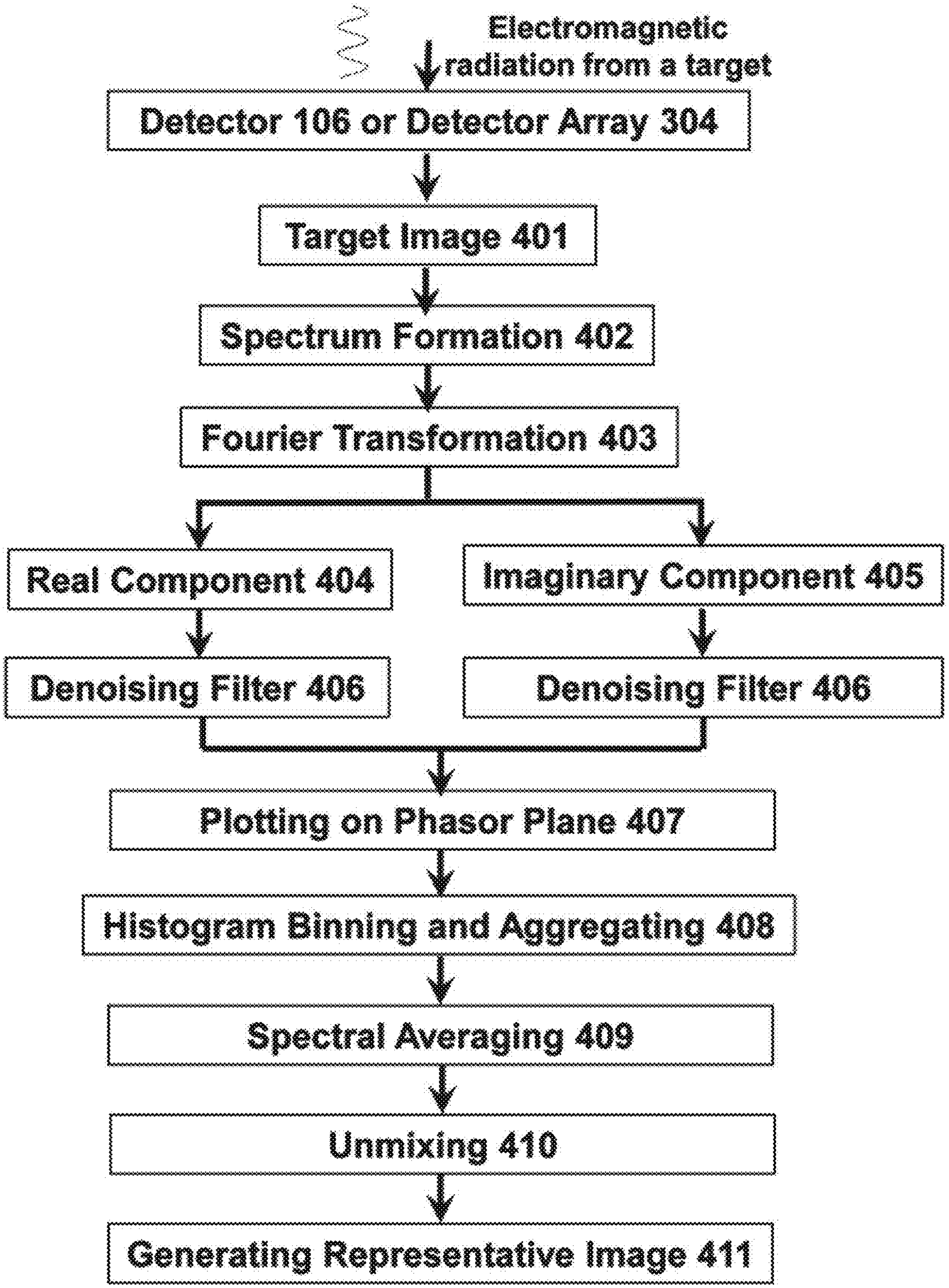
FIG. 46 illustrates example features of an exemplary image forming system that may be used to generate an unmixed color image of a target.

One example of the exemplary hyperspectral imaging system comprising an optics system and an image forming system is schematically shown in FIG. 37. The hyperspectral imaging system 10 may include an optics system 20, an image forming system 30, or a combination thereof. For example, the hyperspectral imaging system may include and an optics system and an image forming system. For example, the hyperspectral imaging system may include an image forming system. Exemplary optics systems are shown in FIGS. 38-44. An exemplary configuration of the image forming system is shown in FIG. 45. An exemplary configuration of the hyperspectral imaging system is shown in FIG. 46.

Any of the example optics system shown and/or discussed herein may include at least one optical component. Examples of the at least one optical component are a detector ("optical detector"), a detector array ("optical detector array"), a source to illuminate the target ("illumination source"), a first optical lens, a second optical lens, an optical filter, a dispersive optic system, a dichroic mirror/beam splitter, a first optical filtering system placed between the target and the at least one optical detector, a second optical filtering system placed between the first optical filtering system and the at least one optical detector, or a combination thereof. For example, the at least one optical component may include at least one optical detector. For example, the at least one optical component may include at least one optical detector and at least one illumination source. For example, the at least one optical component may include at least one optical detector, at least one illumination source, at least one optical lens, at least one optical filter, and at least one dispersive optic system. For example, the at least one optical component may include at least one optical detector, at least one illumination source, a first optical lens, a second optical lens, and a dichroic mirror/beam splitter. For example, the at least one optical component may include at least one optical detector, at least one illumination source, an optical lens, a dispersive optic; and wherein at least one optical detector is an optical detector array. For example, the at least one optical component may include at least one optical detector, at least one illumination source, an optical lens, a dispersive optic, a dichroic mirror/beam splitter; and wherein at least one optical detector is an optical detector array. For example, the at least one optical component may include at least one optical detector, at least one illumination source, an optical lens, a dispersive optic, a dichroic mirror/beam splitter; wherein at least one optical detector is an optical detector array; and wherein the illumination source directly illuminates the target. These optical components may form, for example, the exemplary optics systems shown in FIGS. 38-44.

Any of the example optical systems shown and/or discussed herein may include an optical microscope. Examples of the optical microscope may be a confocal fluorescence microscope, a two-photon fluorescence microscope, or a combination thereof.

The at least one optical detector shown and/or discussed herein may have a configuration that detects electromagnetic radiation absorbed, transmitted, refracted, reflected, and/or emitted ("target radiation") by at least one physical point on the target. The target radiation may include at least one wave ("target wave"). The target radiation may include at least two target waves. Each target wave may have an intensity and a different wavelength. The at least one optical detector may have a configuration that detects the intensity and the wavelength of each target wave. The at least one optical detector may have a configuration that transmits the detected target radiation to the image forming system. The at least one optical detector may have a configuration that transmits the detected intensity and wavelength of each target wave to the image forming system. The at least one optical detector may have any combination of these configurations.

The at least one optical detector shown and/or discussed herein may include a photomultiplier tube, a photomultiplier tube array, a digital camera, a hyperspectral camera, an electron multiplying charge coupled device, a Sci-CMOS, a digital camera, or a combination thereof. The digital camera may be any digital camera. The digital camera may be used together with an active filter for detection of the target radiation. The digital camera may also be used together with an active filter for detection of the target radiation, for example, comprising, luminescence, thermal radiation, or a combination thereof.

The target radiation shown and/or discussed herein may include an electromagnetic radiation emitted by the target. The electromagnetic radiation emitted by the target may include luminescence, thermal radiation, or a combination thereof. The luminescence may include fluorescence, phosphorescence, or a combination thereof. For example, the electromagnetic radiation emitted by the target may include fluorescence, phosphorescence, thermal radiation, or a combination thereof. For example, the electromagnetic radiation emitted by the target may include fluorescence. The at least one optical component may further include a first optical filtering system. The at least one optical component may further include a first optical filtering system and a second optical filtering system. The first optical filtering system may be placed between the target and the at least one optical detector. The second optical filtering system may be placed between the first optical filtering system and the at least one optical detector. The first optical filtering system may include a dichroic filter, a beam splitter type filter, or a combination thereof. The second optical filtering system may include a notch filter, an active filter, or a combination thereof. The active filter may include an adaptive optical system, an acousto-optic tunable filter, a liquid crystal tunable bandpass filter, a Fabry-Perot interferometric filter, or a combination thereof.

The at least one optical detector shown and/or discussed herein may detect the target radiation at a wavelength in the range of 300 nm to 800 nm. The at least one optical detector may detect the target radiation at a wavelength in the range of 300 nm to 1,300 nm.

The at least one illumination source may generate an electromagnetic radiation ("illumination source radiation"). The illumination source radiation may include at least one wave ("illumination wave"). The illumination source radiation may include at least two illumination waves. Each illumination wave may have a different wavelength. The at least one illumination source may directly illuminate the target. In this configuration, there is no optical component between the illumination source and the target. The at least one illumination source may indirectly illuminate the target. In this configuration, there is at least one optical component between the illumination source and the target. The illumination source may illuminate the target at each illumination wavelength by simultaneously transmitting all illumination waves. The illumination source may illuminate the target at each illumination wavelength by sequentially transmitting all illumination waves.

In this disclosure, the illumination source may include a coherent electromagnetic radiation source. The coherent electromagnetic radiation source may include a laser, a diode, a two-photon excitation source, a three-photon excitation source, or a combination thereof.

The illumination source radiation may include an illumination wave with a wavelength in the range of 300 nm to 1,300 nm. The illumination source radiation may include an illumination wave with a wavelength in the range of 300 nm to 700 nm. The illumination source radiation may include an illumination wave with a wavelength in the range of 690 nm to 1,300 nm. For example, the illumination source may be a one-photon excitation source that can generate electromagnetic radiation in the range of 300 to 700 nm. For example, such one-photon excitation source may generate an electromagnetic radiation that may include a wave with a wavelength of about 405 nm, about 458 nm, about 488 nm, about 514 nm, about 554 nm, about 561 nm, about 592 nm, about 630 nm, or a combination thereof. In another example, the source may be a two-photon excitation source that can generate electromagnetic radiation in the range of 690 nm to 1,300 nm. Such excitation source may be a tunable laser. Yet in another example, the source may a one-photon excitation source and a two-photon excitation source that can generate electromagnetic radiation in the range of 300 nm to 1,300 nm. For example, such one-photon excitation source may generate an electromagnetic radiation that may include a wave with a wavelength of about 405 nm, about 458 nm, about 488 nm, about 514 nm, about 554 nm, about 561 nm, about 592 nm, about 630 nm, or a combination thereof. For example, such two-photon excitation source may be capable of generating electromagnetic radiation in the range of 690 nm to 1,300 nm. Such two-photon excitation source may be a tunable laser.

The intensity of the illumination source radiation may not be higher than a certain level such that when the target is illuminated the target is not damaged by the illumination source radiation.

The hyperspectral imaging system may include a microscope. The microscope may be any microscope. For example, the microscope may be an optical microscope. Any optical microscope may be suitable for the system. Examples of an optical microscope may be a two-photon microscope, a one-photon confocal microscope, or a combination thereof. Examples of the two-photon microscopes are disclosed in Alberto Diaspro "Confocal and Two-Photon Microscopy: Foundations, Applications and Advances" Wiley-Liss, New York, November 2001; and Greenfield Sluder and David E. Wolf "Digital Microscopy" 4th Edition, Academic Press, Aug. 20, 2013. The entire content of each of these publications is incorporated herein by reference.

Figure 38:
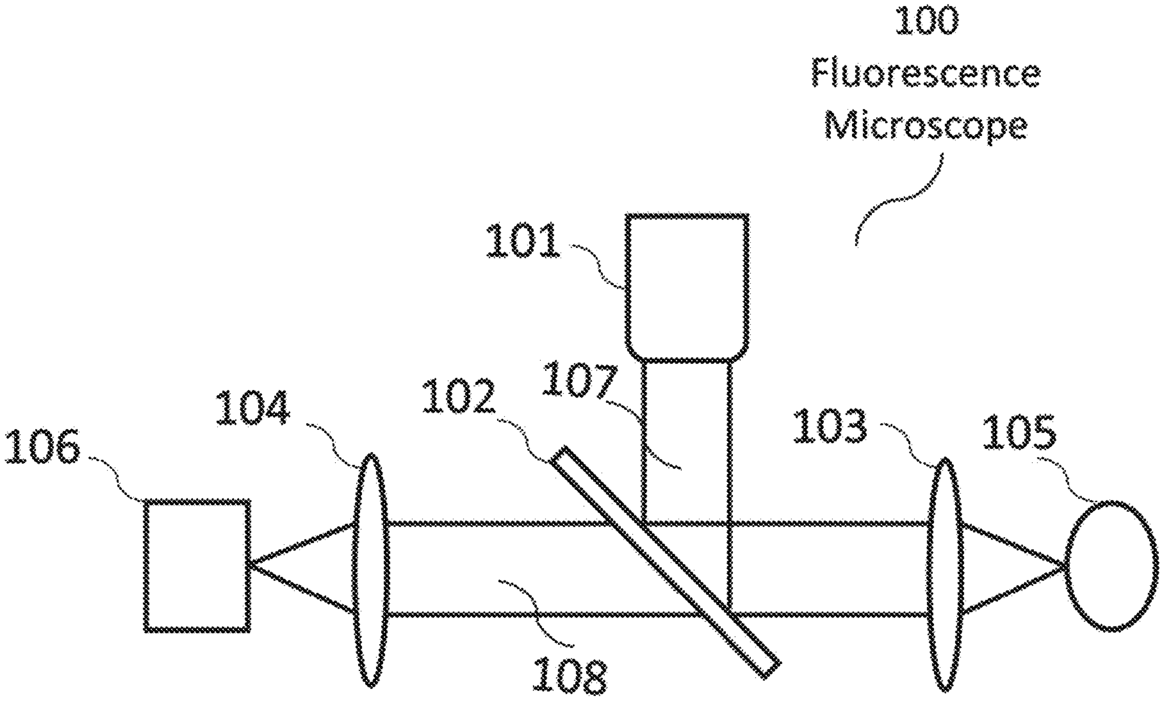
FIG. 38 illustrates an exemplary hyperspectral imaging system comprising an exemplary optics system, a fluorescence microscope. This system may generate an unmixed color image of a target by using an exemplary image forming system comprising features disclosed, for example in FIGS. 45-46.

An exemplary optics system comprising a fluorescence microscope 100 is shown in FIG. 38. This exemplary optics system may include at least one optical component. In this system, optical components may include an illumination source 101, a dichroic mirror/beam splitter 102, a first optical lens 103, a second optical lens 104, and a detector 106. These optical components may form a fluorescence microscope 100. This exemplary system may be suitable to form an image of a target 105. The source may generate an illumination source radiation 107. The dichroic mirror/beam splitter 102 may reflect the illumination wave to illuminate the target 105. The target, as a result, may emit an electromagnetic radiation (e.g. fluorescence) 108 and reflect back the illumination source radiation 107. The dichroic mirror/beam splitter 102 may filter the illumination source radiation from the target and may substantially prevent the illumination source radiation reflected from the target reaching the detector. The detected image of the target and the measured intensity of the target radiation by using these optical components may generate an unmixed color image of the target by using the system features/configurations of this disclosure. For example, this unmixed color image of the target may be generated by using any of the system features/configurations schematically shown in FIGS. 45-46.

Figure 39:
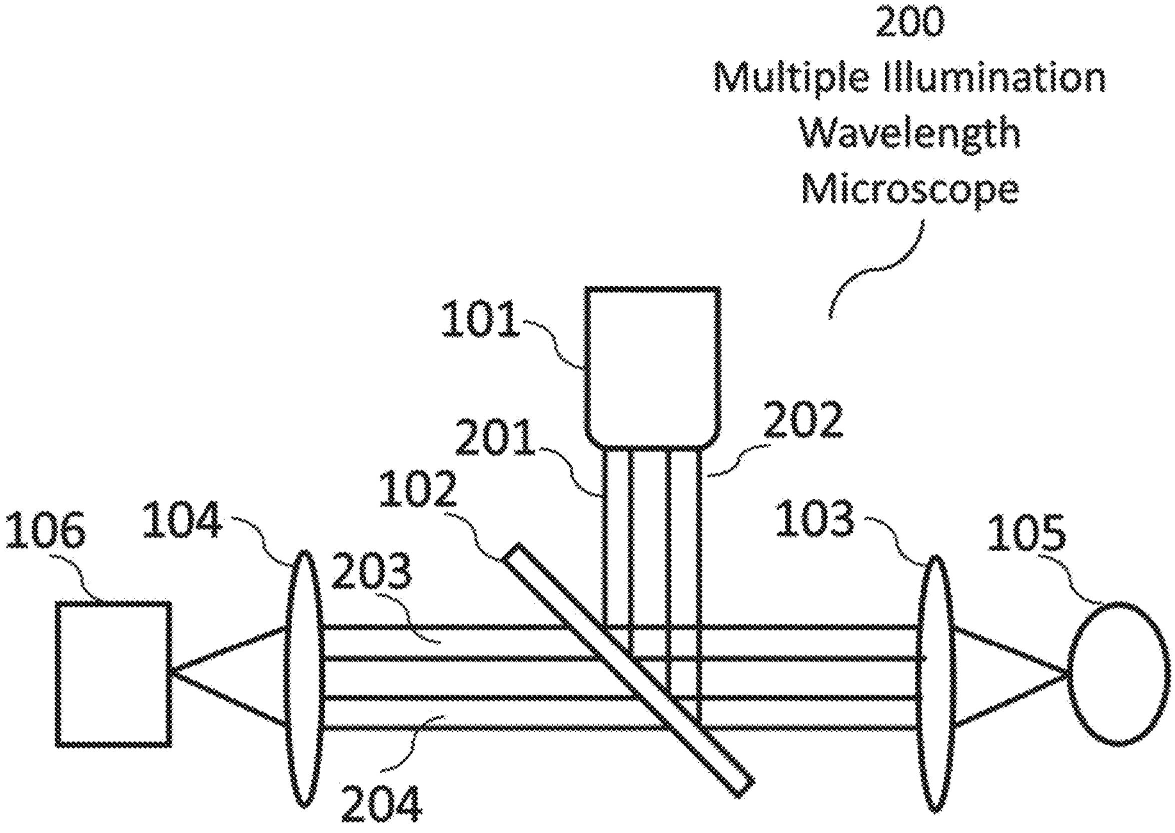
FIG. 39 illustrates an exemplary hyperspectral imaging system comprising an exemplary optics system, a multiple illumination wavelength microscope. This system may generate an unmixed color image of a target by using an exemplary image forming system comprising features disclosed, for example in FIGS. 45-46.

An exemplary optics system comprising a multiple illumination wavelength microscope 200 is shown in FIG. 39. This exemplary optics system may include at least one optical component. In this system, the optical components may include an illumination source 101, a dichroic mirror/beam splitter 102, a first optical lens 103, a second optical lens 104, and a detector 106. These optical components may form a hyperspectral imaging system comprising a fluorescence microscope, a reflectance microscope, or a combination thereof. This exemplary system may be suitable to form an image of a target 105. The illumination source may generate an illumination source radiation comprising multiple waves wherein each wave may have a different wavelength. For example, the illumination source in this example may generate an illumination source radiation comprising two waves each having a different wavelength, 201 and 202. The source may sequentially illuminate the target at each wavelength. The dichroic mirror/beam splitter 102 may reflect the illumination source radiation to illuminate the target 105. The target, as a result, may emit and/or may reflect back a wave of the electromagnetic radiation. In one example, the dichroic mirror/beam splitter 102 may filter the electromagnetic radiation from the target and may substantially allow emitted radiation to reach the detector and substantially prevent the illumination source radiation reflected from the target reaching the detector. In another example, the dichroic mirror/beam splitter 102 may transmit only the reflected waves from the target, but substantially filter emitted waves from the target, thereby allowing only the reflected waves from the target to reach the detector. Yet in another example, the dichroic mirror/beam splitter 102 may transmit both the reflected radiation and emitted radiation from the target, thereby allowing both the reflected radiation and the reflected radiation from the target to reach the detector. In this example, multiple waves may reach the detector, each having a different wavelength. For example, the electromagnetic radiation reaching the detector may have two waves 203 and 204, each having a different wavelength. The detected image of the target and the measured intensity of the target radiation by using these optical components may generate an unmixed color image of the target by using the system features/configurations of this disclosure. For example, this unmixed color image of the target may be generated by using any of the system features/configurations schematically shown in FIG. 45-46.

Figure 40:
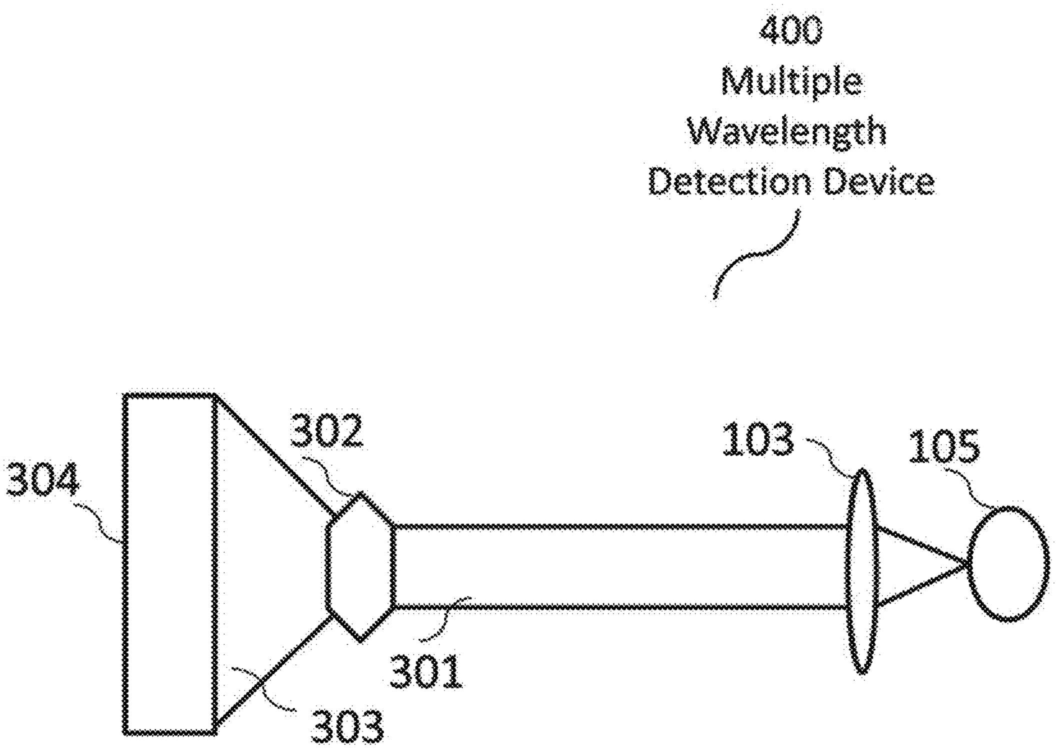
FIG. 40 illustrates an exemplary hyperspectral imaging system comprising an exemplary optics system, a multiple illumination wavelength device. This system may generate an unmixed color image of a target by using an exemplary image forming system comprising features disclosed, for example in FIGS. 45-46.

Another exemplary hyperspectral imaging system comprising a multiple wavelength detection microscope 300 is shown in FIG. 40. This exemplary hyperspectral imaging system may include at least one optical component. In this system, the optical components may include a first optical lens 103, a dispersive optic 302, and a detector array 304. These optical components may form a hyperspectral imaging system comprising a fluorescence device, a reflectance device, or a combination thereof. This exemplary system may be suitable to form an image of a target 105. The target may emit and/or may reflect a wave 301 of an electromagnetic radiation. In this example, at least one wave or at least two waves may reach the detector array. Each wave may have a different wavelength. The dispersive optic 302 may form a spectrally dispersed electromagnetic radiation 303. The detected image of the target and the measured intensity of the target radiation by using these optical components may generate an unmixed color image of the target by using the system features/configurations of this disclosure. For example, this unmixed color image of the target may be generated by using any of the system features/configurations schematically shown in FIGS. 45-46.

Figure 41:
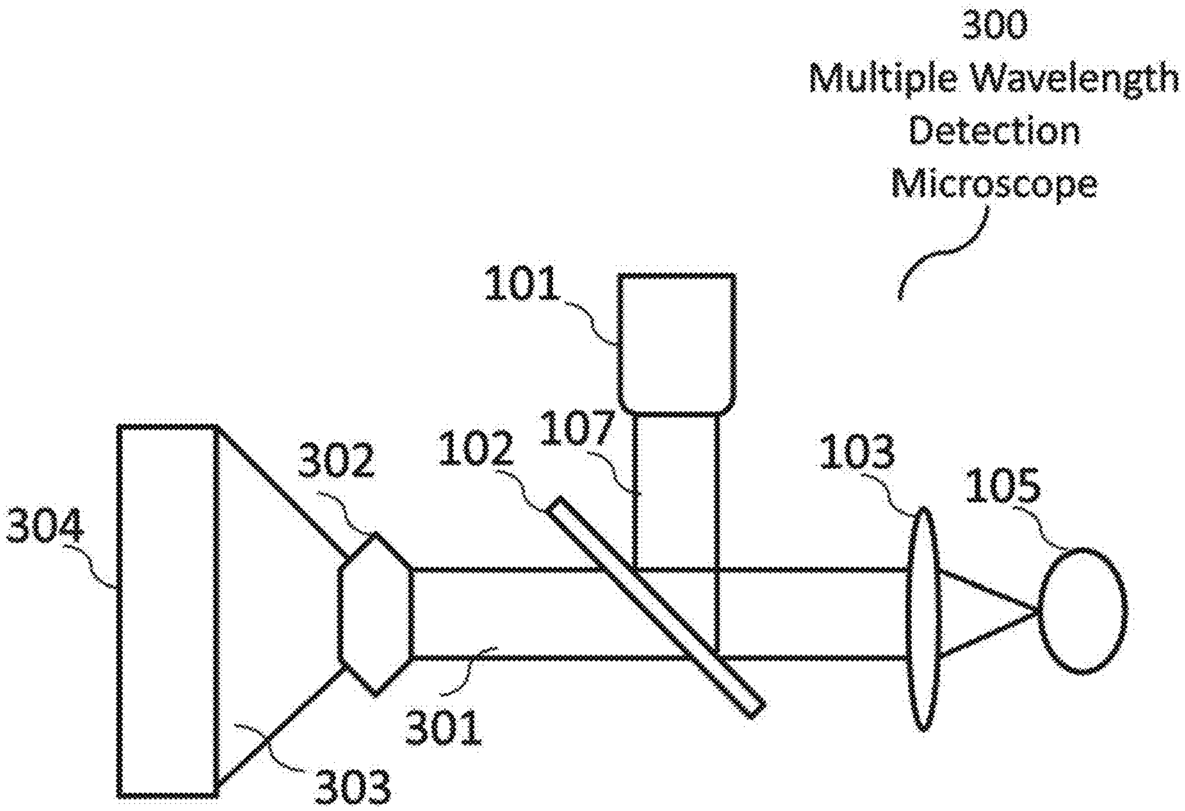
FIG. 41 illustrates an exemplary hyperspectral imaging system comprising an exemplary optics system, a multiple wavelength detection microscope. This system may generate an unmixed color image of a target by using an exemplary image forming system comprising features disclosed, for example in FIGS. 45-46.

Another exemplary hyperspectral imaging system comprising a multiple wavelength detection microscope 400 is shown in FIG. 41. This exemplary hyperspectral imaging system may include at least one optical component. In this system, the optical components may include an illumination source 101, a dichroic mirror/beam splitter 102, a first optical lens 103, a dispersive optic 302, and a detector array 304. These optical components may form a hyperspectral imaging system comprising a fluorescence device. This exemplary system may be suitable to form an image of a target 105. The illumination source may generate an illumination source radiation comprising at least one wave 107. Each wave may have a different wavelength. The source may sequentially illuminate the target at each wavelength. The dichroic mirror/beam splitter 102 may reflect the illumination wave to illuminate the target 105. The target, as a result, may emit a wave of the electromagnetic radiation. The dichroic mirror/beam splitter 102 may substantially allow the emitted wave 301 to reach the detector array but may filter the target radiation and thereby substantially prevent the waves reflected from the target to reach the detector array. In this example, the emitted radiation reaching detector array may include multiple waves, each having a different wavelength. The dispersive optic 302 may form a spectrally dispersed electromagnetic radiation 303. The detected image of the target and the measured intensity of the target radiation by using these optical components may generate an unmixed color image of the target by using the system features disclosed above. For example, this unmixed color image of the target may be generated by using any of the system features schematically shown in FIG. 45-46.

Figure 42:
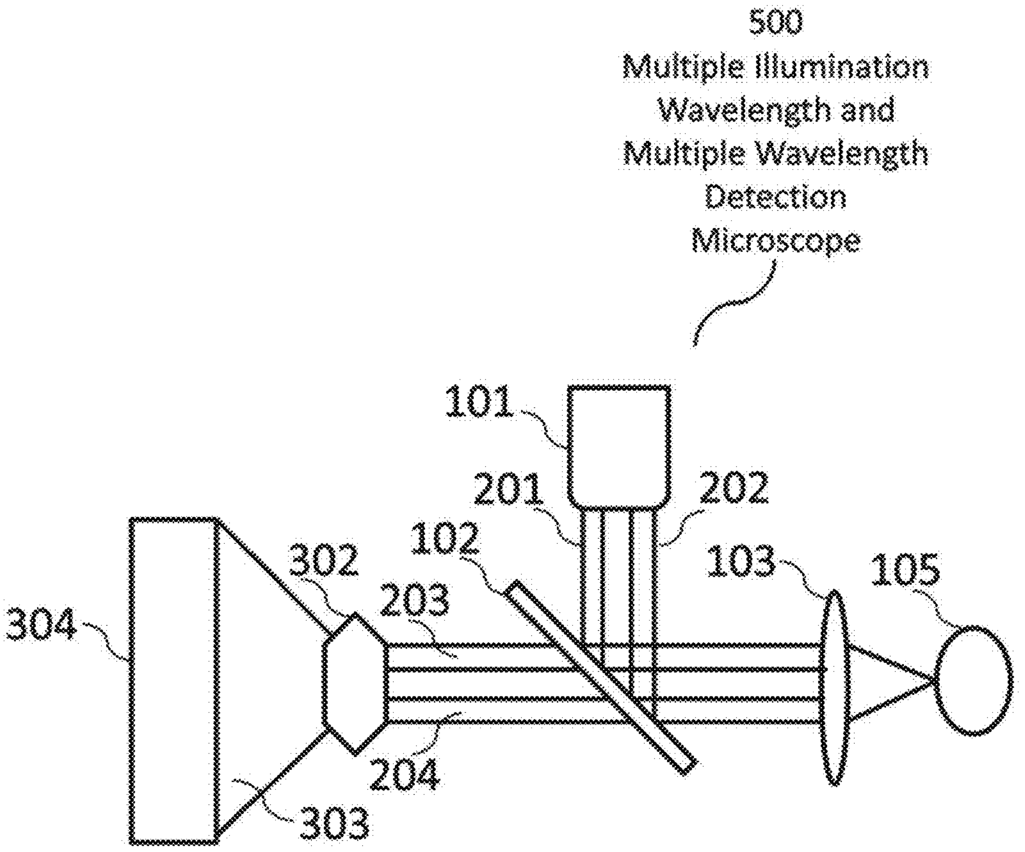
FIG. 42 illustrates an exemplary hyperspectral imaging system comprising an exemplary optics system, a multiple illumination wavelength and multiple wavelength detection microscope. This system may generate an unmixed color image of a target by using an exemplary image forming system comprising features disclosed, for example in FIGS. 45-46.

Another exemplary hyperspectral imaging system comprising a multiple illumination wavelength and multiple wavelength detection device 500 is shown in FIG. 42. This exemplary hyperspectral imaging system may include at least one optical component. In this system, the optical components may include an illumination source 101, a dichroic mirror/beam splitter 102, a first optical lens 103, a dispersive optic 302, and a detector array 304. These optical components may form a hyperspectral imaging system comprising a fluorescence microscope, a reflectance microscope, or a combination thereof. This exemplary system may be suitable to form an image of a target 105. The source may generate an illumination wave comprising multiple waves wherein each wave may have a different wavelength. For example, the illumination source in this example may generate an illumination source radiation comprising two waves each having a different wavelength, 201 and 202. The illumination source may sequentially illuminate the target at each wavelength. The dichroic mirror/beam splitter 102 may reflect the illumination radiation to illuminate the target 105. The target, as a result, may emit and/or may reflect back the electromagnetic radiation. In one example, the dichroic mirror/beam splitter 102 may filter the radiation from the target substantially allowing only emitted radiation reaching the detector array, but substantially preventing the radiation reflected from the target to reach the detector array. In another example, the dichroic mirror/beam splitter 102 may transmit only the reflected waves from the target, but substantially filter emitted waves from the target, thereby substantially allowing only the reflected waves from the target to reach the detector array. Yet in another example, the dichroic mirror/beam splitter 102 may substantially transmit both the reflected waves and emitted waves from the target, thereby allowing both the reflected waves and the reflected beams from the target to reach the detector array. In this example, the beam reaching detector array may have multiple waves, each having a different wavelength. For example, the beam reaching the detector array may have two waves 203 and 204, each having a different wavelength. The dispersive optic 302 may form a spectrally dispersed electromagnetic radiation 303. The detected image of the target and the measured intensity of the target radiation by using these optical components may generate an unmixed color image of the target by using the system features/configurations of this disclosure. For example, this unmixed color image of the target may be generated by using any of the system features/configurations schematically shown in FIG. 45-46.

Figure 43:
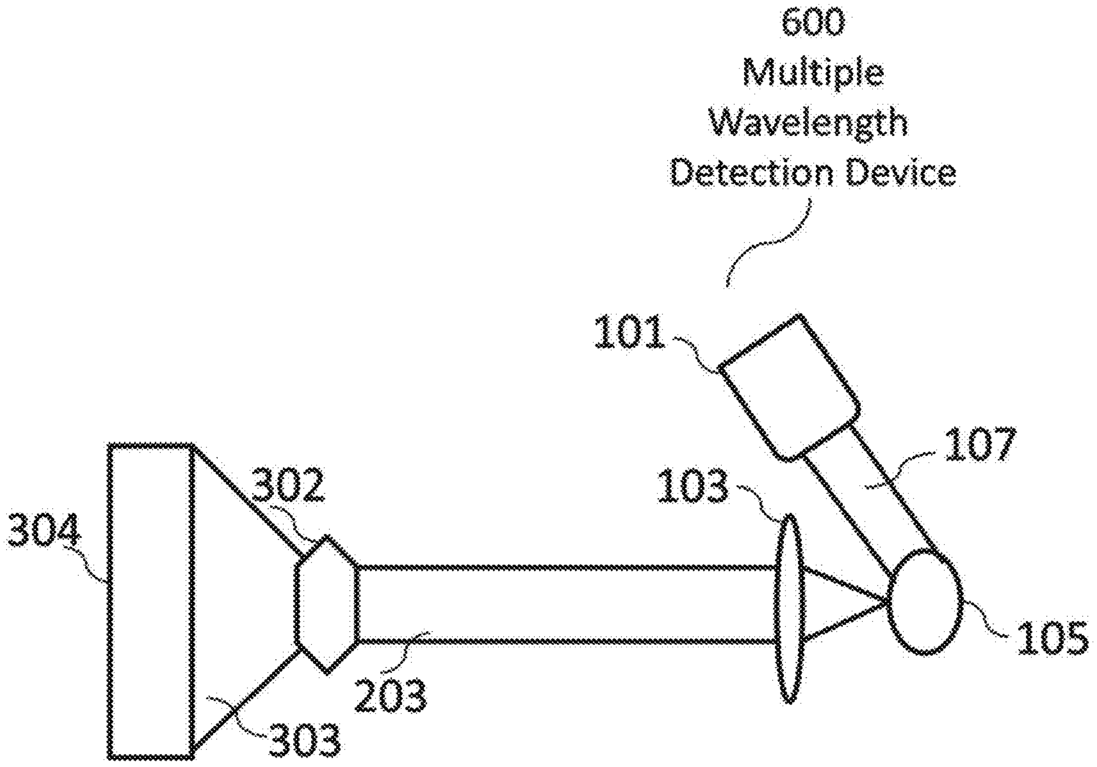
FIG. 43 illustrates an exemplary hyperspectral imaging system comprising an exemplary optics system, a multiple wavelength detection device. This system may generate an unmixed color image of a target by using an exemplary image forming system comprising features disclosed, for example in FIGS. 45-46.

Another exemplary optical system comprising a multiple wavelength detection device 600 is shown in FIG. 43. This exemplary optical system may include at least one optical component. In this system, the optical components may include an illumination source 101, a first optical lens 103, a dispersive optic 302, and a detector array 304. These optical components may form a hyperspectral imaging system comprising a fluorescence and/or reflectance device. This exemplary system may be suitable to form an image of a target 105. The illumination source may generate an illumination source radiation comprising at least one wave 107. Each wave may have a different wavelength. The source may sequentially illuminate the target at each wavelength. The target, as a result, may emit, reflect, refract, and/or absorb a beam 203 of the electromagnetic radiation. In this example, the emitted, reflected, refracted, and/or absorbed beam reaching detector array may include multiple waves, each having a different wavelength. The dispersive optic 302 may form a spectrally dispersed electromagnetic radiation 303. The detected image of the target and the measured intensity of the target radiation by using these optical components may generate an unmixed color image of the target by using the system features/configurations of this disclosure. For example, this unmixed color image of the target may be generated by using any of the system features/configurations schematically shown in FIG. 45-46.

Figure 44:
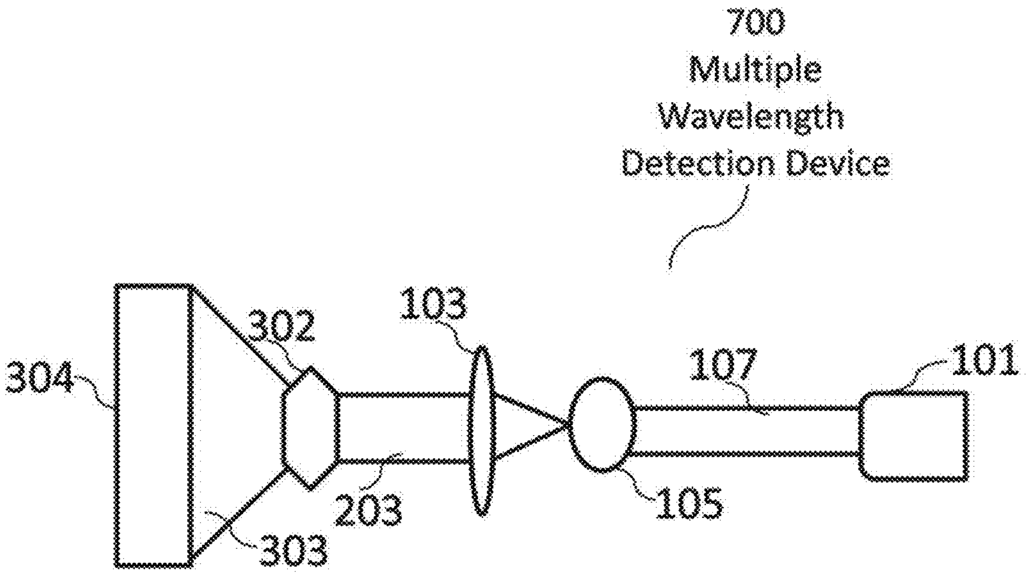
FIG. 44 illustrates an exemplary hyperspectral imaging system comprising an exemplary optics system, a multiple wavelength detection device. This system may generate an unmixed color image of a target by using an exemplary image forming system comprising features disclosed, for example in FIGS. 45-46.

Another exemplary optics system comprising a multiple wavelength detection device 700 is shown in FIG. 44. This optics system may include at least one optical component. In this system, the optical components may include an illumination source 101, a first optical lens 103, a dispersive optic 302, and a detector array 304. These optical components may form a hyperspectral imaging system comprising a fluorescence and/or reflectance device. This exemplary system may be suitable to form an image of a target 105. The illumination source may generate an illumination source radiation comprising at least one wave 107. Each wave may have a different wavelength. The source may sequentially illuminate the target at each wavelength. The target, as a result, may emit, transmit, refract, and/or absorb a beam 203 of the electromagnetic radiation. In this example, the emitted, transmitted, refracted, and/or absorbed electromagnetic radiation reaching detector array may include multiple waves, each having a different wavelength. The dispersive optic 302 may form a spectrally dispersed electromagnetic radiation 303. The detected image of the target and the measured intensity of the target radiation by using these optical components may generate an unmixed color image of the target by using the system features/configurations of this disclosure. For example, this unmixed color image of the target may be generated by using any of the system features/configurations schematically shown in FIG. 45-46.

In this disclosure, the image forming system 30 may include a control system 40, a hardware processor 50, a memory system 60, a display 70, or a combination thereof. An exemplary image forming system is shown in FIG. 37. The control system may be any control system. For example, the control system may control the optics system. For example, the control system may control at least one optical component of the optics system. For example, the control system may control the at least one optical detector to detect target radiation, detect the intensity and the wavelength of each target wave, transmit the detected intensity and wavelength of each target wave to the image forming system, and display the unmixed color image of the target. For example, the control system may control motions of the optical components, for example, opening and closure of optical shutters, motions of mirrors, and the like. The hardware processor can include microcontrollers, digital signal processors, application specific integrated circuit (ASIC), a field programmable gate array (FPGA) or other programmable logic device, discrete gate or transistor logic, discrete hardware components, or any combination thereof designed to perform the functions described herein. In an implementation, all of the processing discussed herein is performed by the one or more hardware processor(s). For example, the hardware processor may form the target image, perform phasor analysis, perform the Fourier transform of the intensity spectrum, apply the denoising filter, form the phasor plane, map back the phasor point(s), assigns the arbitrary color(s), generate the unmixed color image of the target, the like, or a combination of such configurations thereof. The memory system may be any memory system. For example, the memory system may receive and store inputs from the hardware processor. These inputs, for example, may be the target image, the target radiation, the intensity spectrum, the phasor plane, the unmixed color image of the target, the like, or a combination of such configurations. For example, the memory system may provide outputs to other components of the image forming system, for example, to the processor and/or the display. These outputs, for example, may be the target image, the target radiation, the intensity spectrum, the phasor plane, the unmixed color image of the target, the like, or a combination of such configurations. The display may be any display. For example, the display may display the target image, the intensity spectrum, the phasor plane, the unmixed color image of the target, the like, or a combination of such configurations. The image forming system 30 may be connected with the optics system 20 via a network. In some instances, the image forming system 30 may be located on a server that is remote from the optics system 20.

The image forming system may have a configuration that causes the optical detector to detect the target radiation and to transmit the detected intensity and wavelength of each target wave to the image forming system.

The image forming system may have a configuration that acquires the detected target radiation comprising the at least two target waves.

The image forming system may have a configuration that acquires a target radiation comprising at least two target waves, each wave having an intensity and a different wavelength.

The image forming system may have a configuration that acquires a target image, wherein the target image includes at least two pixels, and wherein each pixel corresponds to one physical point on the target.

The image forming system may have a configuration that forms an image of the target using the detected target radiation ("target image"). The target image may include at least one pixel. The target image may include at least two pixels. Each pixel corresponds to one physical point on the target.

The target image may be formed/acquired in any form. For example, the target image may have a visual form and/or a digital form. For example, the formed/acquired target image may be a stored data. For example, the formed/acquired target image may be stored in the memory system as data. For example, the formed/acquired target image may be displayed on the image forming system's display. For example, the formed/acquired target image may be an image printed on a paper or any similar media.

The image forming system may have a configuration that forms at least one spectrum for each pixel using the detected intensity and wavelength of each target wave ("intensity spectrum").

The image forming system may have a configuration that acquires at least one intensity spectrum for each pixel, wherein the intensity spectrum includes at least two intensity points.

The intensity spectrum may be formed/acquired in any form. For example, the intensity spectrum may have a visual form and/or a digital form. For example, the formed/acquired intensity spectrum may be a stored data. For example, the formed/acquired intensity spectrum may be stored in the memory system as data. For example, the formed/acquired intensity spectrum may be displayed on the image forming system's display. For example, the formed/acquired intensity spectrum may be an image printed on a paper or any similar media.

The image forming system may have a configuration that transforms the formed intensity spectrum of each pixel using a Fourier transform into a complex-valued function based on the intensity spectrum of each pixel, wherein each complex-valued function has at least one real component and at least one imaginary component.

The image forming system may have a configuration that applies a denoising filter on both the real component and the imaginary component of each complex-valued function at least once so as to produce a denoised real value and a denoised imaginary value for each pixel.

The image forming system may have a configuration that forms one point on a phasor plane ("phasor point") for each pixel by plotting the denoised real value against the denoised imaginary value of each pixel. The image forming system may form the phasor plane, for example, by using its hardware components, for example, the control system, the hardware processor, the memory or a combination thereof. The image forming system may display the phasor plane.

The phasor point and/or phasor plane may be formed/acquired in any form. For example, the phasor point and/or phasor plane may have a visual form and/or a digital form. For example, the formed/acquired phasor point and/or phasor plane may be a stored data. For example, the formed/acquired phasor point and/or phasor plane may be stored in the memory system as data. For example, the formed/acquired phasor point and/or phasor plane may be displayed on the image forming system's display. For example, the formed/acquired phasor point and/or phasor plane may be an image printed on a paper or any similar media.

The image forming system may have a configuration that maps back the phasor point to a corresponding pixel on the target image based on the phasor point's geometric position on the phasor plane. In this disclosure, the image forming system may have a configuration that maps back the phasor plane to the corresponding target image based on each phasor point's geometric position on the phasor plane. The image forming system may map back the phasor point, for example, by using its hardware components, for example, the control system, the hardware processor, the memory or a combination thereof.

The phasor point and/or phasor plane may be mapped back in any form. For example, the mapped back phasor point and/or phasor plane may have a visual form and/or a digital form. For example, the mapped back phasor point and/or phasor plane may be a stored data. For example, the mapped back phasor point and/or phasor plane may be stored in the memory system as data. For example, the mapped back phasor point and/or phasor plane may be displayed on the image forming system's display. For example, the mapped back phasor point and/or phasor plane may be an image printed on a paper or any similar media.

The image forming system may have a configuration that assigns an arbitrary color to the corresponding pixel based on the geometric position of the phasor point on the phasor plane.

The unmixed color image may be formed in any form. For example, the unmixed color image may have a visual form and/or a digital form. For example, the unmixed color image may be a stored data. For example, the unmixed color image may be stored in the memory system as data. For example, the unmixed color image may be displayed on the image forming system's display. For example, the unmixed color image may be an image printed on a paper or any similar media.

The image forming system may have a configuration that displays the unmixed color image of the target on the image forming system's display.

The image forming system may have any combination of any of the configurations shown and/or described herein, such as those described above.

The image forming system may use at least one harmonic of the Fourier transform to generate the unmixed color image of the target. The image forming system may use at least a first harmonic of the Fourier transform to generate the unmixed color image of the target. The image forming system may use at least a second harmonic of the Fourier transform to generate the unmixed color image of the target. The image forming system may use at least a first harmonic and a second harmonic of the Fourier transform to generate the unmixed color image of the target.

The denoising filter may be any denoising filter. For example, the denoising filter may be a denoising filter such that when the denoising filter is applied, the image quality is not compromised. For example, when the denoising filter is applied, the detected electromagnetic radiation intensity at each pixel in the image may not change. An example of a suitable denoising filter may include a median filter.

The unmixed color image of the target may be formed at a signal-to-noise ratio of the at least one spectrum in the range of 1.2 to 50. The unmixed color image of the target may be formed at a signal-to-noise ratio of the at least one spectrum in the range of 2 to 50.

One example implementation of a hyperspectral imaging system is schematically shown in FIG. 45. In this example, the imaging system may obtain an image of a target 401. The image may include at least two waves and at least two pixels. The system may form an image of the target using intensities of each wave and wavelengths of the at least two waves ("intensity spectrum") 402. The system may transform the intensity spectrum of each pixel by using a Fourier transform 403, thereby forming a complex-valued function based on the detected intensity spectrum of each pixel. Each complex-valued function may have at least one real component 404 and at least one imaginary component 405. The system may apply a denoising filter 406 on both the real component and the imaginary component of each complex-valued function at least once. (Denoising may also be applied before and/or after the spectrum formation to the intensities of the target radiation and/or the intensities of the intensity spectrum. Such configurations, which are within the scope of this invention, are not shown in FIG. 45.) The system may thereby obtain a denoised real value and a denoised imaginary value for each pixel. The system may plot the denoised real value against the denoised imaginary value for each image pixel. The system may thereby form a point on a phasor plane 407. The system may form at least one additional point on the phasor plane by using at least one more pixel of the image. The system may form a phasor histogram including at least two phasor bins, wherein each phasor bin may include at least one phasor point 408. The system may aggregate the detected spectra belonging to the image pixels of each phasor bin 408. The system may generate a representative intensity spectrum for each phasor bin, for example, by averaging the intensities of the spectra belonging to the same phasor bin 409. The system may unmix representative intensity spectra of the phasor bins by using an unmixing technique, thereby determining abundance of each spectral endmember of the detected radiation

410. The system may determine abundance of each spectral endmember in the representative intensity spectra and the detected intensity belonging to the image pixel; and generates a representative image of the target representing the abundance of each spectral endmember 411.

Another example implementation of the hyperspectral imaging system is schematically shown in FIG. 46. In this example, the hyperspectral imaging system may further include at least one detector 106 or a detector array 304. This imaging system may form an image of a target 401 by using the detector or the detector array. The image may include at least two waves and at least two image pixels. The system may form an image of the target using intensities of each wave and wavelengths of the at least two waves ("intensity spectrum") 402. The system may transform the intensity spectrum of each pixel by using a Fourier transform 403, thereby forming a complex-valued function based on the detected intensity spectrum of each pixel. Each complex-valued function may have at least one real component 404 and at least one imaginary component 405. The system may apply a denoising filter 406 on both the real component and the imaginary component of each complex-valued function at least once. (Denoising may also be applied before and/or after the spectrum formation to the intensities of the target radiation and/or the intensities of the intensity spectrum. Such configurations, which are within the scope of this invention, are not shown in FIG. 46.) The system may thereby obtain a denoised real value and a denoised imaginary value for each pixel. The system may plot the denoised real value against the denoised imaginary value for each image pixel. The system may thereby form a point on a phasor plane 407. The system may form at least one additional point on the phasor plane by using at least one more pixel of the image. The system may form a phasor histogram including at least two phasor bins, wherein each phasor bin may include at least one phasor point 408. The system may aggregate the detected spectra belonging to the image pixels of each phasor bin 408. The system may generate a representative intensity spectrum for each phasor bin, for example, by averaging the intensities of the spectra belonging to the same phasor bin 409. The system may unmix representative intensity spectra of the phasor bins by using an unmixing technique, thereby determining abundance of each spectral endmember of the detected radiation 410. The system may determine abundance of each spectral endmember in the representative intensity spectra and the detected intensity belonging to the image pixel; and generates a representative image of the target representing the abundance of each spectral endmember 411.

In this disclosure, the target may be any target. The target may be any target that has a specific spectrum of color. For example, the target may be a tissue, a fluorescent genetic label, an inorganic target, or a combination thereof.

The system may be calibrated by using a reference to assign colors to each pixel. The reference may be any known reference. For example, the reference may be any reference wherein unmixed color image of the reference is determined prior to the generation of unmixed color image of the target. For example, the reference may be a physical structure, a chemical molecule, a biological molecule, a biological activity (e.g. physiological change) as a result of physical structural change and/or disease.

The target radiation may include fluorescence. The hyperspectral imaging system suitable for fluorescence detection may include an optical filtering system. Examples of the optical filtering system are: a first optical filter to substantially decrease the intensity of the source radiation reaching to the detector. The first optical filter may be placed between the target and the detector. The first optical filter may be any optical filter. Examples of the first optical filter may be dichroic filter, a beam splitter type filter, or a combination thereof.

The hyperspectral imaging system suitable for fluorescence detection may further include a second optical filter. The second optical filter may be placed between the first optical filter and the detector to further decrease the intensity of the source radiation reaching the detector. The second optical filter may be any optical filter. Examples of the second optical filter may be a notch filter, an active filter, or a combination thereof. Examples of the active filter may be an adaptive optical system, an acousto-optic tunable filter, a liquid crystal tunable bandpass filter, a Fabry-Perot interferometric filter, or a combination thereof.

The hyperspectral imaging system may be calibrated by using a reference material to assign colors to each pixel. The reference material may be any known reference material. For example, the reference material may be any reference material wherein unmixed color image of the reference material is determined prior to the generation of unmixed color image of the target. For example, the reference material may be a physical structure, a chemical molecule (i.e. compound), a biological activity (e.g. physiological change) as a result of physical structural change and/or disease. The chemical compound may be any chemical compound. For example, the chemical compound may be a biological molecule (i.e. compound).

The hyperspectral imaging system may be used to diagnose any health condition. For example, the hyperspectral imaging system may be used to diagnose any health condition of any mammal. For example, the hyperspectral imaging system may be used to diagnose any health condition of a human. Examples of the health condition may include a disease, a congenital malformation, a disorder, a wound, an injury, an ulcer, an abscess, or the like. The health condition may be related to a tissue. The tissue may be any tissue. For example, the tissue may include a skin. Examples of a health condition related to a skin or tissue may be a skin lesion. The skin lesion may be any skin lesion. Examples of the skin lesion may be a skin cancer, a scar, an acne formation, a wart, a wound, an ulcer, or the like. Other examples of a health condition of a skin or tissue may be a makeup of a tissue or a skin, for example, the tissue or the skin's moisture level, oiliness, collagen content, hair content, or the like.

The target may include a tissue. The hyperspectral imaging system may display an unmixed color image of the tissue. The health condition may cause differentiation of chemical composition of the tissue. This chemical composition may be related to chemical compounds such as hemoglobin, melanin, a protein (e.g., collagen), oxygen water, the like, or a combination thereof. Due to the differentiation of the tissue's chemical composition, color of the tissue that is affected by the health condition may appear to be different than that of the tissue that is not affected by the health condition. Because of such color differentiation, the health condition of the tissue may be diagnosed. The hyperspectral imaging system may therefore allow a user to diagnose, for example, a skin condition, regardless of room lighting and skin pigmentation level.

For example, an illumination source radiation delivered to a biological tissue may undergo multiple scattering from inhomogeneity of biological structures and absorption by chemical compounds such as hemoglobin, melanin, and water present in the tissue as the electromagnetic radiation propagates through the tissue. For example, absorption, fluorescence, and scattering characteristics of the tissue may change during the progression of a disease. For example, therefore, the reflected, fluorescent, and transmitted light from tissue detected by the optical detector of the hyperspectral imaging of this disclosure may carry quantitative diagnostic information about tissue pathology.

The diagnostic information, obtained by using the hyperspectral imaging system, may determine the health condition of the tissue. As such, this diagnostic information may enhance a patient's clinical outcome, for example, before, during, and/or after surgery or treatment. This hyperspectral imaging system, for example, may be used to track a patient's evolution of health over time by determining the health condition of, for example, the tissue of the patient. In this disclosure, the patient may be any mammal. For example, the mammal may be a human.

The reference material disclosed above may be used in the diagnosis of the health condition.

The hyperspectral imaging system comprising Hyperspectral Phasors (HySP) may apply Fourier transform to convert all photons collected across spectrum into one point in the two dimensional (2D) phasor plot ("density plot"). The reduced dimensionality may perform well in low SNR regime compared to linear unmixing method, where each channel's error may contribute to the fitting result. In any imaging system, the number of photons emitted by a dye during a time interval may be a stochastic (Poissonian) process, where the signal (total digital counts) may scale as the average number of acquired photons, N; and the noise may scale as square-root of N, N. Such Poissonian noise of the fluorescence emission and the detector readout noise may become more significant at lower light levels. First, the error on HySP plots may be quantitatively assessed. Then, this information may be used to develop a noise reduction approach to demonstrate that the hyperspectral imaging system comprising HySP is a robust system for resolving time-lapse hyper-spectral fluorescent signals in vivo in a low SNR regime.

The following features are also within the scope of this disclosure.

Multispectral fluorescence microscopy may be combined with hyperspectral phasors and linear unmixing to create a Hybrid Unmixing (HyU) technique (HyU). In some examples, the dynamic imaging of multiple fluorescent labels in live, developing zebrafish embryos and mouse tissue may demonstrate the capabilities of HyU. HyU may be more sensitive to low light levels of fluorescence compared to conventional linear unmixing approaches, permitting better multiplexed volumetric imaging over time, with less bleaching. HyU may also simultaneously image both bright exogenous and dim endogenous labels because of its high dynamic range. This technique may allow interrogation of cellular behaviors, tagged components, and cell metabolism within the same specimen, offering a powerful window into the orchestrated complexity of biological systems.

Hybrid Unmixing (HyU) technique(s) may resolve many of the challenges that have limited the wider acceptance of HFI for applications for example, in vivo imaging. HyU may employ the phasor approach merged with traditional unmixing algorithms to untangle the fluorescent signals more rapidly and more accurately from multiple exogenous and endogenous labels.

The phasor approach, which is a dimensionality reduction approach for the analysis of both fluorescence lifetime and spectral image analysis, may provide advantages to HyU, including spectral compression, denoising, and computational reduction for both pre-processing and unmixing of HFI datasets.

A conventional phasor analysis may fully be supervised and may require a manual selection of regions or points on a graphical representation of the transformed spectra, called the phasor plot.

HyU, as discussed herein, may utilize phasor processing as an encoder to aggregate similar spectra and applies unmixing algorithms, such as LU, on the aggregate similar spectra to provide unsupervised analysis of the HFI data, thereby simplifying the data processing and removing user subjectivity.

HyU may offer, for example, three advantages over prior techniques: (1) improved unmixing over conventional LU, especially for low intensity images, e.g., down to 5 photons per spectra; (2) simplified identification of independent spectral components; and (3) dramatically faster processing of large datasets, overcoming the typical unmixing bottleneck for in vivo fluorescence microscopy.

HyU, as discussed herein, may combine the best features of hyperspectral phasor analysis and unmixing techniques, resulting in faster computation speeds and more reliable results, especially at low light levels.

In this disclosure, the (intensity) spectra may be unmixed by any technique. An example of the unmixing technique is linear unmixing (LU) technique. Examples of the unmixing techniques may include (1) fully constrained least squares, (2) matrix inversion, (3) non-negative matrix factorization, (4) geometric unmixing method, (5) Bayesian unmixing method, and (6) sparse unmixing method. For a review of such unmixing techniques, for example, see Jiaojiao Wei and and Xiaofei Wang "An Overview on Linear Unmixing of Hyperspectral Data," Mathematical Problems in Engineering, Volume 2020, Article ID 3735403, pages 1-12, https://doi.org/10.1155/2020/3735403. The entire content of this publication is incorporated herein by reference. Such unmixing techniques are within the scope of this disclosure.

Example 1. An Exemplary HyU

The phasor approaches of this disclosure may reduce the computational load because they are compressive, reducing, for example, the 32 channels of an HFI spectral plot into a position on a 2D-histogram, representing the real and imaginary Fourier components of the spectrum (FIGS. 1A,B). Different 32 channel spectra are represented as different positions on the 2D phasor plot, and mixtures of the two spectra will be rendered at a position along a line connecting the pure spectra.

Because the spectral content of an entire 2D or 3D image set is rendered on a single phasor plot, there is a dramatic data compression—from a spectrum for each voxel in an image set (for example, up to or even beyond gigavoxels) to a histogram value on the phasor plot (for example, megapixels).

In addition, because each "bin" on the phasor plot histogram corresponds to multiple voxels with highly similar spectral profiles, the binning itself represents spectral averaging, which reduces the Poisson and instrumental noise (FIGS. 1C-E).

Poisson noise in the collected light is unavoidable in HFI unless the excitation is turned so high that the statistics of collected fluorescence creates hundreds or thousands of photons per spectral bin. The clear separation of the spectral phasor plot and its referenced imaging data, permits denoising algorithms to be applied to phasor plots with minimal degradation of the image resolution.

LU or other unmixing approaches may be applied to the spectra on the phasor plot, offering a dramatic reduction in computational burden for large image data sets (FIG. 1D). To understand this saving, consider the conventional approach of LU applied to image data at the voxel level (FIGS. 1A,F). A timelapse volumetric dataset of 512×768×17 (x, y, z) pixels, over 6 timepoints, (Table 1), would, for example, may require 40 million operations. HyU's may require, for example, only ~18 thousand operations to unmix each bin on the phasor plot, representing, for example, more than a thousand-fold saving (FIGS. 1F,G).

Example 2. Advantage of HyU Over the Conventional LU

Figure 2:
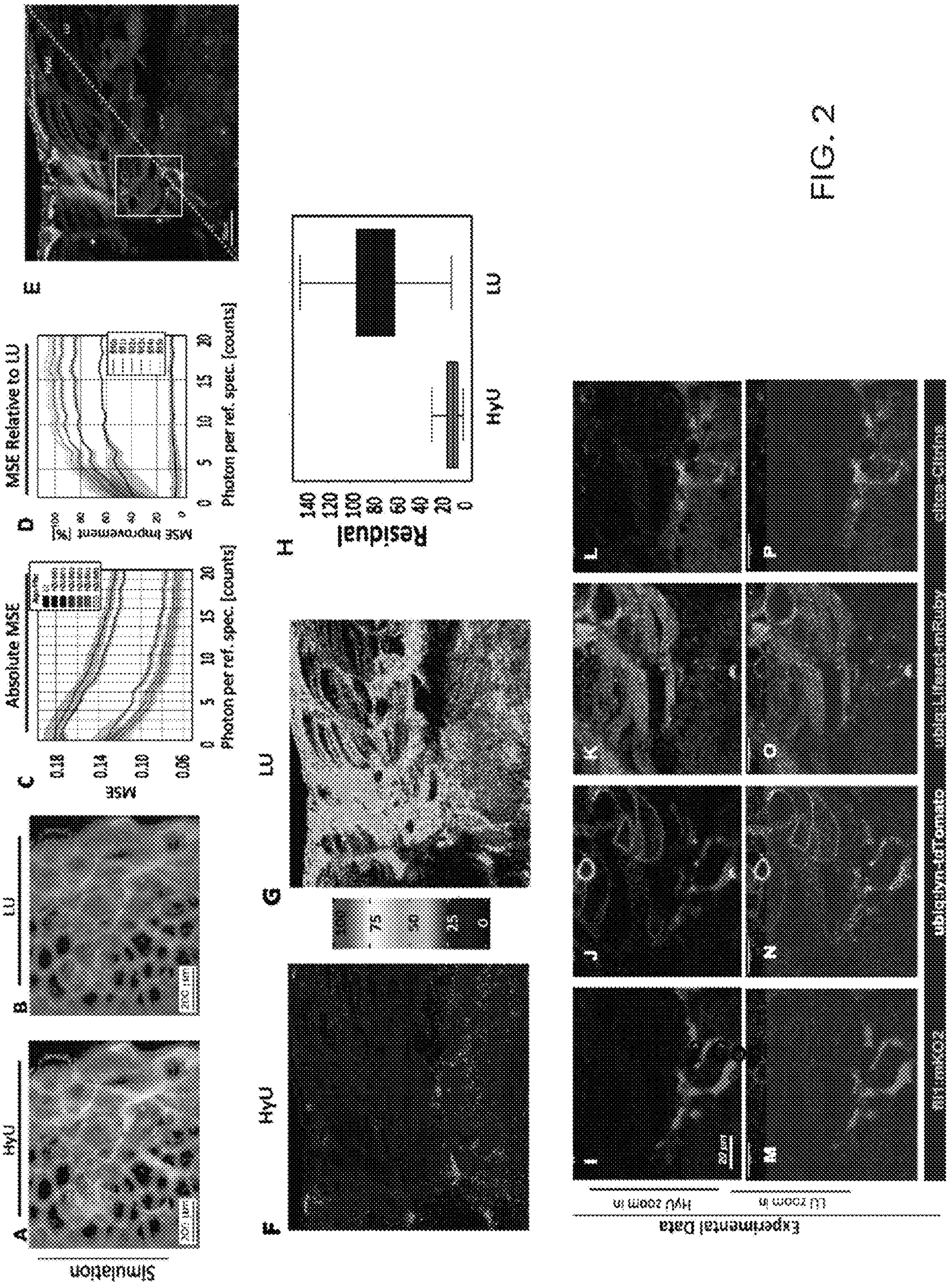
FIG. 2 illustrates that the systems and methods discussed herein, such as those describing Hybrid Unmixing (HyU), can outperform conventional Linear Unmixing (LU) in both synthetic and live spectral fluorescence imaging. In this example, (A) Hybrid Unmixing (HyU) and (B) Linear Unmixing (LU) tested using a hyperspectral fluorescence simulation that was generated from four fluorescent signatures (emission spectra, FIG. 11E). (C) Absolute Mean Squared Error (MSE) shows that HyU may offer a consistent reduction in error across a broad range of photons per spectra (#photons/independent spectral components, here resulting from 4 reference spectra combined). (D) The performance differences in the MSE of HyU relative to LU persists when applying multiple phasor denoising filters (0 to 5 median filters). The analysis of this synthetic data shows the consistent improvement of HyU at low photon counts with over a 2-fold improvement when 5 denoising filters are applied at a signal level of 16 photons per spectrum. Shaded regions for line plots denote the 95% confidence interval around the mean. (E) Unmixing of experimental data from a 4-color zebrafish shows increased contrast for HyU (left) compared to LU (right). Scale bar=50 μm. (F, G) The increased accuracy is revealed by residual images of HyU and LU, showing the spatial distribution of unassigned signals after the analysis of data in E. The results show consistently lower residual values for HyU (F) compared to LU (G). (H) Box plots of the residuals in F and G presents values of 11% for HyU compared to 77% for LU with *($p<10^{-10}$) with $n=1.05\times10^6$ pixels. Center: Median; Box: First/Third Quartile; Whiskers: 1.5× first, third quartiles; Min/max not shown. (I-L) Enlarged rendering of HyU results (E, white box) clearly shows low levels of bleed-through between labels (M-P) Similar enlargement of LU results show noticeably worse performance. Note that regions with bright signals (membrane J, N white arrow) bleed through other channels (M) and (O). Scale bar: 20 μm. Tetra-labeled specimen used in this example was Gt(cltca-citrine);Tg(ubiq:lyn-tdTomato; ubiq:Lifeact-mRuby;fli1:mKO2).
Figure 9:
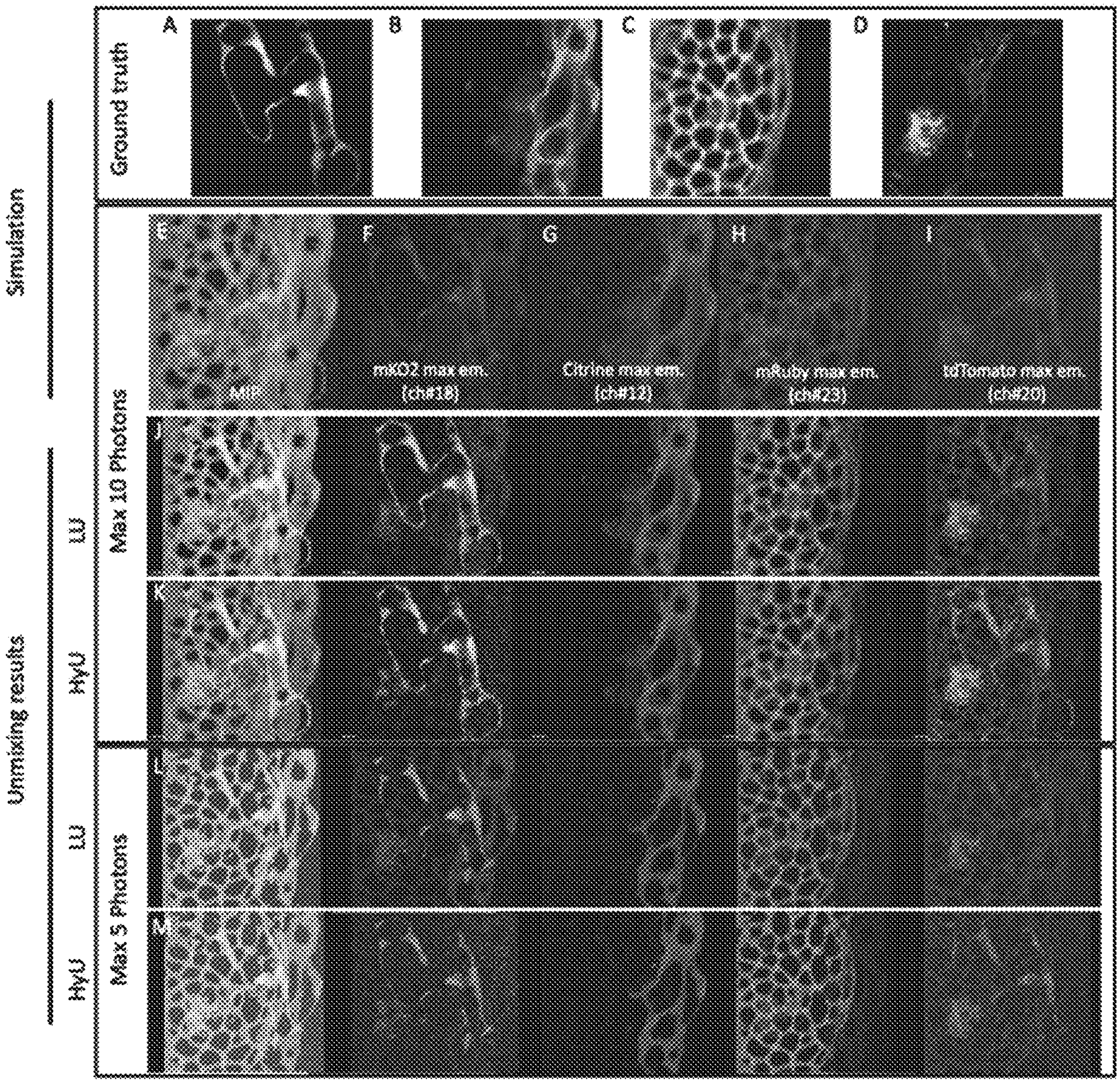
FIG. 9 illustrates a comparison of unmixing results for synthetic data at different SNR which may demonstrate improved HyU performance. Ground truth photon mask of the four independent fluorescent signals, (A) mKO2, (B) Citrine, (C) mRuby, and (D) tdTomato for synthetic data. (E) The maximum intensity projection (MIP) of the simulated 32 channel hyperspectral image generated from the four ground truth masks at low signal-to-noise ratio (SNR). In this case, a maximum of 10 photons are simulated for each fluorescent component. (F-I) Grayscale representation of the maximum emission channel of each component, based on the respective spectra. Unmixing result of (J) LU and (K) HyU for simulations with a maximum of 10, report decreased performance. In the ultra-low SNR simulation (5 photon at most for each component), both LU (I) and HyU (M) results are deteriorated, however HyU maintains a 1.5× lower average MSE compared to LU.
Figure 10:
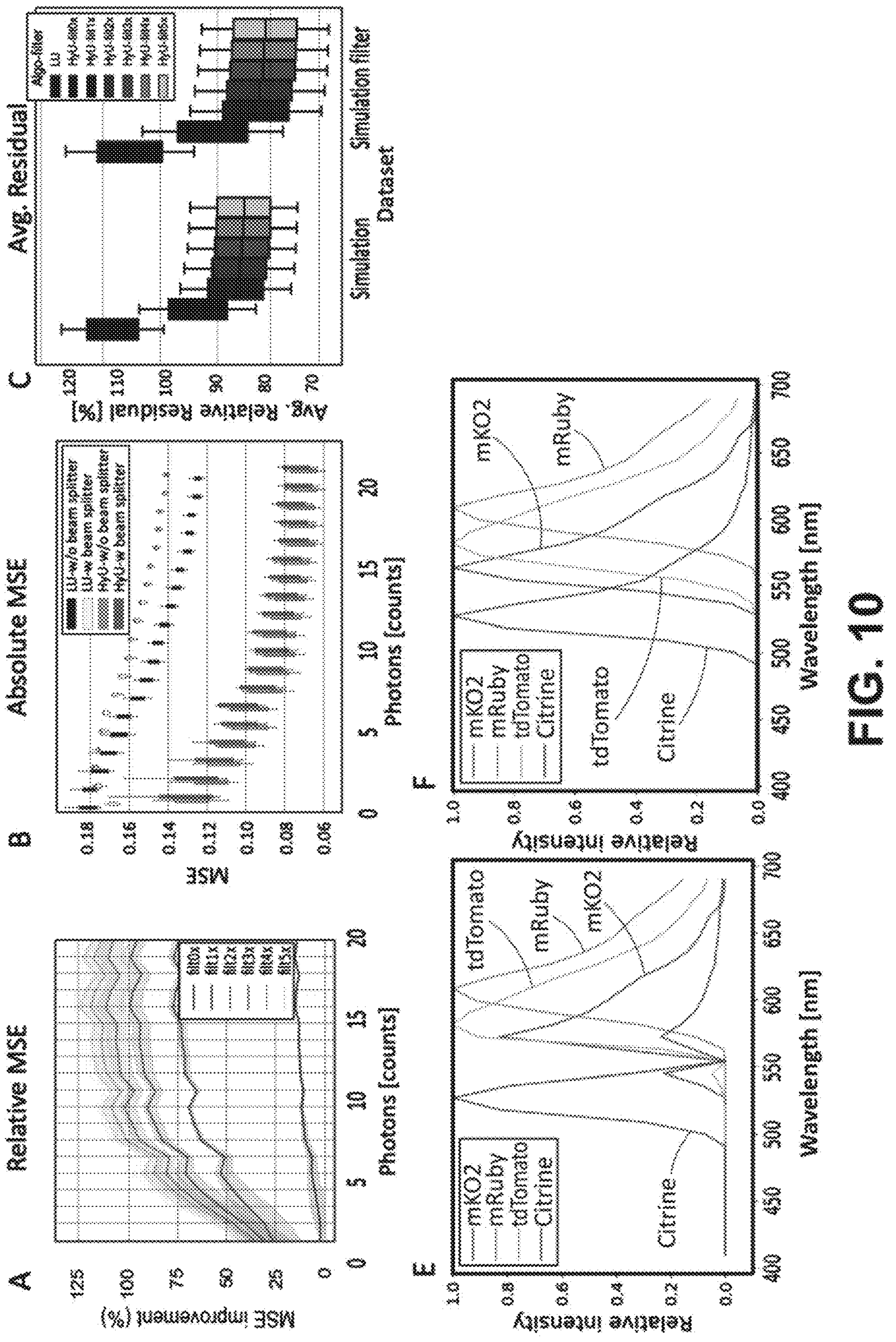
FIG. 10 illustrates a quantification of HyU vs LU unmixing results for synthetic data which highlight increased HyU performance. HyU performance is evaluated under several algorithmic parameters and experimental conditions. (A) Relative MSE between HyU and LU was calculated as a function of max input photons/spectrum over 5 denoising filters for HyU. The improvement increases both with the number of photons and the number of denoising filters, showing significant differences above 7 photons/spectra with peak at 124%. Shaded regions denote the 95% confidence interval around the mean. (B) Absolute MSE from LU and HyU algorithms for the same synthetic dataset with and without beam splitters. The addition of optical filters causes the MSE of LU to increase on average by 8%, compared to an average increase of 5% for HyU. N=1.05 e6 pixels. Center: Median; Box: First/Third Quartile; Whiskers: 1.5× first, third quartiles; Min/max not shown. (C) Average relative residual of synthetic data with and without beam splitters with increasing level of denoising. The average relative residual without beam splitters with denoising (HyU-filt1×-HyU-filt5×) is 83%, compared to 109% for LU. In the absence of denoising filters (filt0×) the average relative residual is 92.9%. Beam splitters were applied in this simulation and both Mean Squared Error (MSE) and residual values were calculated with and without beam splitters. N=1.05 e6 pixels. Center: Median; Box: First/Third Quartile; Whiskers: 1.5× first, third quartiles; Min/max not shown. (D) Simulated spectral with beam splitter and (E) simulated spectral without beam splitter are shown.
Figure 11:
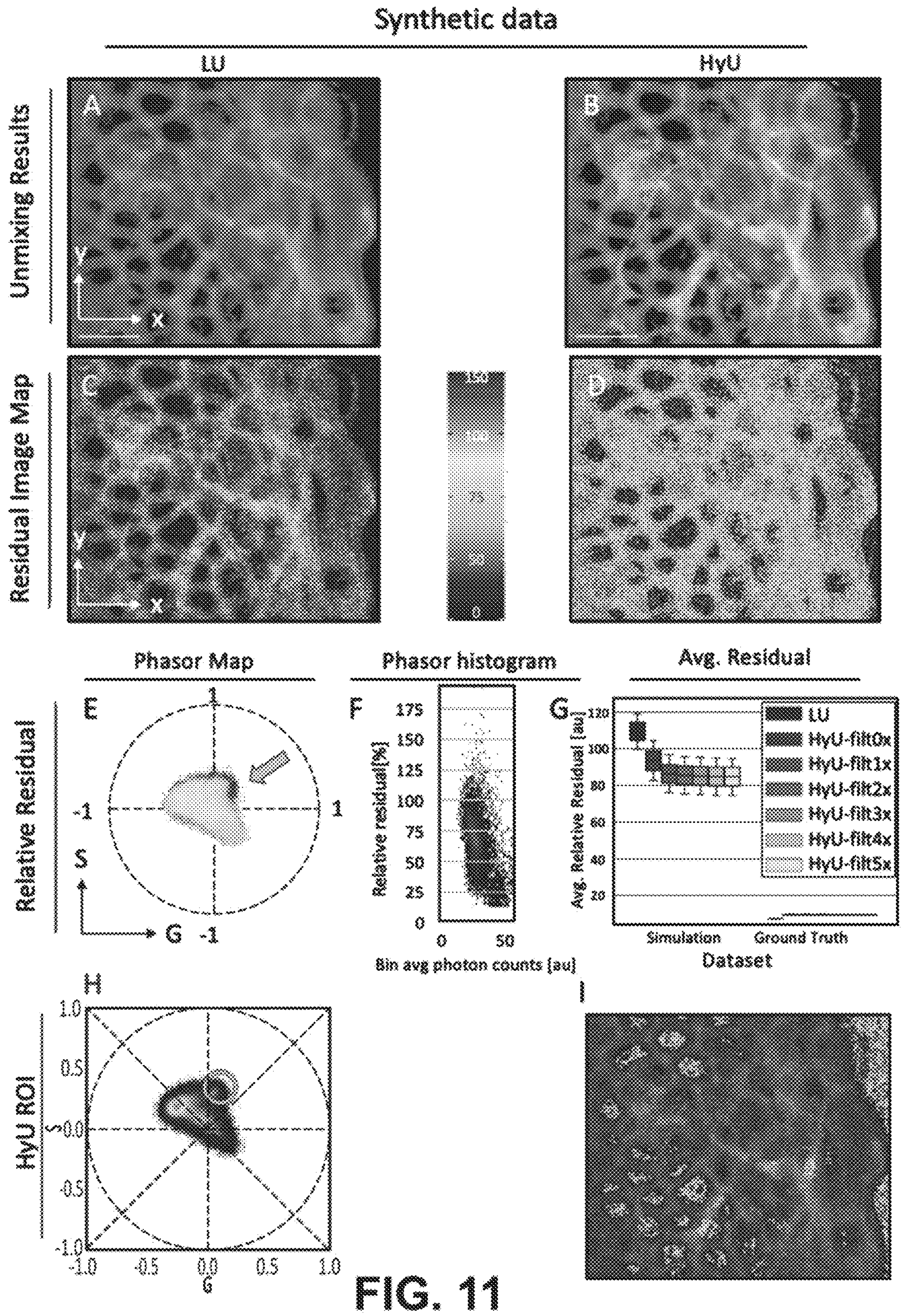
FIG. 11 illustrates a residual analysis for synthetic data which can identified locations with reduced algorithm performance. Simulated data in FIG. 2 for four fluorescent labels (Citrine, mKO2, tdTomato, mRuby) is analyzed with LU and HyU. Unmixing results for (A) HyU and (B)LU. Residual Image Map for (C) HyU and (D) LU results presents regions with higher residual (red) along the boundary between the sample's labelled features and the background, where signal-to-noise drops. The average residual values for LU (118%) are higher than HyU (94%). (E) Residual Phasor Map shows higher residual for the background region (arrow), consistently with the results in C, D. The Jet colorbar scale corresponds to C, D and E. (F) Phasor Residual Intensity Histogram maps the average photon counts in each histogram bin in E between 0 and 50 photons and presents a trend of decreasing relative residuals with photon number. The (G) Average Relative Residual plot shows higher values for LU compared to HyU with different denoising filters applied. Ground truth values are also included for comparison. N=1.05 e6 pixels. Center: Median; Box: First/Third Quartile; Whiskers: 1.5× first, third quartiles; Min/max not shown. An (H) original phasor plot with 0 threshold and 5 denoising filters applied is presented. The ROI (yellow circle) highlights the background pixels in yellow in the (I) average spectral intensity image. The noise from background and residual can be decreased considerably with an intensity threshold.
Figure 12:
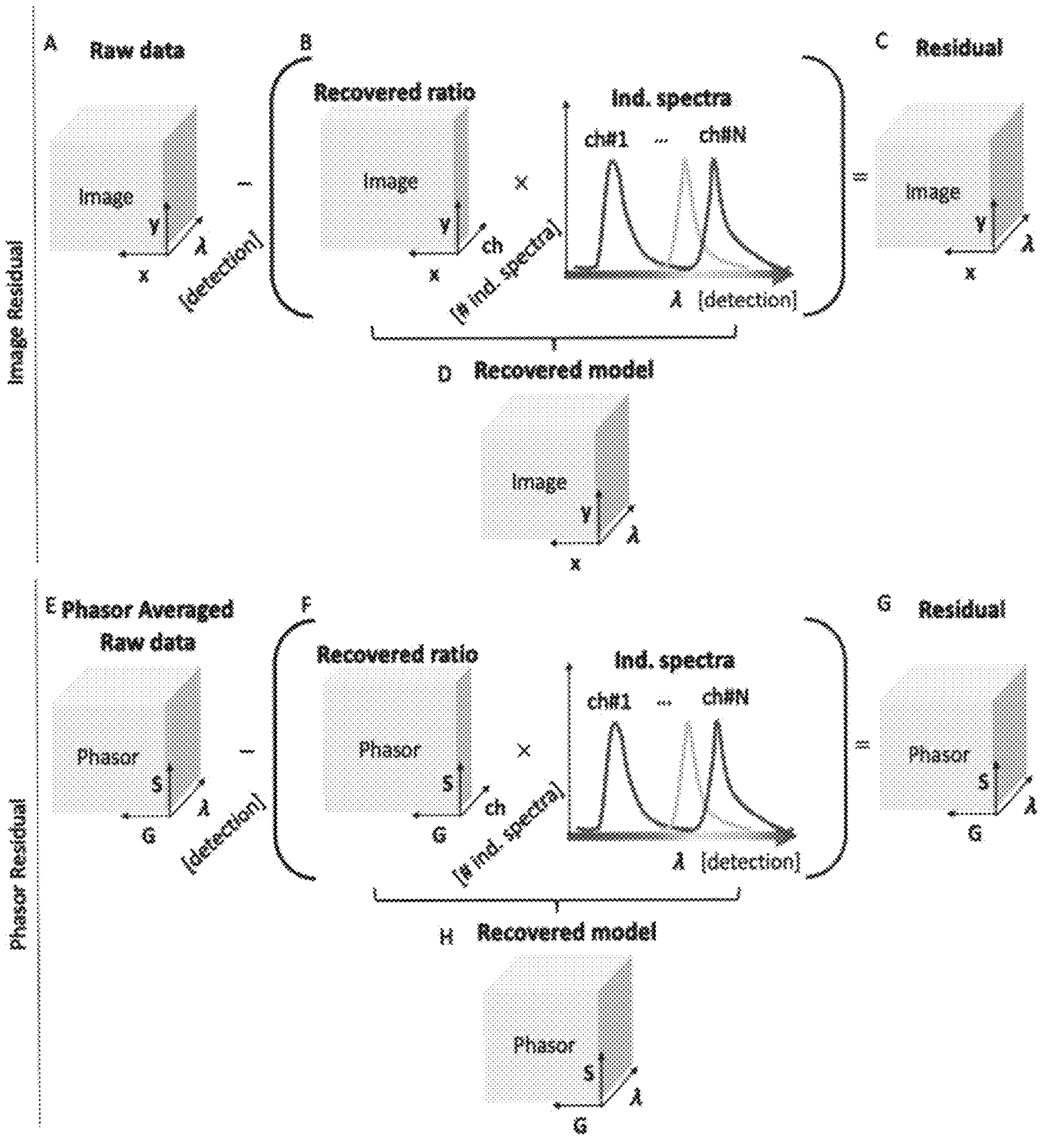
FIG. 12 illustrates a schematic overview of residual calculation. Image residual is the residual for image (x, y). (A) Raw hyperspectral data cube in dimension of (x, y, λ). x,y is the spatial dimension. λ is the wavelength range from the spectral channel on the detector. (D) Recovered model in dimension of (x, y, λ) comes from (B) the product of Recover ratio (x,y, ch) and Independent spectra (ch, λ). ch is the number of independent spectra or unmixing component. (C) Residual is the difference of Recovered model and Raw data. (E-H) Same logic for Phasor residual, but instead of (x, y) the dimension of Phasor is composed from the real and imaginary Fourier components (G, S).

In this example, to quantitatively assess the relative performance of HyU and the conventional LU, they were analyzed on synthetic hyperspectral fluorescent datasets, created by computationally modelling the biophysics of fluorescence spectral emission and microscope performance (FIGS. 2 A, B, and FIGS. 9-11). A synthetic dataset was used to evaluate LU and HyU algorithm performance quantitatively by using metrics such as Mean Square Error (MSE) and unmixing residual (see FIG. 12 for both metrics, a lower value indicates better performance).

In addition to the computational efficiency mentioned above, HyU analysis shows better ability to capture spatial features over a wide dynamic range of intensities, when compared with conventional LU, in large part due to the denoising created by processing in phasor space (FIGS. 2 A, B). The improved accuracy is demonstrated by a lower MSE, in comparing the results of HyU with the conventional LU to the image ground truth.

The absolute MSE for HyU can be consistently up to 2× lower than that of the conventional LU, especially at low and ultra-low fluorescence levels (FIG. 2C). MSE may be further decreased by the use of denoising filters on the phasor plot, resulting in superiority of HyU relative to the conventional LU for HFI at low (5-20 photons/spectrum) and ultralow (2-5 photons/spectrum) levels (FIG. 2D).

To better characterize the performance in the experimental data without ground truth, the unmixing residual can be defined as the difference between the original multichannel hyperspectral images and their unmixed results. Residuals provide a measure of how closely the unmixed results reconstruct the original signal (FIG. 9). Unmixing residuals are inversely proportional to the performance of the algorithm, with low residuals indicating high similarity between the unmixed and the original signals. Analysis of unmixing residuals in the synthetic data highlights an improved interpretation of the spectral information in HyU with an average unmixing residual reduction of 21% compared to the standard (FIG. 11C). The reduction in both MSE and average unmixing residual for synthetic data demonstrates the superior performance of HyU over the conventional LU, and provides a baseline comparison when demonstrating performance improvements for experimental data.

Analysis of experimental data, which reveals comparatively lower unmixing residuals and a higher dynamic range as compared to the conventional LU, supports the enhanced performance of HyU. Data was acquired from a quadra-transgenic zebrafish embryo Tg(ubiq:Lifeact-mRuby);Gt(cltca-citrine);Tg(ubiq:lyn-tdTomato);Tg(fli1:mKO2), labelling actin, clathrin, plasma membrane, and pan-endothelial cells, respectively (FIGS. 2E-L, 3, and FIGS. 13-15).

HyU unmixing of the data shows minimal signal cross-talk between channels while the conventional LU presents noticeable bleed-through (FIG. 2M-P). Consistently with synthetic data, the unmixing residual can be utilized as the main indicator for quality of the analysis in experimental data, owing to the absence of a ground truth.

Figure 13:
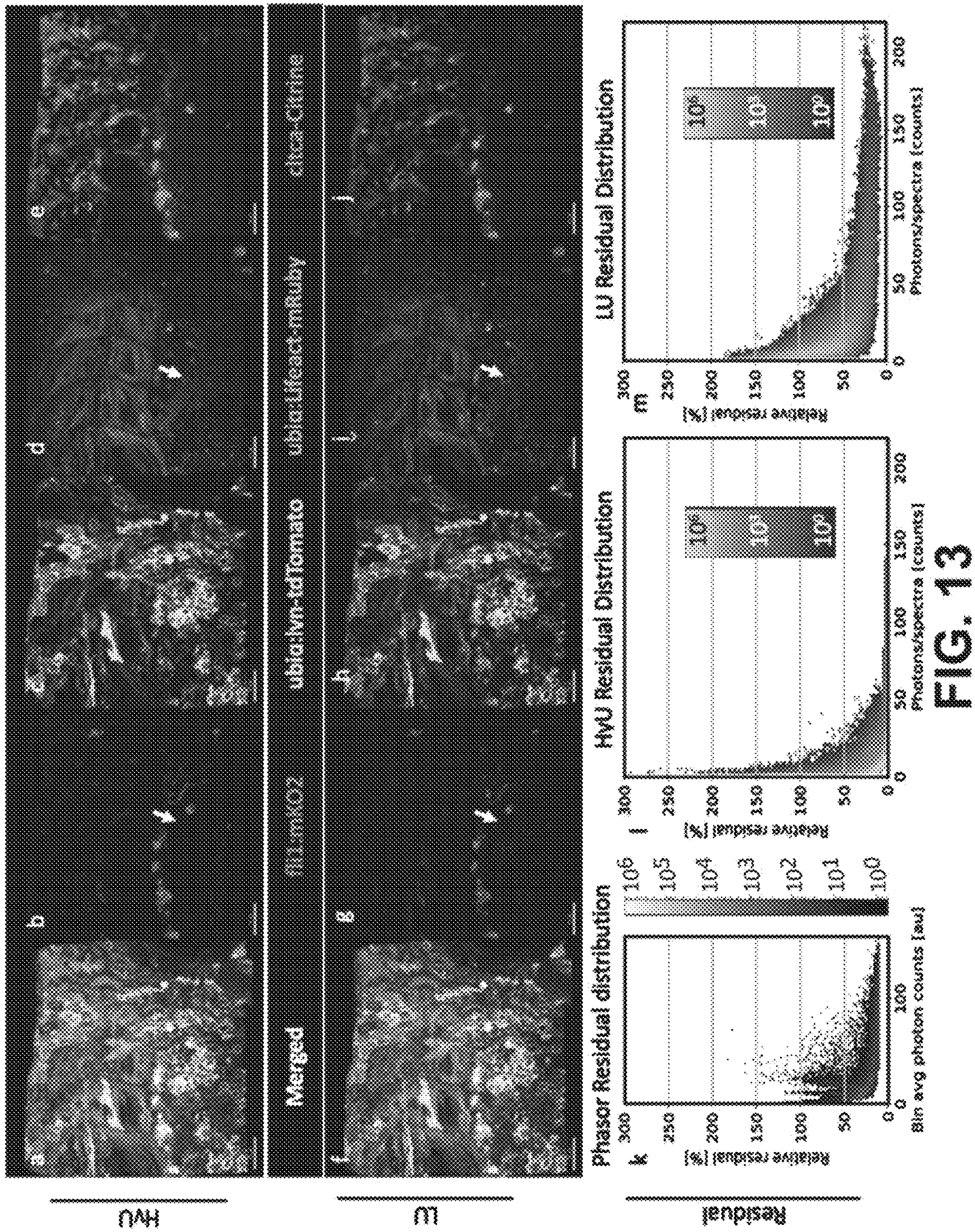
FIG. 13 illustrates an example unmixing of a quadra-transgenic zebrafish with HyU and LU which highlights improvements in contrast and spatial features. Volumetric zoom-in view of the somites within the trunk region of a 10-dpf Gt(cltca-citrine);Tg(ubiq:lyn-tdTomato;ubiq:Lifeact-mRuby;fli1:mKO2) zebrafish merging all channels in (A) HyU and (B) LU. (A-E) HyU presents a wide dynamic range of intensities with average contrast 1.11-fold higher than LU compared to (F-J) LU. In LU, bleed-through from the (H) membrane label (arrow) is observed in the (G) lymphatic vasculature channel (arrow) and the (I) actin channel (arrow). This incorrect re-assignment of intensities is not present in the corresponding HyU channels for (B) vasculature and (D) actin, where fibers (arrow) are cleanly unmixed. (K) Phasor Residual Distribution shows the distribution of relative residual (%) and photon counts in phasor histogram bins. Residual distribution shows the distribution of relative residual (%) and photon counts in histogram pixels for both (L) HyU and (M) LU.

The residual images (FIGS. 2F, G) depict a striking difference in performance between HyU and the conventional LU. The average relative residual of HyU denotes a 7-fold improvement compared to the conventional LU (FIG. 2H) in disentangling the fluorescent spectra. The unmixed channels can be viewed independently (FIGS. 2,I to L), zooming in on details (FIGS. 2,I to P) to highlight areas affected by bleed-through and which are difficult to unmix. HyU, with contrast 2-fold higher than the conventional LU, reduces bleed-through effects and produces images with sharper spatial features, leading to better interpretation of the experimental data (FIGS. 2 K, L, and FIG. 13).

Figure 3:
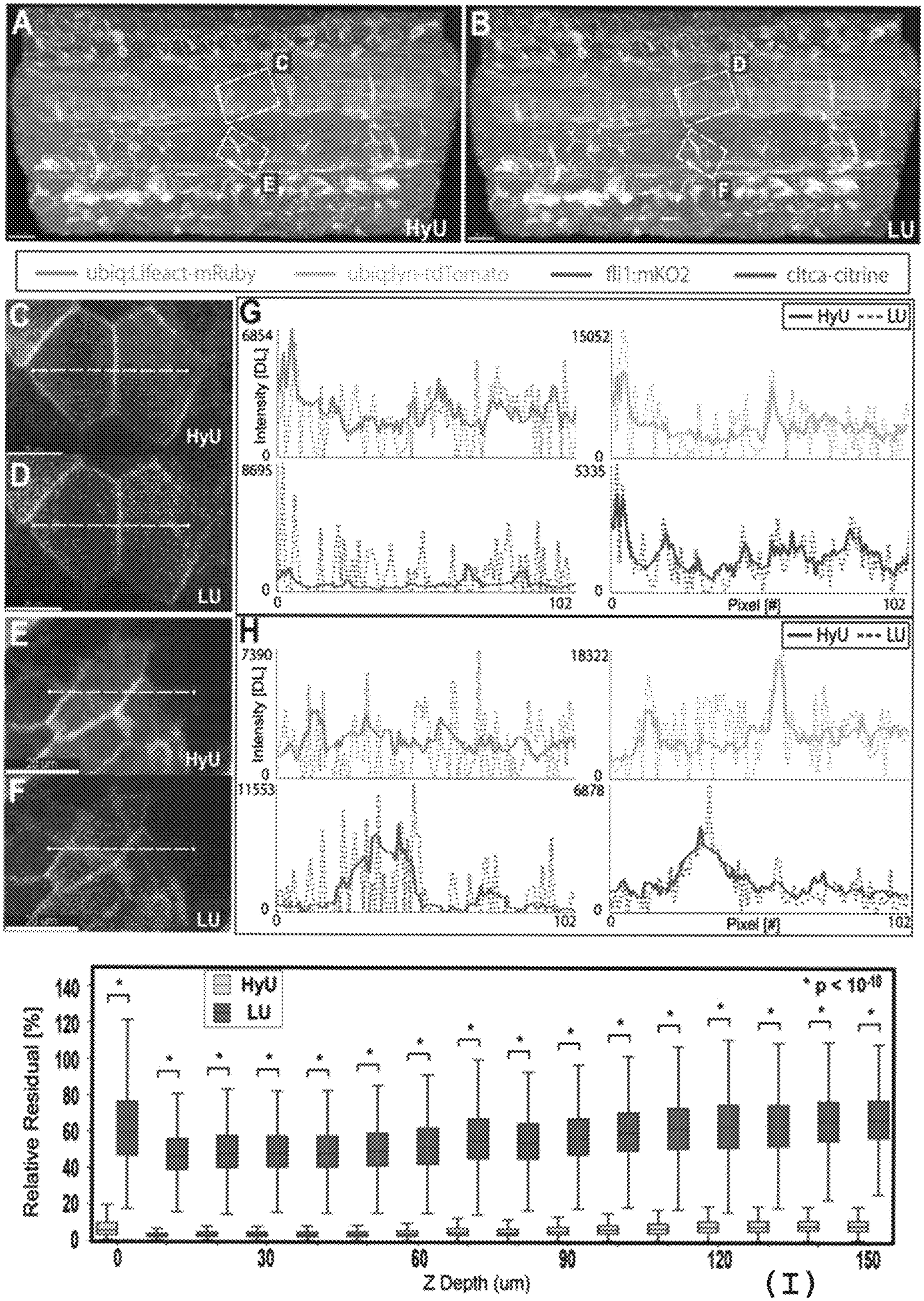
FIG. 3 illustrates that the systems and methods discussed herein, such as those describing Hybrid Unmixing (HyU) may enhance unmixing for low-signal in vivo multiplexing and achieves deeper volumetric imaging. In this example, (A) Hybrid Unmixing (HyU) volumetric renderings compared to those of (B) Linear Unmixing (LU) for the trunk portion in a 4-color zebrafish demonstrate an increased contrast and reduced residual in HyU results, especially over deeper parts of the sample. The 4 labels in the fish are Gt(cltca-citrine);Tg(ubiq:lyn-tdTomato;ubiq:Lifeact-mRuby;fli1:mKO2), respectively labeling clathrin-coated pits (green), membrane (yellow), actin (cyan) and endothelial (magenta). (C,E) HyU results have increased spatial resolution and less bleed though comparing to those of (D,F) LU. Scale bar: 20 μm. When observing the zoomed-in visualization of the surface region of the sample, the yellow signal distinctly marks the membrane and the cyan signal clearly labels the actin in (C) HyU. The same signals are not distinct in (D) LU because of multiple incorrectly assigned magenta pixels that bleed through compromising the true signal in other channels. Similarly, for the zoomed-in visualization of the Perivascular region of the embryo, in (E) HyU, the yellow and magenta signals clearly distinguish the membrane and vasculature while in (F) LU, the results are corrupted by greater noise. (G,H) Intensity line plots of each of the four results signals for HyU (solid) and LU (dashed) demonstrate the improved profiles with greatly reduced noise peaks in HyU as compared to LU. Intensities are scaled by the maximum of each unmixed channel. DL: digital level. (I) Box plots of the relative residual values as a function of z depth for HyU and LU highlight the improvements in the unmixing results. HyU has an unmixing residual of 6.6%±5.3% compared to LU's 58%±17%. The average amount of residual is 9-fold lower in HyU with narrower variance of residual. $n=5.2\times10^5$ pixels for each z slice. Center: Median; Box: First/Third Quartile; Whiskers: 1.5× first, third quartiles; Min/max not shown.
Figure 14:
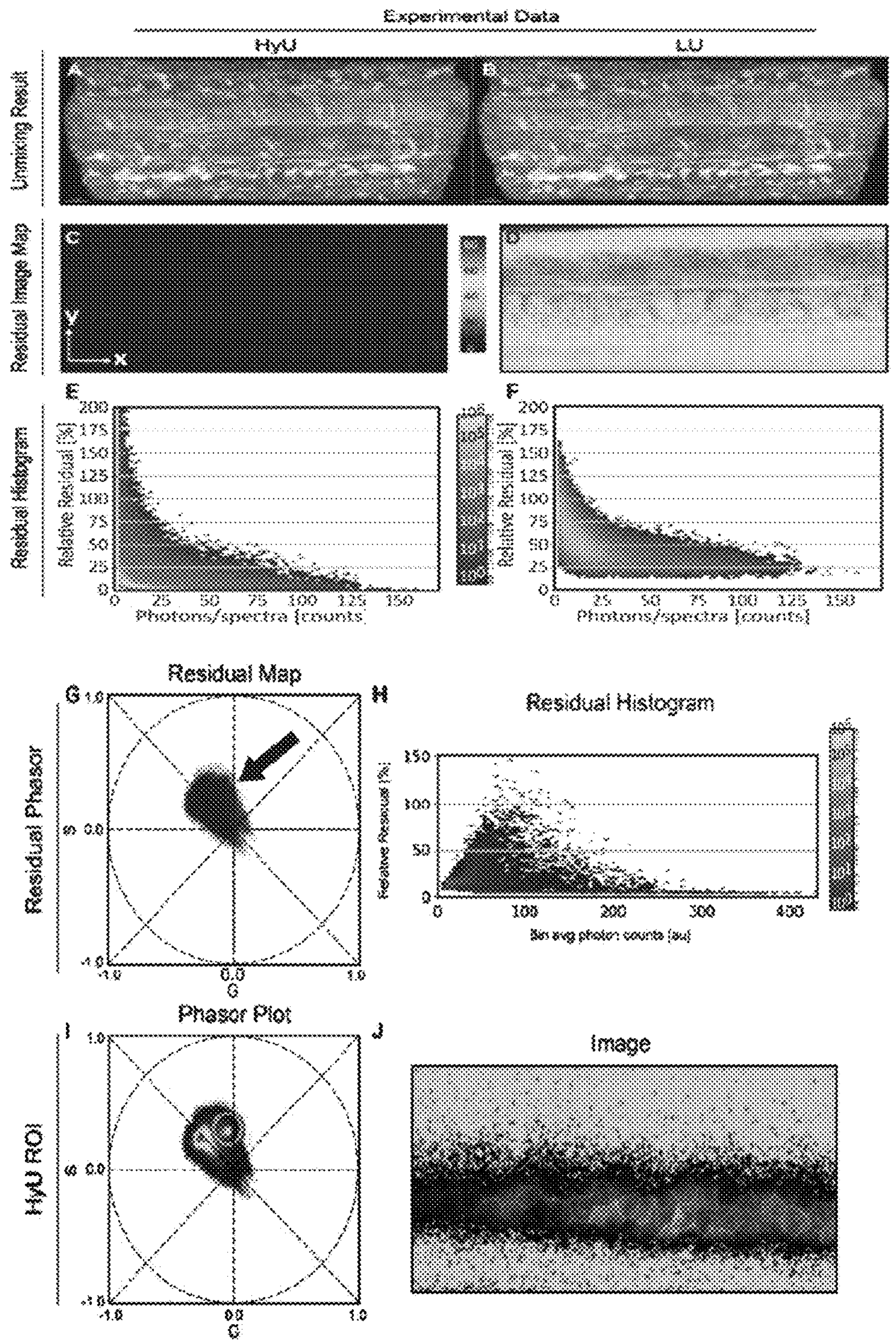
FIG. 14 illustrates residual analysis of experimental data which supports performance improvement of HyU. Residual analysis for multispectral fluorescent data of a 5 dpf quadra-transgenic zebrafish Gt((cltca-citrine);Tg (ubq:lyn-tdTomato);(ubiq:Lifeact-mRuby);(fli1:mKO2)) in FIG. 3. Unmixing results for (A) HyU and (B) LU, respectively. Residual Image map of the z-averaged dataset for (C) HyU and (D) LU show lower residual values for HyU, suggesting improved quality of unmixing. (E) Residual distribution relative to the original intensity in each pixel as a function of estimated photon counts per spectrum for LU and (F) HyU. (G) Residual Phasor Map presents increased residual values in the background region (arrow). Jet colormap scale refers to C, D and G. (H) Residual Phasor Histogram for HyU shows distribution of residuals in the broad dynamic range of photons for experimental data. (I) Raw phasor with 0 threshold applied and 5 denoising filters, the ROI (yellow circle) highlights the background pixels in the (J) average spectral image (showing the first z slice).
Figure 15:
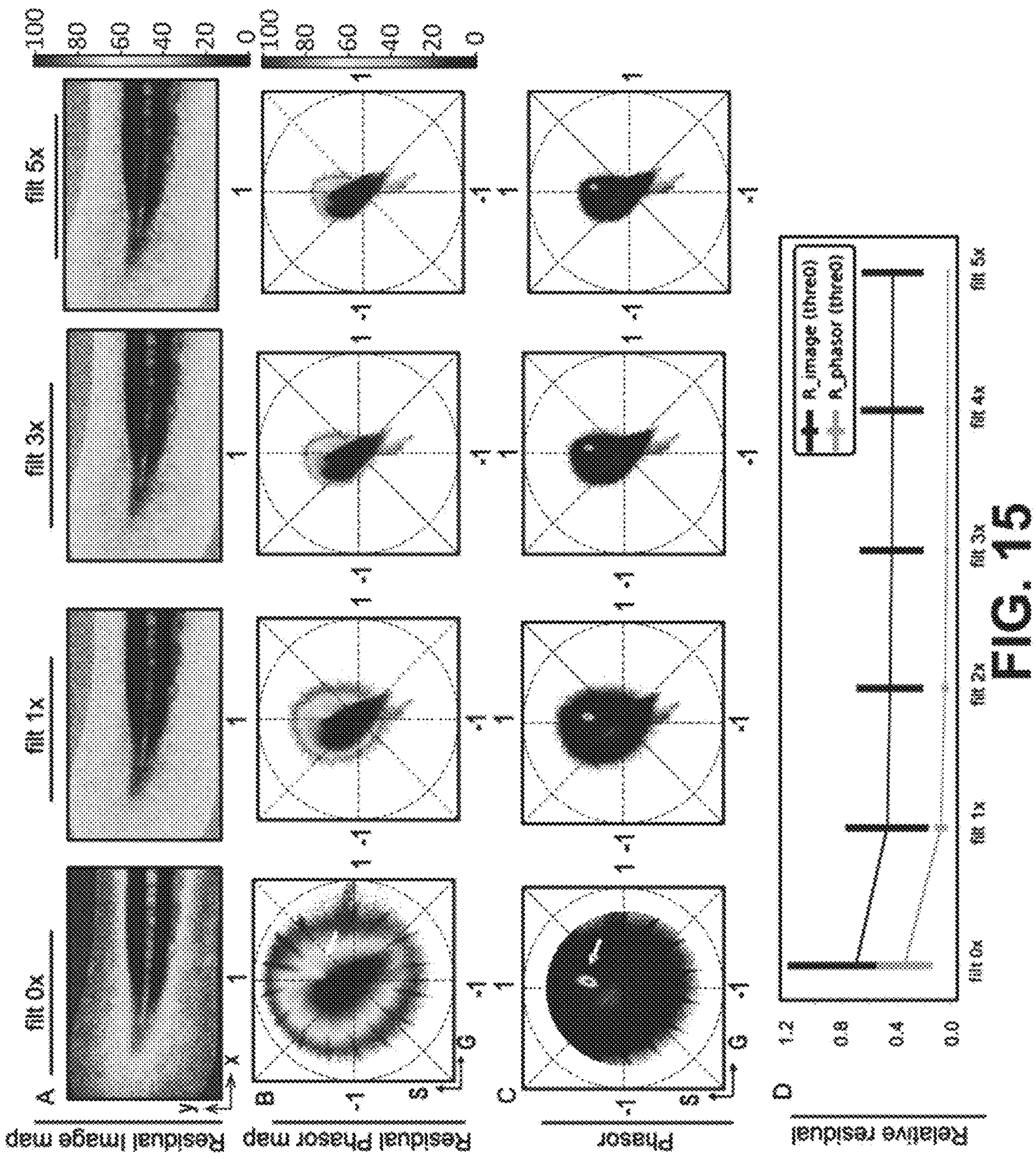
FIG. 15 illustrates an application of denoising filters which reveals improved results with lower residuals. (A) Residual Image Map of HyU unmixing of a quadra-transgenic zebrafish Gt(cltca-citrine);Tg(ubiq:lyn-tdTomato; ubiq:Lifeact-mRuby;fli1:mKO2) inclusive of one strong autofluorescent signal. Residual values are calculated with different number of denoising filters[8]. The average relative residual visibly decreases with the increase of denoising filter numbers. (B) Residual Phasor Map shows a major decrease in values between 0 and 1 denoising filters, maintaining statistically similar values at higher denoising filter applications. (C) Phasor plots for different denoising filters. Phasor of raw data prior to denoising or thresholding, presents noise connected to each of the detectors, as well as a high count area corresponding to the background region. The phasor plot distribution highlights areas with higher pixel counts coming from the background noise, which correspond with lower Residual Phasor Map values in B. (D) Average residual values for Residual Image Map (A) and Residual Phasor Map (B) highlight that the improvement on residuals mostly focuses on the first application of the denoising filter. In this initial denoising, the average relative residual decreased from 69.8% to 46.8%, further decreasing to 42.6% after 5 denoising. Average relative residual for phasor decreased from 33.9% to 7.1% after 1 denoising filter was applied, further decreasing to 2.1% after 5 denoising applied. With standard processing threshold of 250 digital levels applied (bottom 0.38% intensities of 16-bit format), the average relative residual decreased from 7.2% to 4.6%, further decreasing to 4.1% after 5 denoising filters. Average relative residual for phasor decreases from 10.1% to 2.6%, further decreasing to 1.1% after 5 denoising filters. Bars denote the variance of the relative residual values.
Figure 16:
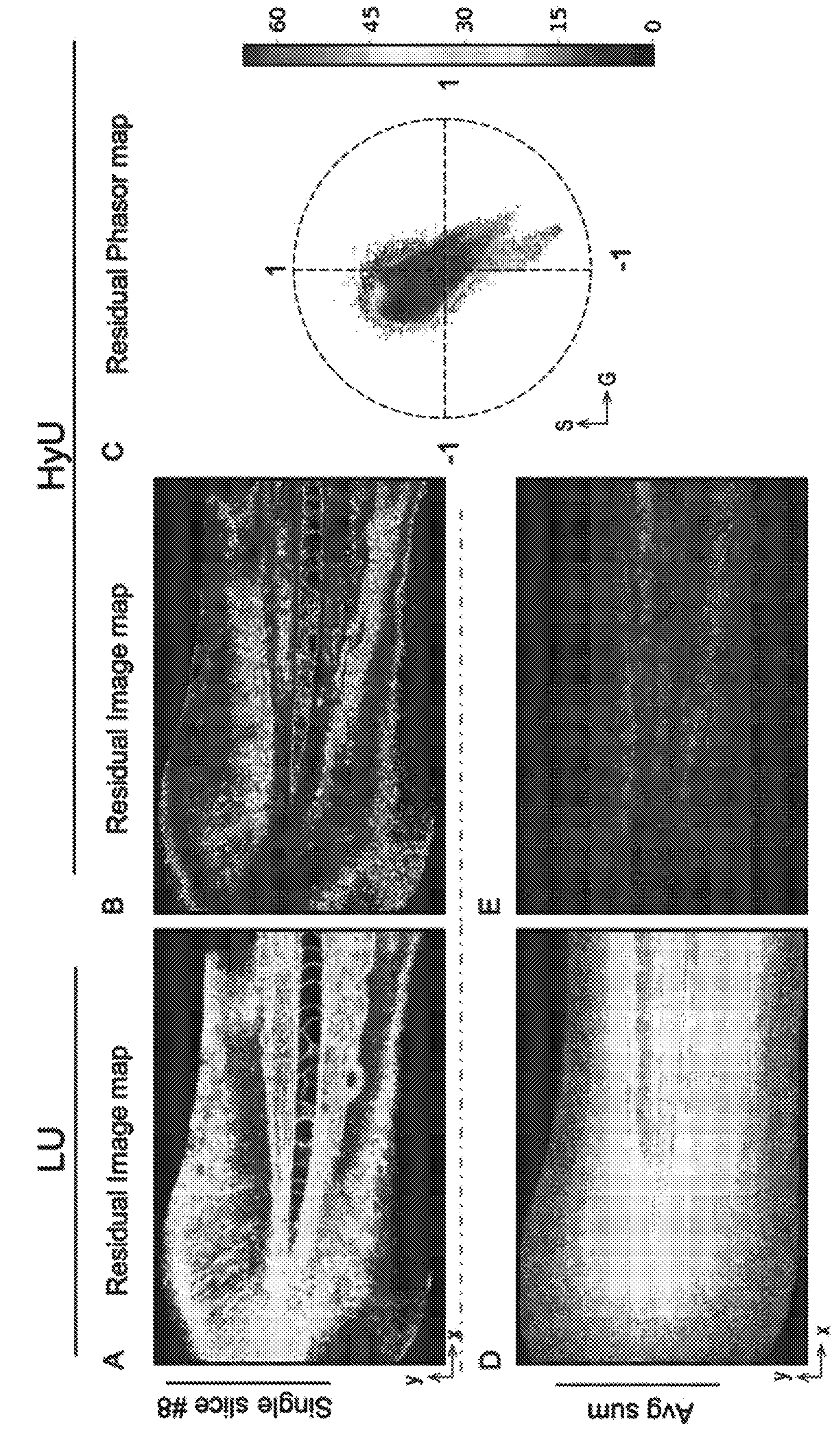
FIG. 16 illustrates a comparison of residual images for LU and HyU which highlights improved HyU performance. Residual Image projection for LU and HyU of a 3D dataset of 3 dfp quadra-transgenic zebrafish Gt(cltca-citrine);Tg (ubiq:lyn-tdTomato; ubiq:Lifeact-mRuby;fli1:mKO2) with an intensity threshold of 250. (A) LU Residual Image Map for a single slice (z=8 of 17 in a z-stack) provides average relative residual of 35.9%, while the (B) corresponding map for HyU averages at 7.1%. (C) Residual Phasor Map for the z-stack presents average relative residual of 1.1%. The reduction in residuals for HyU is maintained across the z-stack, as shown in (D) the average LU and (E) HyU Residual Image Maps built from the average of residuals across all z-slices. The average residual improvement for HyU at 4% compared to LU at 21% is 5.3-fold.

Applying HyU to another HFI dataset further highlights HyU's improvements in noise reduction and reconstitution of spatial features for low-photon unmixing. (FIGS. 3, 14). In the zoomed-in image of a single slice of the embryo skin surface, acquired in the trunk region, the HyU image correctly does not display pan-endothelial (magenta) signal in the periderm, an area which should be devoid of endothelial cells and mKO2 signal (FIG. 3C). In contrast, the result from the conventional LU shows visually distinctive pan-endothelial signal throughout the tissue plane (FIG. 3D). This incorrect estimation of the relative contribution of mKO2 fluorescence for the conventional LU is possibly due to the presence of noise, corrupting the spectral profiles. This is further delineated in the intensity profiles of the mKO2 signal between HyU and LU with much higher individual peaks from noise demonstrated for LU (FIG. 3G, lower left). Intensity profiles for both magnified cross-sections of the volume (FIGS. 3C-F) provide a striking visualization of the improvements of HyU. The line intensity profiles in HyU present reduced noise and represent more closely the expected distribution of signals (FIGS. 3G,H). The visible micro patterns of actin on the membrane of the periderm suggest that the improvements quantified with synthetic data are maintained in live samples' signals and geometrical patterns of microridges. By contrast, noise corruption and the presence of misplaced signals are characterized in the results from the conventional LU, with high frequency intensity variations that mis-match both the labeling and biological patterns.

HyU is more accurate, leading to more reliable unmixing results across the depth of sample with greatly reduced unmixing residuals. The average residual for HyU is 9-fold lower than that of the conventional LU with a 3-fold narrower variance. (FIGS. 3I, 14). This reduction in the residual is consistent with increasing z-depth where HyU unmixing results stably maintain both lower residuals and variance on average. These reduced residuals correspond both to a mathematically more precise and more uniform decomposition of signals as illustrated by the distribution of residuals versus photons (FIGS. 14E,F, 20).

HyU's increased sensitivity can be utilized to overcome common challenges of multiplexed imaging such as poor photon yield and spectral cross-talk and were able to visualize dynamics in a developing zebrafish embryo, such as a triple-transgenic zebrafish embryo with labeled pan-endothelial cells, vasculature, and clathrin-coated pits (Tg(fli1:

mKO2); Tg(kdrl:mCherry); Gt(cltca-Citrine)). Multiplexing these spectrally close fluorescent proteins is enabled by HyU's increased sensitivity at lower photon counts.

Figure 4:
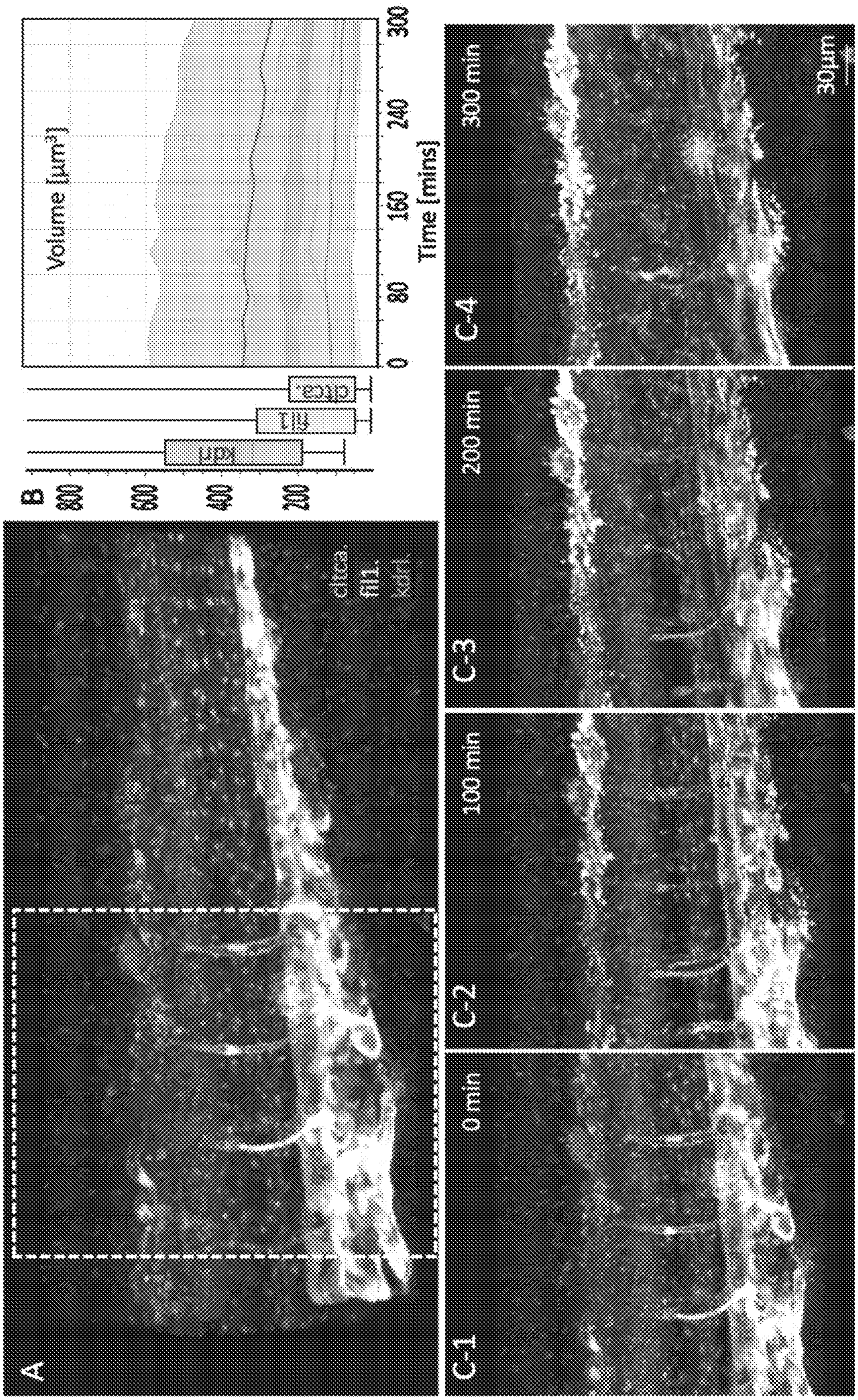
FIG. 4 illustrates that the systems and methods discussed herein, such as those describing HyU may reveal the dynamics of developing vasculature by enabling multiplexed volumetric time-lapse. Hybrid Unmixing (HyU) may overcome challenges in performing multiplexed volumetric time-lapse in vivo imaging of a developing embryo. This example illustrates (A) HyU rendering for the trunk portion of a 3-color zebrafish Gt(cltca-citrine);Tg(kdrl:mCherry;fli1:mKO2) at timepoint 0. (B) HyU unmixed results allow for quantitative analysis and segmentation, here an example representing the time evolution of the segmented volumes of mCherry (vasculature, magenta) mKO2(endothelial-lymphatics, yellow) and citrine (clathrin-coated pits, cyan). Box and line plots were generated using ImarisVantage as described in Methods. (C1-4) Time lapse imaging of the formation of the vasculature over 300 mins (zoomed-in rendering of the box in A) at 0, 100, 200, 300 minutes. This example show that HyU may provide good unmixing at low light levels to permit multiplexing to be used in the observation of development of a live embryo.

The increased performance at lower SNR allowed us to maintain high quality results (FIG. 4) while performing faster acquisitions and reducing photon-damage through lower excitation laser power and pixel dwell time. Decreased experimental requirements allow for tiling of larger volumes, extending the field-of-view while still providing enough time resolution for developmental events, even with a high number of multiplexed fluorescent signals. The time-lapses include the simultaneous acquisition of clathrin, kdrl, and fli1, enabling visualization of the formation of ventral vasculo-endothelial protrusions while tracking the development of vesicles and vasculature. HyU enables comparative quantifications of spatio-temporal features, allowing for the determination of volumetric changes over lengthy timelapses, in this case, over the course of 300 minutes (FIG. 4B).

Figure 5:
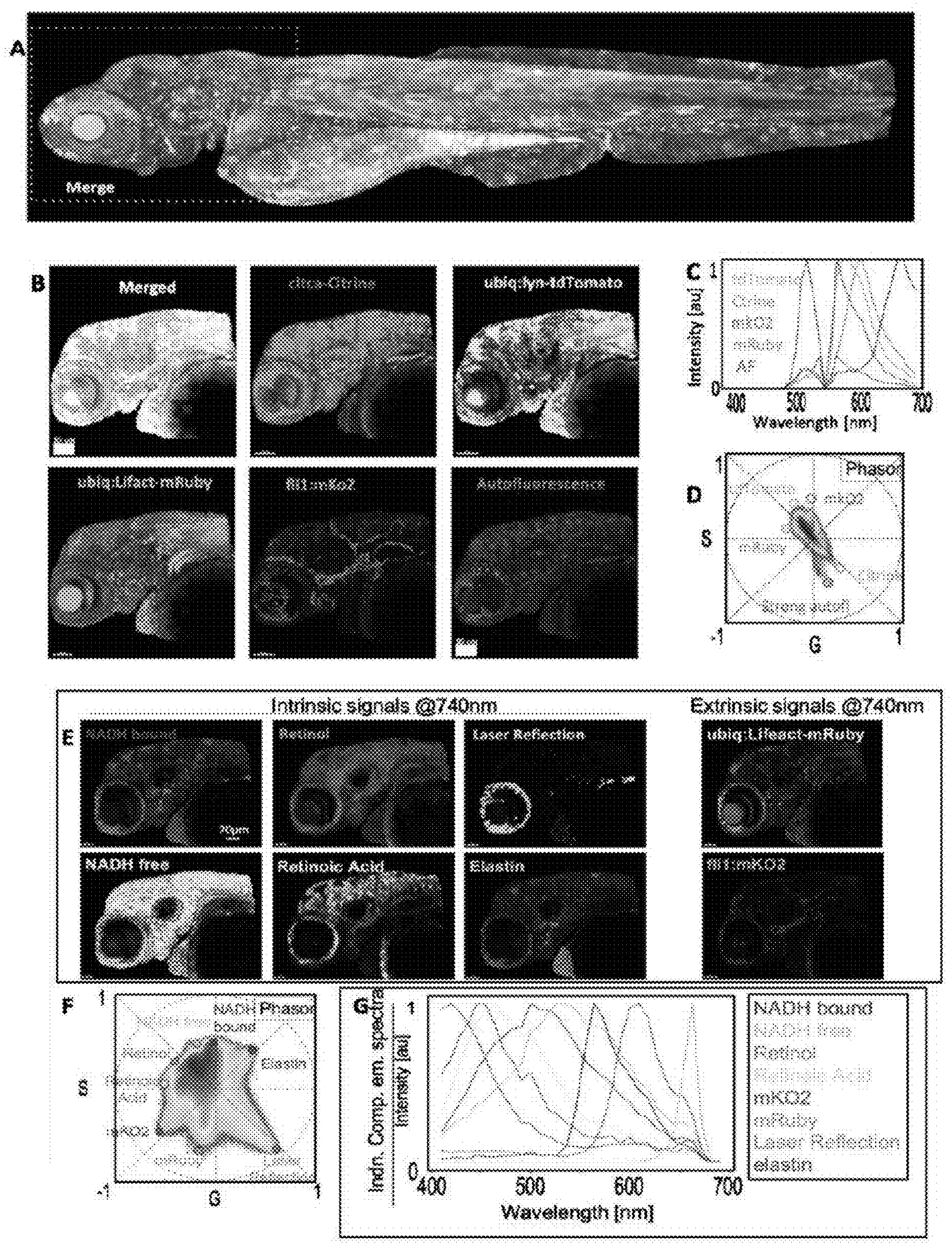
FIG. 5 illustrates that the systems and methods discussed herein, such as those describing HyU may enable identification and unmixing of low photon intrinsic signals in conjunction with extrinsic signals. In this example, (A) HyU results of a whole zebrafish embryo may provide a frame of reference not only for the improved unmixing of extrinsic signals, but also its increased sensitivity which enables identification and unmixing of intrinsic signals that inherently exist in a low-photon environment. (B) HyU results of the head region (box in A) may reveal the simplicity of identifying an unknown autofluorescent signal among multiple extrinsic signals using the phasor method for a quadra-transgenic zebrafish Gt(cltca-citrine);Tg(ubiq:lyn-tdTomato;ubiq:Lifeact-mRuby;fli1:mKO2) imaged over multiple tiles. Scale bar: 80 μm. (C) The input spectra required to perform the unmixing are easily identified on (D) the phasor plot when visualizing each spectrum as a spatial location. Phasors offer a simplified identification and selection of independent and unexpected spectral components in the encoded HyU approach. Intrinsic signals are notoriously low in emitted photons leading to an inability to unmix using traditional unmixing algorithms. (E) The zoomed-in acquisition of the head region of the embryo (box in A) displays HyU's unmixing results of many intrinsic and extrinsic signals when in an environment of very low photon output, a previously highly difficult experimental condition to unmix. Scale bar: 70 μm. (F) The phasor plot representation provides the easily identifiable eight independent fluorescent fingerprint locations. (G) The spectra corresponding to each of the eight independent spectral components are also provided a reference. Colors in (F) match renderings in (E) and (G): NADH bound (red), NADH free (yellow), retinoid (magenta), retinoic acid (cyan), reflection (green), elastin (purple) and extrinsic signals: mKO2 (blue), and mRuby (orange). All signals were excited with a (A-D) single photon laser at both 488 nm and 561 nm or a (E-G) two photon laser at 740 nm.
Figure 6:
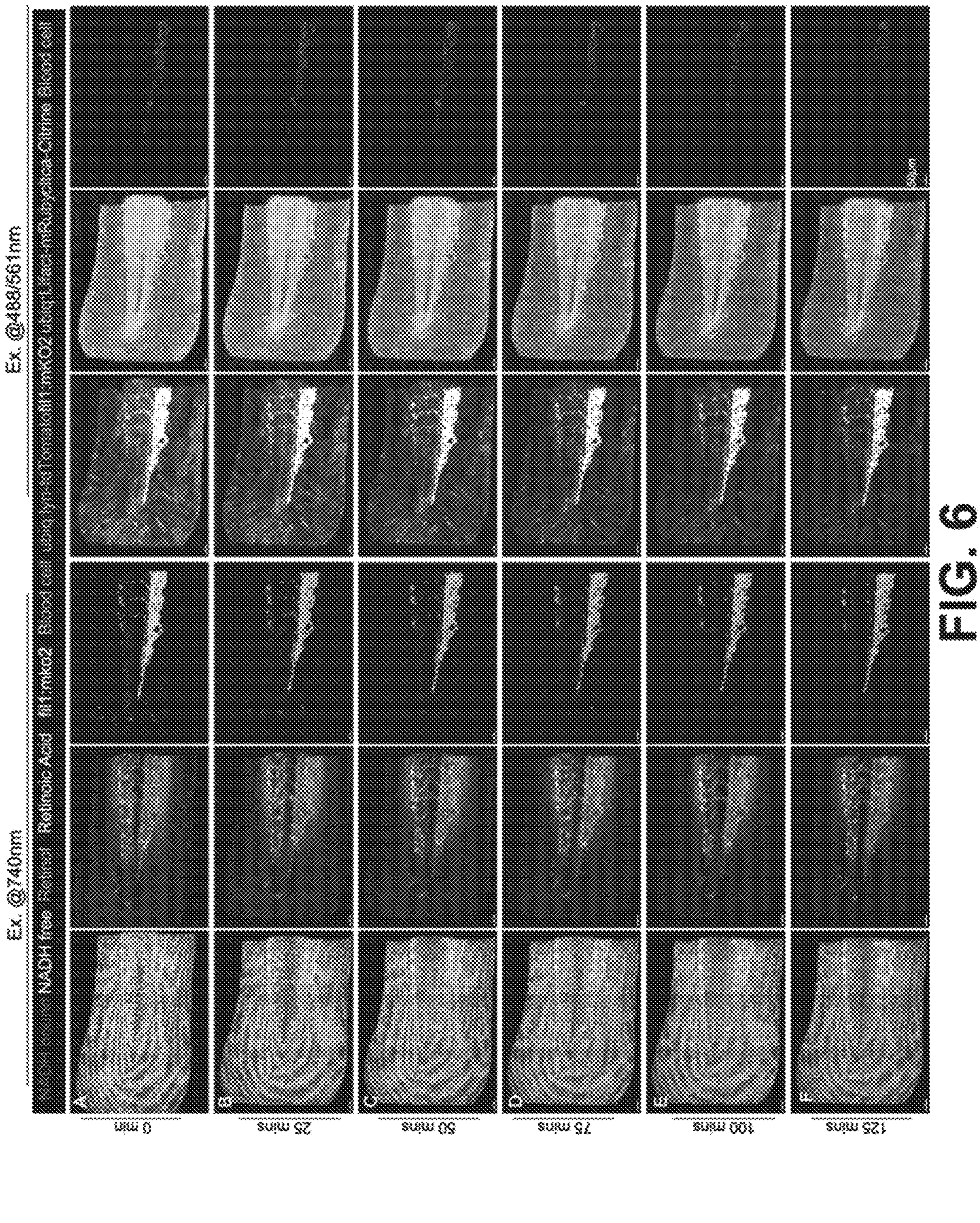
FIG. 6 illustrates that the systems and methods discussed herein, such as those describing HyU may push the upper limits of live multiplexed volumetric timelapse imaging of intrinsic and extrinsic signals. HyU's increased sensitivity provides a simple solution for the challenging task of imaging timelapse data at 6 time points (125 mins) for both intrinsic signals and extrinsic signals of a quadra-transgenic zebrafish: Tg((cltca-Citrine);(ubiq:lyn-tdTomato);(ubiq:Lifeact-mRuby);(fli1:mKO2)). (A)-(F) Volumetric renderings of HyU results for time points acquired at 25 min intervals may reveal the high-contrast and -multiplexed labels of NADH bound (red), NADH free (yellow), retinoid (magenta), retinoic acid (cyan), mKO2 (green), and autofluorescence from blood cells (blue) when excited @740 nm. Further extrinsic signals for mKO2 (yellow), tdTomato (magenta), mRuby (cyan), Citrine (green) and blood cells autofluorescence (blue) are also readily unmixed using HyU when exciting the sample @ 488/561 nm. HyU may provide the capacity to simultaneously multiplex 9 signals in a live sample over long periods of time, a previously unexplored task. Scale bar: 50 μm.
Figure 7:
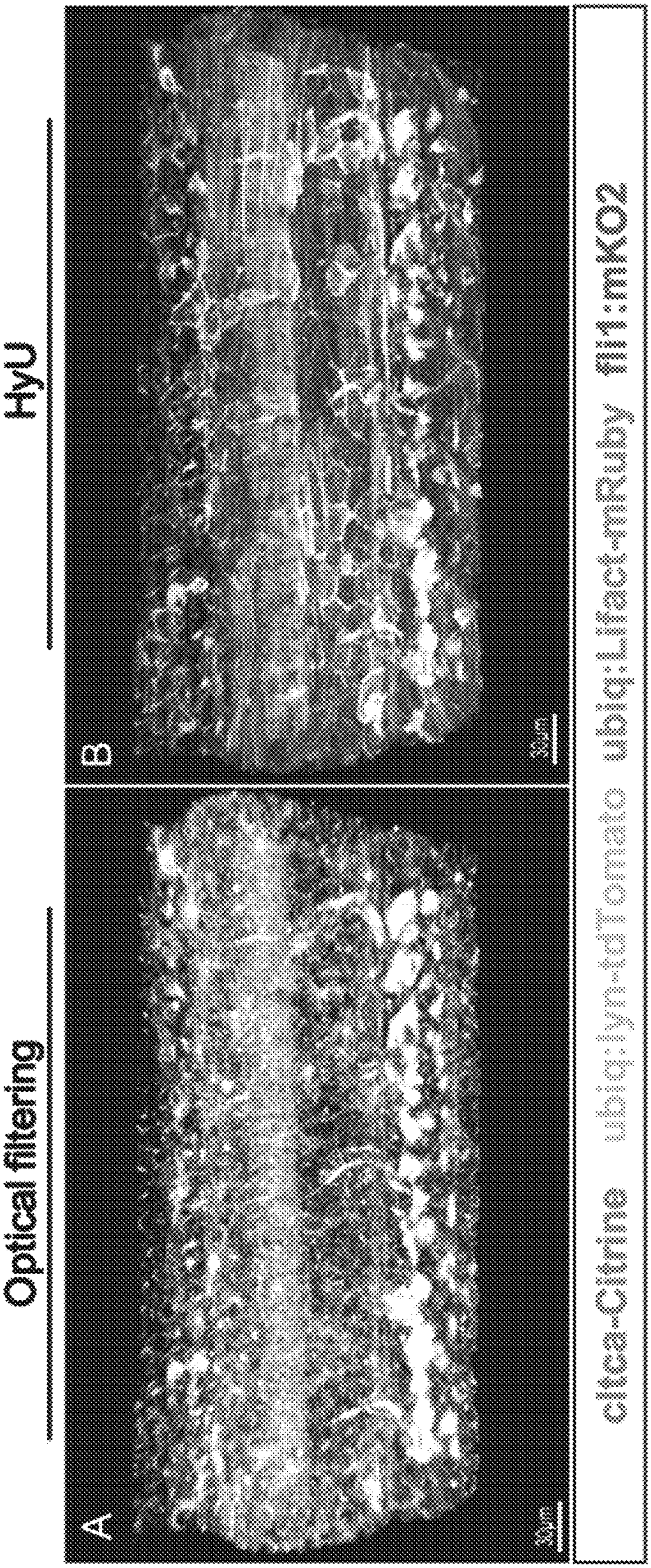
FIG. 7 illustrates how the systems and methods discussed herein, such as those describing HyU may reduce noise and signal bleedthrough compared to traditional bandpass filter imaging. Imaging of a quadra-transgene zebrafish Gt(cltca-citrine);Tg(ubiq:lyn-tdTomato;ubiq:Lifeact-mRuby;fli1:mKO2) (same data as FIG. 3) performed with (A) 4-channel optical filter imaging and (B) multispectral imaging and Hybrid Unmixing (HyU) analysis. Bleed-through from the fluorophores' overlapping emission spectra is present in A. This artifact is the result of the sharp spectral discretization imposed on the fluorescent signals by the optical filters, which fail to produce a clean distinction between Citrine (480 nm-690 nm), mKO2 (525 nm-690 nm), tdTomato (530 nm-690 nm) and mRuby (560 nm-690 nm). Fluorophores are well separated in B. Colors in both A and B represent Citrine (green), mKO2 (yellow), tdTomato (magenta) and mRuby (cyan).
Figure 8:
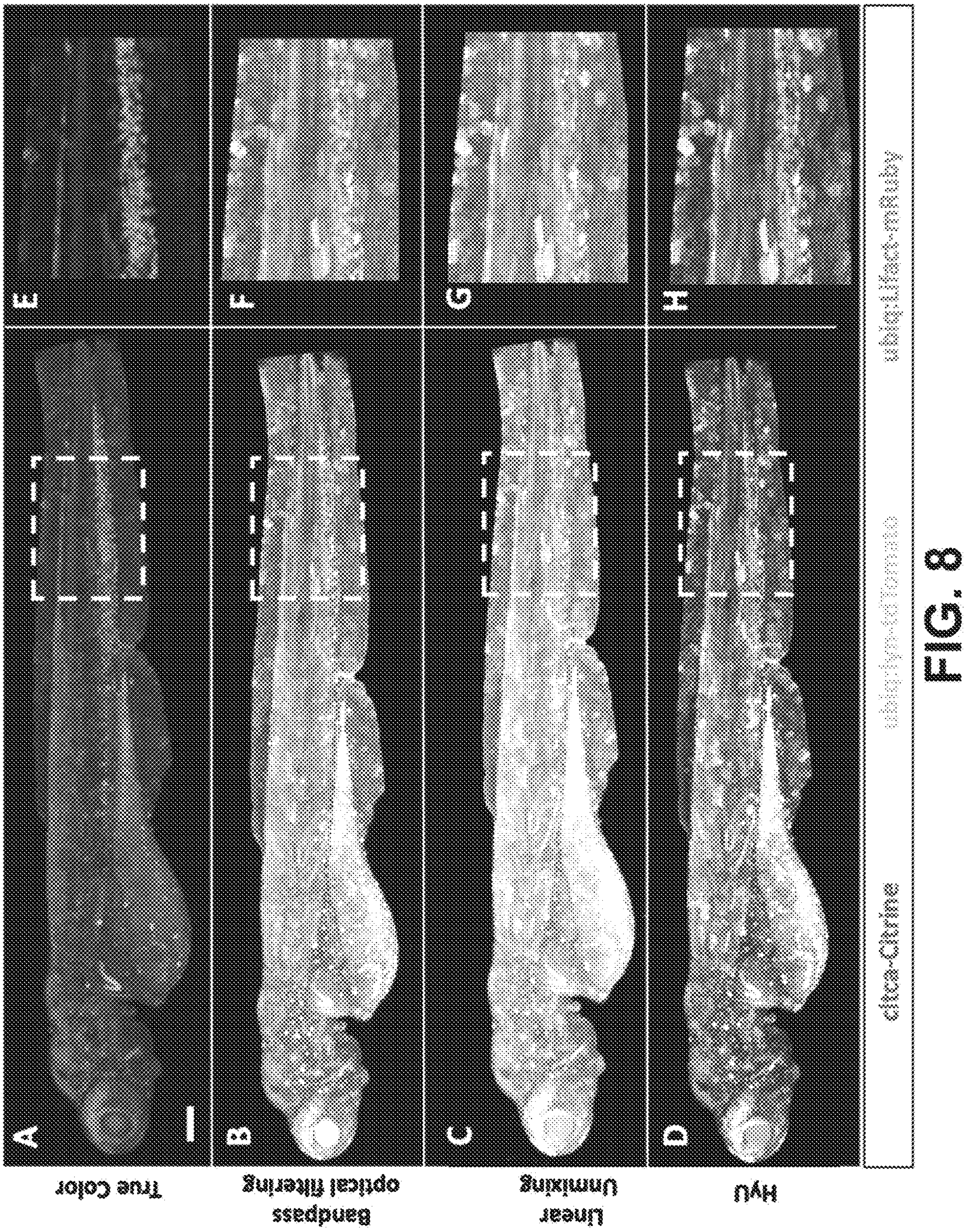
FIG. 8 illustrates how the systems and methods discussed herein, such as those describing HyU can outperform current methods. True-color rendering of a 32 channel tetra-label Gt(cltca-citrine);Tg(ubiq:lyn-tdTomato;ubiq:Lifeact-mRuby) zebrafish shows indistinguishability of multi-label in the absence of analysis. (B) Optical filter imaging presents strong bleedthrough across the 4 channels. (C) Traditional unmixing provides contrast increase across labels while still affected by incorrect re-assignment of signals. (D) Hybrid Unmixing enhances separation of spectral and spatial overlapping signals. (E-H) are the zoom in from white boxes in A, B, C, D respectively. Scale bar is 100 μm.

HyU provides the ability to combine the information from intrinsic and extrinsic signals during live imaging of samples, at both single (FIG. 5) and multiple time points (FIG. 6). The graphical representation of phasors allows identification of unexpected intrinsic fluorescence signatures in a quadra-transgenic zebrafish embryo Gt(cltca-citrine);Tg (ubiq:lyn-tdTomato;ubiq:Lifeact-mRuby;fli1:mKO2), imaged with single photon (488 and 561 nm excitation) (FIG. 5A-D). The elongated distribution on the phasor (FIG. 5C) highlights the presence of an additional, unexpected spectral signature, related to strong sample autofluorescence (FIG. 5D blue). HyU analysis of the sample, inclusive of this additional signal, provides separation of the contributions of 5 different fluorescent spectra with residual 3.9%±0.3%.

Figure 28:
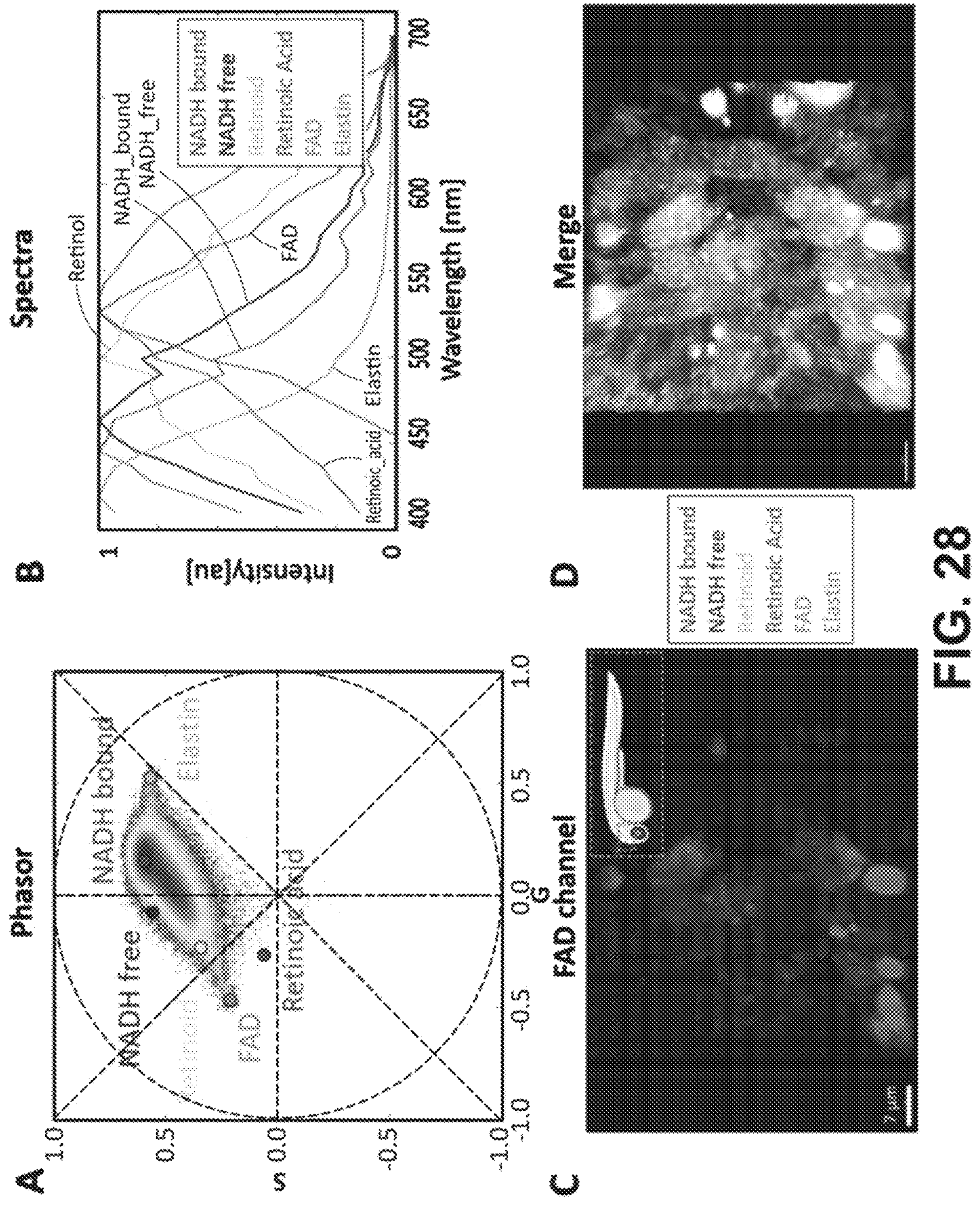
FIG. 28 illustrates Retinol and Flavin Adenine Dinucleotide (FAD) autofluorescence in high magnification hindbrain region of zebrafish embryo. (A) Phasor analysis reveals a distinct autofluorescence spectral component (magenta dot) when utilizing 740 nm 2-photon excitation to image a 22 hpf wild type zebrafish brain with high magnification (pixel size=0.078×0.078 μm) and high power (Table S1). (B) The corresponding emission spectra from the phasor selections in A. The spectrum corresponding to the magenta phasor selection in A closely matches the spectral signal of FAD obtained from in vitro solutions (Methods—Independent Spectral Signatures) and accounting for local environment changes[14]. (C) FAD unmixing channel highlights the FAD cluster in the head region of zebrafish. (D) Composite image rendering of the unmixing results for the intrinsic signals: NADH bound, NADH free, Retinoid, Retinoic Acid, FAD, and Elastin.
Figure 32:
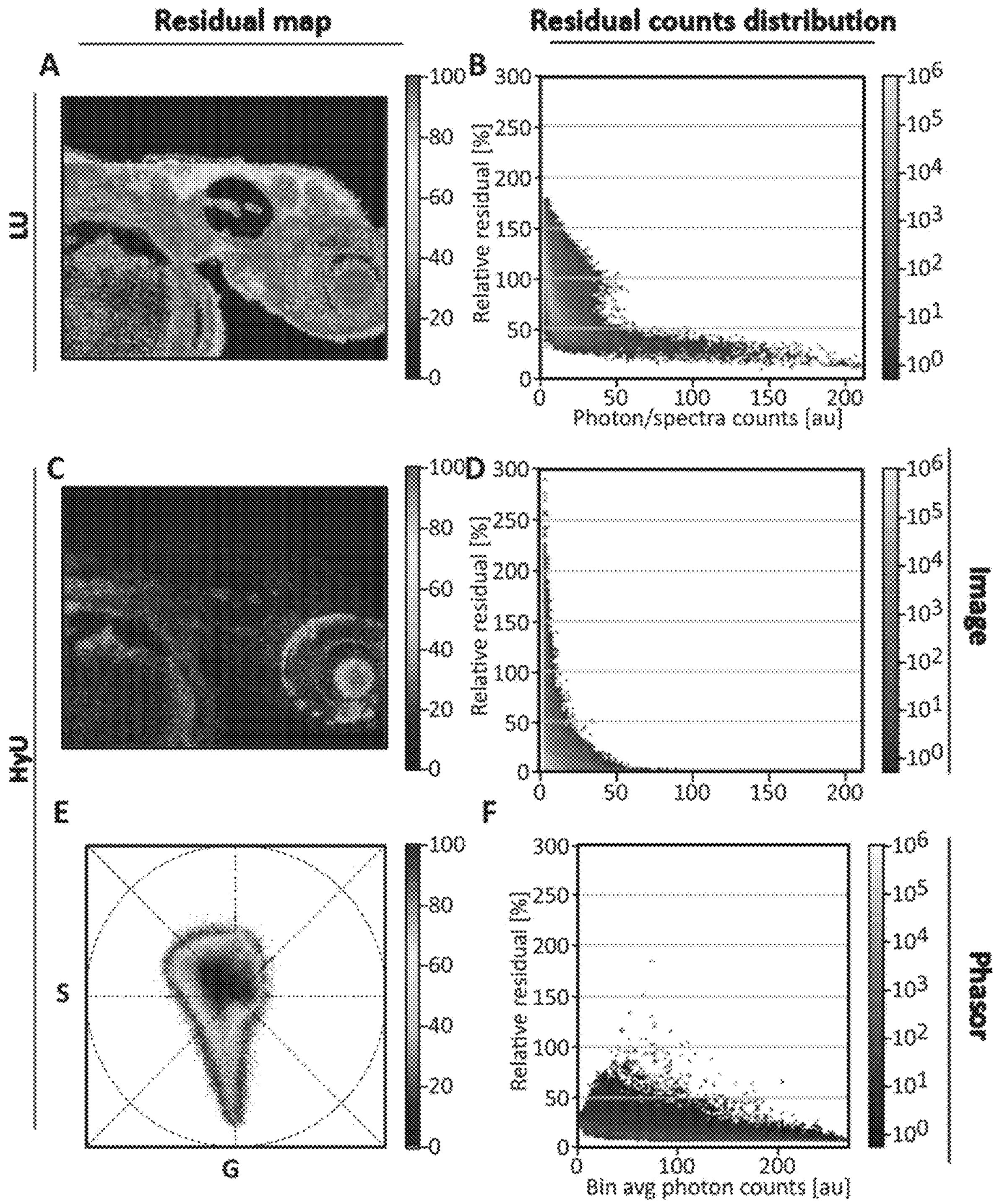
FIG. 32 illustrates an example residual analysis of intrinsic fluorescent signals of HyU and LU shows robust results for HyU unmixing. Residual analysis was performed on a hyperspectral fluorescent data of a 3 dpf quadra-transgenic zebrafish Gt(cltca-citrine);Tg(ubq:lyn-tdTomato;ubiq:Lifeact-mRuby;fli1:mKO2) whose unmixing results were reported in FIG. 5. Residual analysis results are shown for (A-B) LU and (C-F) HyU, respectively. Residual Image maps (Methods) of the z-averaged dataset for LU and HyU in A and C, respectively, show lower residual values for HyU, suggesting improved quality of unmixing. Residual distribution relative to the original intensity in each pixel as a function of estimated photon counts per spectrum are presented for LU and HyU in B and D, respectively, showing a distribution with lower Relative residual for HyU. (E) Residual Phasor Map (Methods) presents higher residual values in the regions corresponding to the edge of the phasor cluster. (F) Residual Phasor Histogram for HyU shows distribution of residuals in the broad dynamic range of photons for experimental data.
Figure 33:
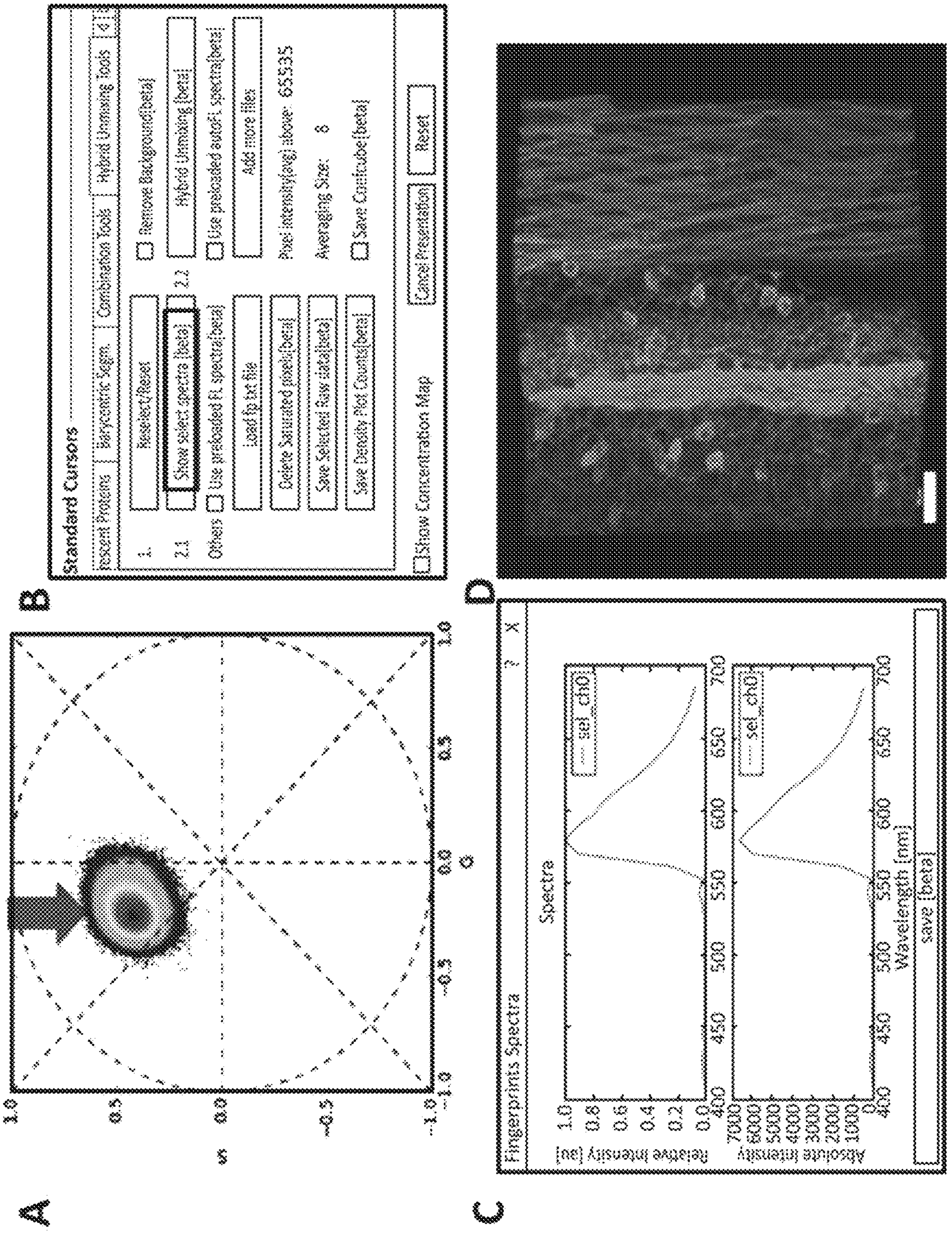
FIG. 33 illustrates an example endmember Spectrum selection process. (A) Phasor map shows the spectral distribution of the data for a single fluorescent labelled sample, in this case an 18 hpf transgenic Tg(ubiq:lyn-tdTomato) zebrafish. (B) The average spectrum corresponding to a phasor bin selection (red point in A) can be visualized using software plotting discussed herein. (C) the corresponding average spectrum with relative (top) and absolute (bottom) intensity. The save button allows exporting spectral data as a txt file that can be re-loaded for unmixing other data. (D) Unmixing result. More step-by-step information is available in the README file associated with the software in this publication.
Figure 34:
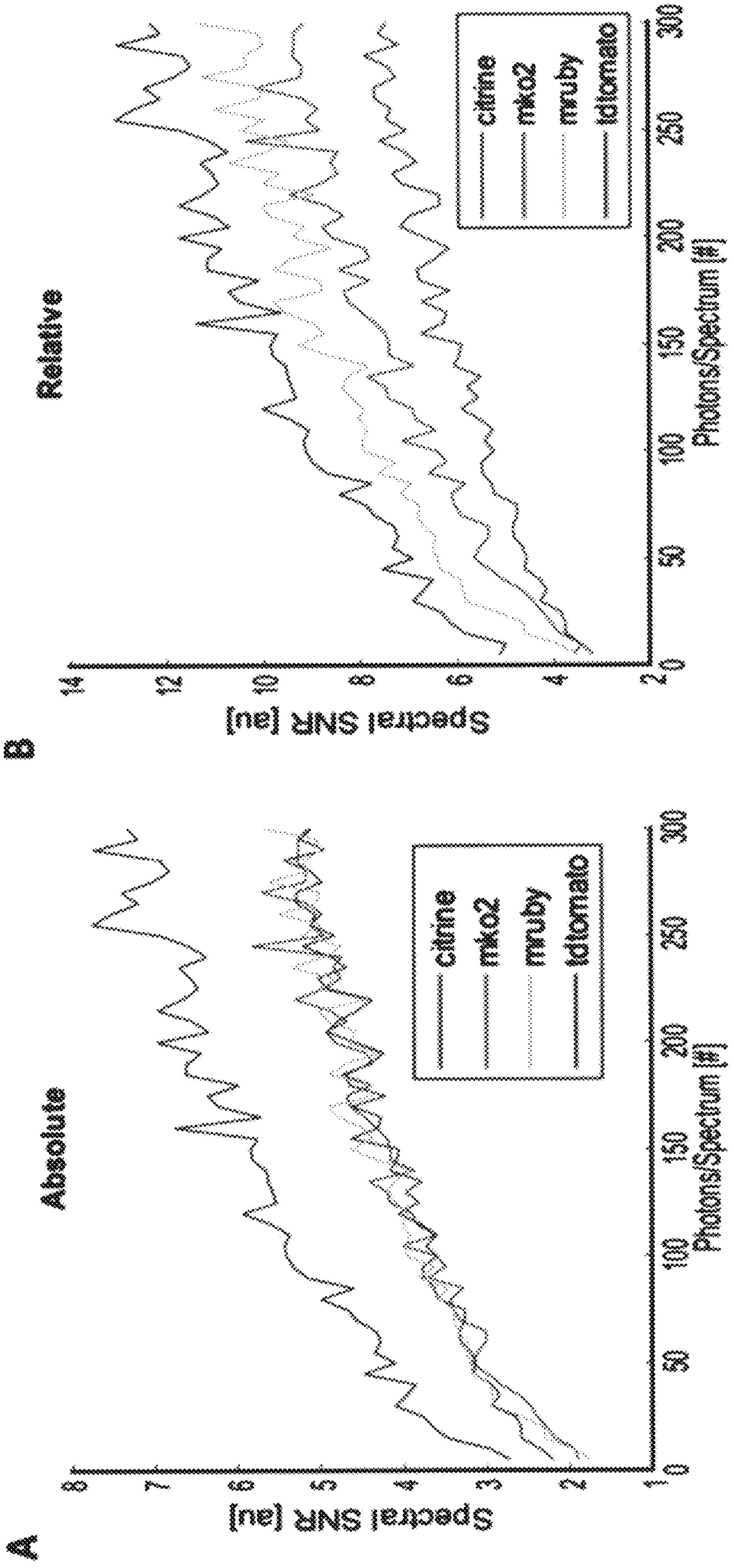
FIG. 34 illustrates an example relationship between Spectral SNR and Photon/Spectrum. The direct relationship between SNR and photons per spectrum is shown here using the calculation of Spectral SNR for varying levels of photons per spectrum. The spectral SNR has a general trend of increased values with increasing photons per spectrum, but it is not a truly monotonic function. This non-monotonicity demonstrates the limitations of SNR when analyzing spectral images. (A) Absolute Spectral SNR and (B) Relative Spectral SNR follow the same trends of higher values with increasing photons per spectrum. However, the Relative Spectral SNR better differentiates the effects of the differing spectral shapes on the SNR. Citrine, mKO2, mRuby, and tdTomato each have easily distinguished values for the slope of the regression in ascending order. tdTomato has a spectral shape which provides the best SNR while Citrine provides the worst SNR, even with the same number of photons per spectrum.
Figure 35A:
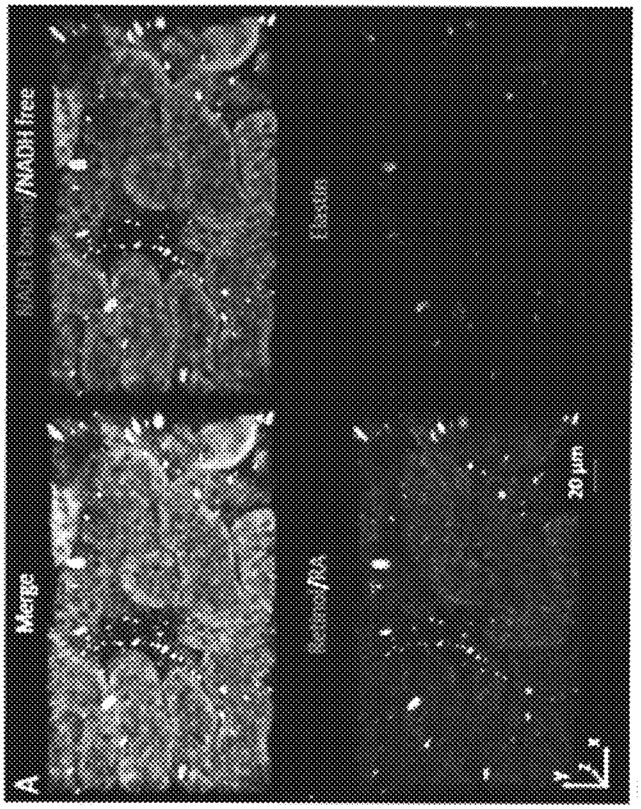
FIG. 35 illustrates example intrinsic fluorescent signatures in fresh mouse tissue. Intrinsic fluorescent signatures in fresh kidney tissue of a 7 months Balb-c mouse imaged with 2-photon excitation at 740 nm in a 150 μm deep volume. Despite the increasing scattering effect of this mammal tissue with increasing depth, HyU can perform unmixing of intrinsic fluorescent signals. (A) Volumetric rendering of the unmixing results of five intrinsic fluorescent signatures shows results consistent with literature, as visible in the (B-E) orthogonal views of (C) an unmixed (x,y) cross-section of the volume at 30 μm depth in the sample and its corresponding (B) (x,z) and (E) (y,z) projections. (D) Averaged autofluorescent signals for each acquired spectral (x,y) section over the 150 μm depth of the volume show a sharp decrease of intensities after 75 μm depth as visible in E, the corresponding (y,z) projection.
Figure 35B:
Figure 35C:
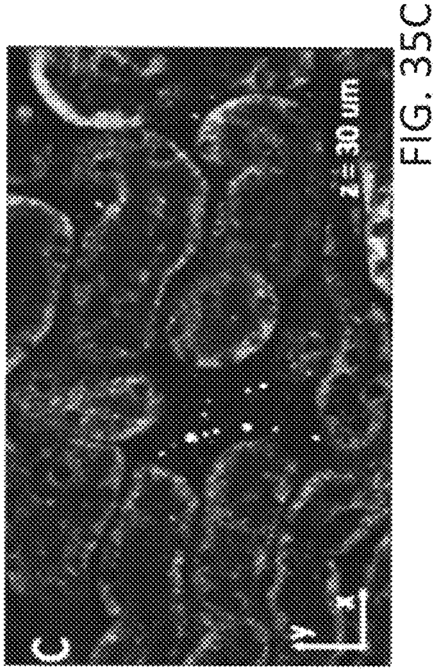
Figure 35D:
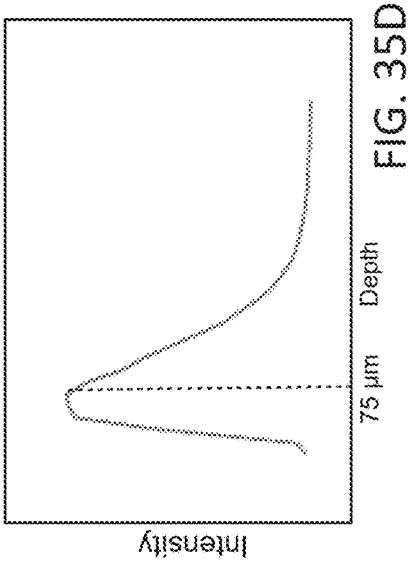
Figure 35E:
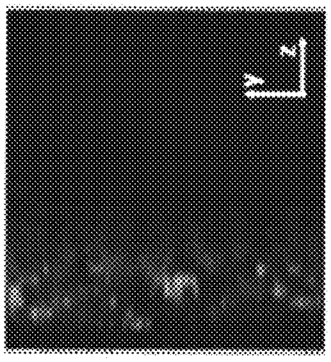

HyU allows for reduced energy load, tiled imaging of the entire embryo without perturbing its development or depleting its fluorescence signal (FIG. 5A). The higher speed, lower power imaging allows for subsequent re-imaging of the same sample, as in the zoomed high-resolution acquisitions of the head section (FIG. 5B,E). With the ability to unmix low photon signals, HyU enables imaging and decoding of intrinsic signals, which are inherently low light. Two photon lasers are ideal for exciting and imaging blue-shifted intrinsic fluorescence from samples. Here, the same quadra-transgenic sample is imaged using about 740 nm excitation to access both intrinsic and extrinsic signals (FIGS. 5E-G, 27, and Example 23). HyU enables unmixing of at least 9 intrinsic and transgenic fluorescent signals (FIG. 5), recovering fluorescent intensities from labels illuminated at a sub-optimal excitation wavelength (FIG. 5E). The spectra for intrinsic fluorescence were obtained from in vitro measurements and values reported in literature. For this sample the intrinsic signals arise from events related mainly with metabolic activity (NADH and Retinoids), tissue structure (elastin), and illumination (laser reflection) (FIGS. 5E,28,32, and Example 23). These results demonstrate that HyU of this disclosure is a powerful tool for allowing the imaging and analysis of endogenous labels.

The HyU capabilities can be used to multiplex volumetric timelapse of extrinsic and intrinsic signals by imaging the tail region of the same quadra-transgenic zebrafish embryo. Extrinsic labels at 488/561 nm and the intrinsic signals with 740 nm two photon can be excited, collecting 6 tiled volumes over 125 mins (FIGS. 6, 15-17,21, and Example 23). HyU unmixing in this example allows for distinction of 9 signals, separating their contributions with sufficiently low requirements to allow repeated imaging of notoriously low SNR intrinsic fluorescence.

The advantages of Hybrid Unmixing (HyU) over the conventional Linear Unmixing (LU) in performing complex multiplexing interrogations are discussed herein. HyU may overcome the significant challenges of separating multiple fluorescent and autofluorescent labels with overlapping spectra while minimally perturbing the sample with excitation light.

Figure 29:
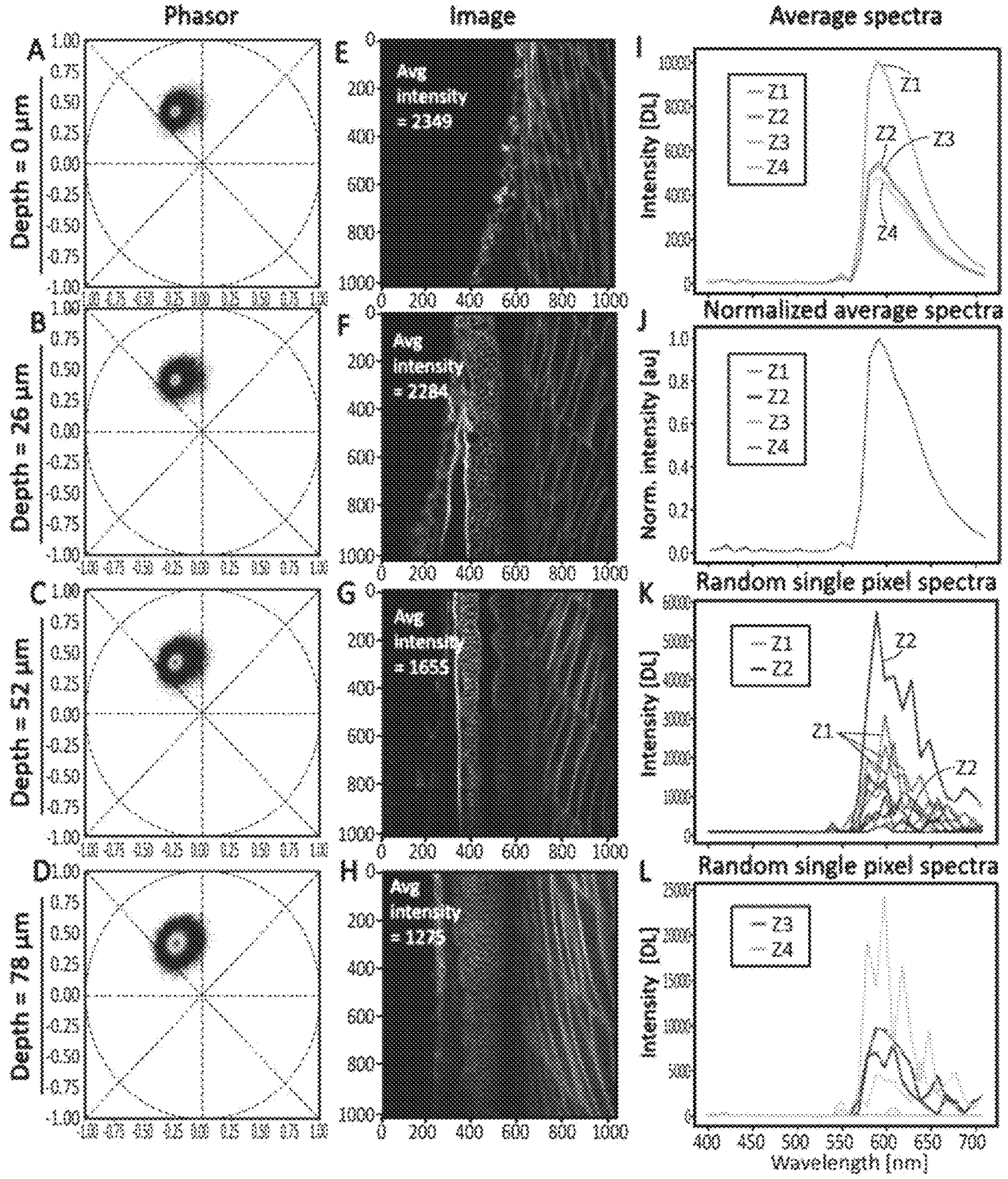
FIG. 29 illustrates an example phasor analysis on signal distortion in deep tissue. Images at different Z-positions of a 3D (x,y,z) dataset of 19 hpf Tg(ubiq:lyn-tdTomato) zebrafish acquired from 0 μm to 80 μm (relative to the dataset) depth displaying at every 13 z-slices. (A-D) Phasors calculated from the single slices at 0 μm, 26 μm, 52 μm, and 78 μm depth. (E-H) Corresponding average intensity images (across the 32 spectral channels) for each z-slice show an expected decrease in fluorescence intensity with depth. (I) Average spectra of the pixels linked to the phasor position bin for the tdTomato fluorescent signature for each of the four presented z-slices (0, 26, 52, 78 μm) show a decrease in the spectral area without change in spectral shape as shown by (J) normalizing the average spectra shown in I to each spectrum's maximum value. This demonstrates the spectral shape does not change across different depths (z-planes), while the overall intensity decreases. (K) Randomly selected spectra from the raw spectral image at 0 μm (blue) and 26 μm (red), five spectra for each image and similarly (L) for 52 μm (green) and 78 μm (yellow). Two yellow and three green spectra are not clearly visible because of low signal intensity.

One example advantage of HyU over the conventional LU is its multiplexing capability when imaging in the presence of biological and instrumental noise, especially at low signal levels. HyU increased sensitivity improves multiplexing in photon limited applications (FIG. 2F-L), in deeper volumetric acquisitions (FIGS. 3I, 29) and in signal starved imaging of autofluorescence (FIG. 5E,6). Simulation results (FIG. 2) demonstrate that HyU improves unmixing of spatially and spectrally overlapping fluorophores excited simultaneously. The increased robustness at low photon imaging conditions reduces the imaging requirements for excitation levels and detector integration time, allowing for imaging with reduced photo-toxicity. Live imaging on multi-color samples performed at high sampling frequency enables improved tiling to increase the field-of-view (FIGS. 3,4) while maximizing the usage of the finite fluorescent signals over time. Two-photon imaging of intrinsic and extrinsic signals suggests the ability of HyU to multiplex signals with large dynamic range differences (FIG. 5) extending multiplexed volumetric imaging into the time dimension (FIG. 6). Although improved, images with particularly low signal still present corruption (FIG. 10), setting a reasonable range of utilization above 8 photons/spectrum.

Simplicity of use and versatility are other key advantages of HyU over the conventional LU, inherited from both the phasor approach and traditional unmixing algorithms. Phasors here operate as a spectral encoder, reducing computational load and integrating similar spectral signatures in histogram bins of the phasor plot. This representation simplifies identification of independent spectral signatures (FIG. 5, and Example 22) through both phasor plot selection and phasor residual mapping (FIG. 17), accounting for unexpected intrinsic signals (FIGS. 5,6,18, and Example 23) in a semi-automated manner, while still allowing fully-automated analysis by means of spectral libraries.

Figure 18:
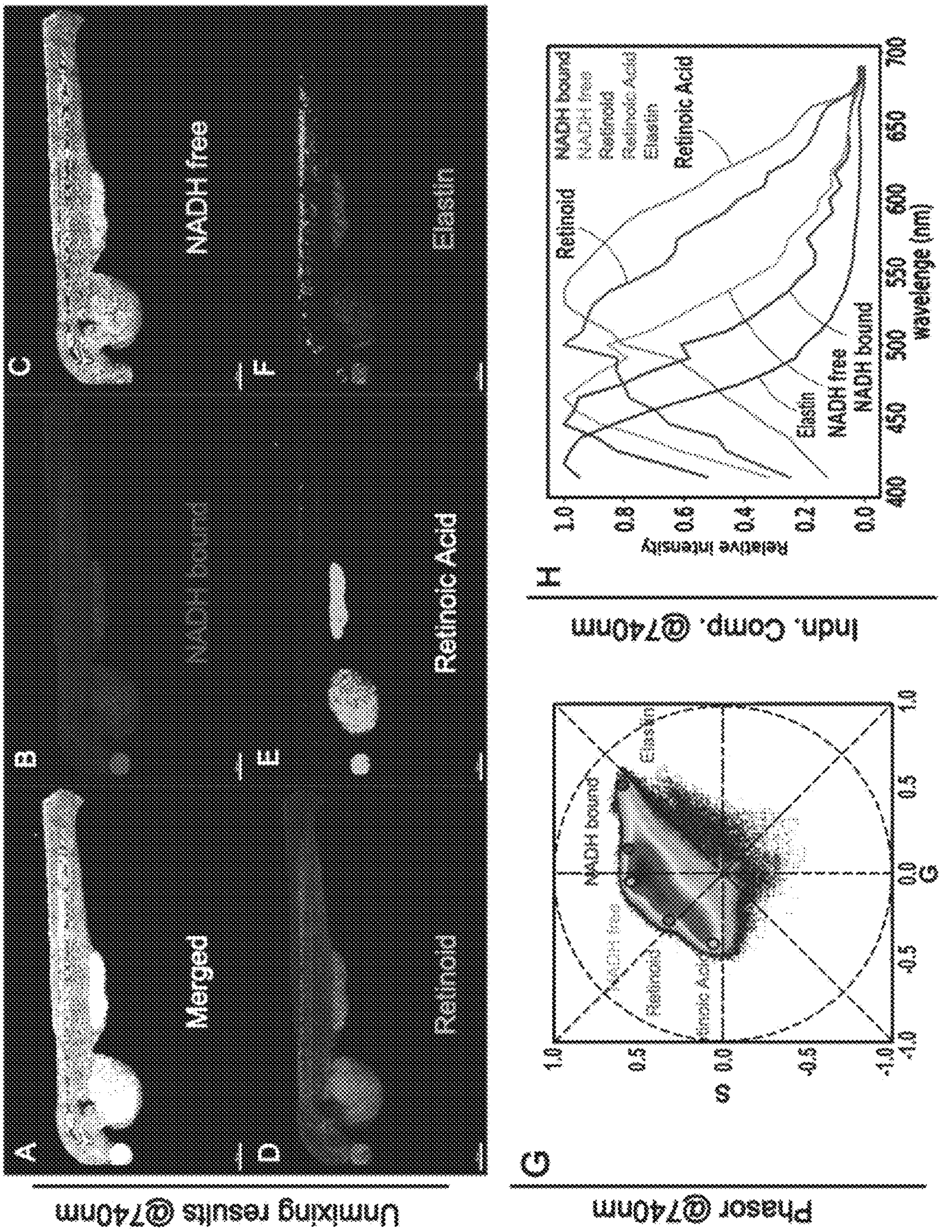
FIG. 18 illustrates a HyU analysis of 36 hpf Casper zebrafish which demonstrates feasibility of unmixing only intrinsic signals. Casper zebrafish is a transgenic zebrafish characterized by the absence of pigments. Dataset was acquired in the two-photon spectral mode @740 nm excitation. HyU Unmixing was performed utilizing 5 pure intrinsic signals measured in solution (Methods): (A) Merged overview of all signals (B) NADH bound (C) NADH free (yellow), (D) retinoid (magenta), (E) retinoic acid (cyan) which appears mainly in the yolk sac, known location where carotenoids are stored, transferred and then metabolized to retinoic acid[13] (F) elastin (green) has a similar distribution with in the zebrafish floorplate at this developmental stage (G) Phasor (H) average spectra from selection in G.

The simplicity of this approach is especially helpful in live imaging where identifying independent spectral components remains an open challenge, owing to the presence of intrinsic signals (FIG. 18, and Example 22). High-SNR reference spectra can be derived from other experimental data or identified directly on the phasor. Selection of portions on the phasor plot allows for visualization of the corresponding spectra in the wavelength domain (FIGS. 5C,D,F,G, and 33). This intuitive versatility allows for identification of both the number of unexpected signatures and their spectra, a task previously difficult to perform due to noise and lack of global visualization tools.

In single photon imaging (FIGS. 5A-D), HyU phasor allowed identification of a fifth distinct spectral component arising from general autofluorescent background, thereby improving the unmixed results. In two photon imaging, HyU enabled identification and multiplexing of 8 highly overlapping signals possessing a wide dynamic range of intensities, between intrinsic and extrinsic markers (FIGS. 5F,G). Combination of single and two photon imaging increased the number of multiplexed fluorophores to 9 (FIG. 6), considering some of the extrinsic labels being excited at two photons. Multiplexing of signals may be further improved by implementing HyU on fluorescent dyes.

HyU performs better than standard algorithms both in the presence and absence of phasor noise reduction filters. Compared with the conventional LU, the unmixing enhancement when such filters are applied is demonstrated by a decrease of the MSE of up to 21% (FIG. 2C), with a reduction of the average amount of residuals by 7-fold. Even in the absence of phasor denoising filters, HyU performs up to 7.3% better than the standard (FIG. 2D) based on Mean Squared Error of synthetic data unmixing. This base improvement is due to the averaging of similarly shaped spectra in each phasor histogram bin, which reduces the statistical variability within the spectra used for the unmixing calculations (FIG. 1E). This averaging strategy works well for general fluorescence spectra owing to their broad and mostly unique spectral shape.

In the absence of noise, for example in the ground truth simulations, the conventional LU produces an MSE 6-fold lower than HyU (FIGS. 11B-C,12G). In these noiseless conditions, the binning and averaging of spectra in the phasor histogram, without denoising, provides statistically indifferent values of error respect to the conventional LU, suggesting results of similar quality.

Figure 19:
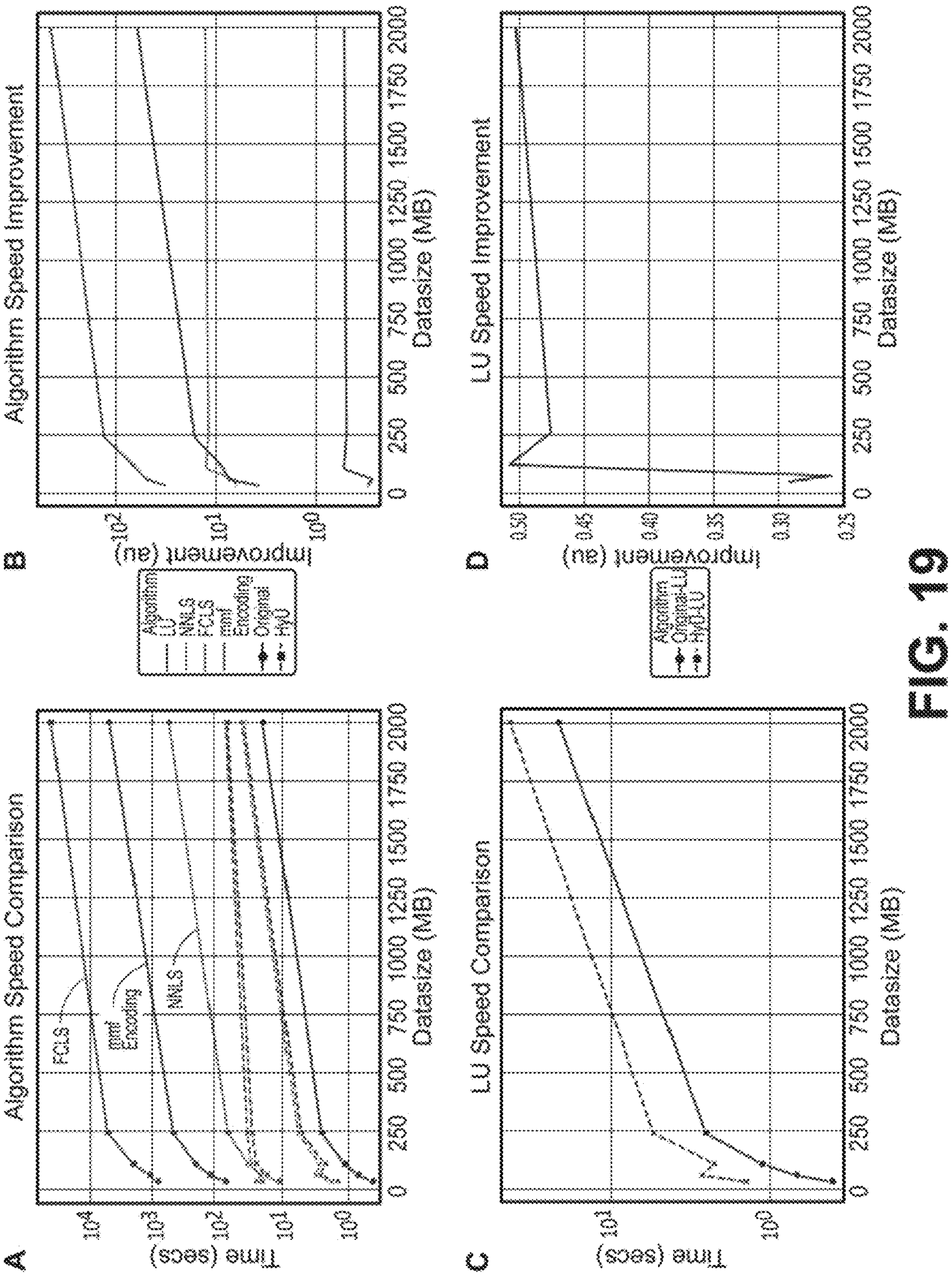
FIG. 19 illustrates a speed comparison and improvement plots of multiple unmixing algorithms in their original form vs HyU encoded. (A) Computational times of multiple unmixing algorithms for both original (pixel-by-pixel) and HyU versions over a range of hyperspectral imaging datasets sizes. (B) Improvement in speed using the ratio of the HyU over the Original unmixings demonstrate a vast increase in speed for all algorithms other than LU across all input data sizes. (C, D) Computational times and speed improvement for original and HyU versions of LU show that the original version of LU provides higher computational speeds at ~2×. Plots A-C use logarithmic scales while plot D uses a linear scale for the y-axis.
Figure 20:
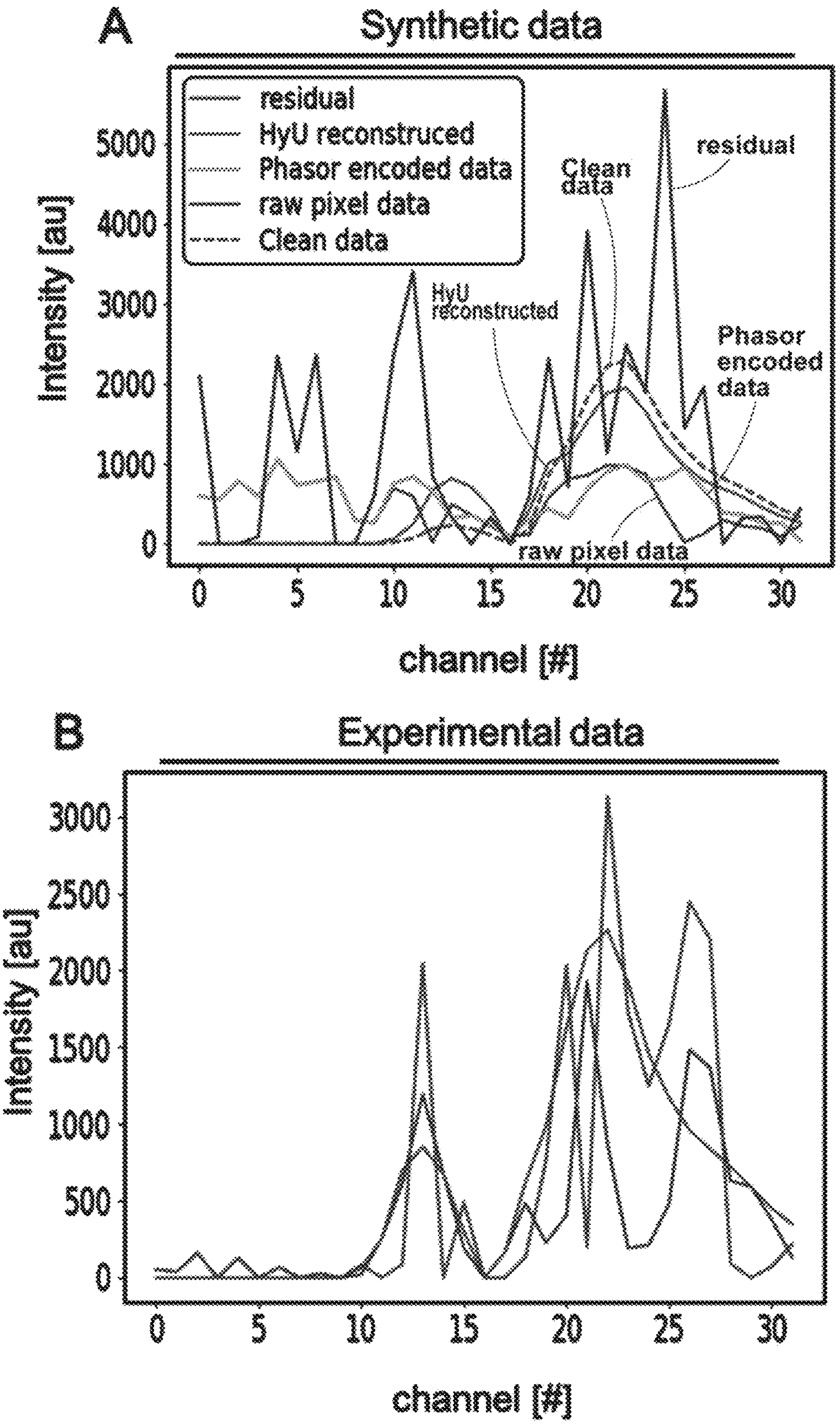
FIG. 20 illustrates a residuals in synthetic data and experimental data. (A) Data was simulated with the purpose to cover wide ranges of noise and to allow for thorough testing of the algorithm's performance. In this example a ground truth spectrum with 14 photons (red dashed line) is simulated accounting for multiple types of noise (dark green line). The simulated spectrum presents disrupted shape with substantial presence of noise. During HyU analysis, in the encoding of spectra within a phasor bin, the simulated spectrum (dark green line) is averaged with similar spectra of multiple other pixels, producing (light green light). The spectrum recovered with Hybrid Unmixing (orange line) is similar to the ground truth. In the calculation of residuals, however, due to the disrupted signal of simulation (dark green line), the absence of noise in the clean data is counted as residual. (B) Spectrum from experimental data (from FIG. 3) at a similar photon-range (15 to 20 photons) for comparison. The same color code is utilized for the spectra lines, without ground truth owing to the nature of experimental data.
Figure 21:
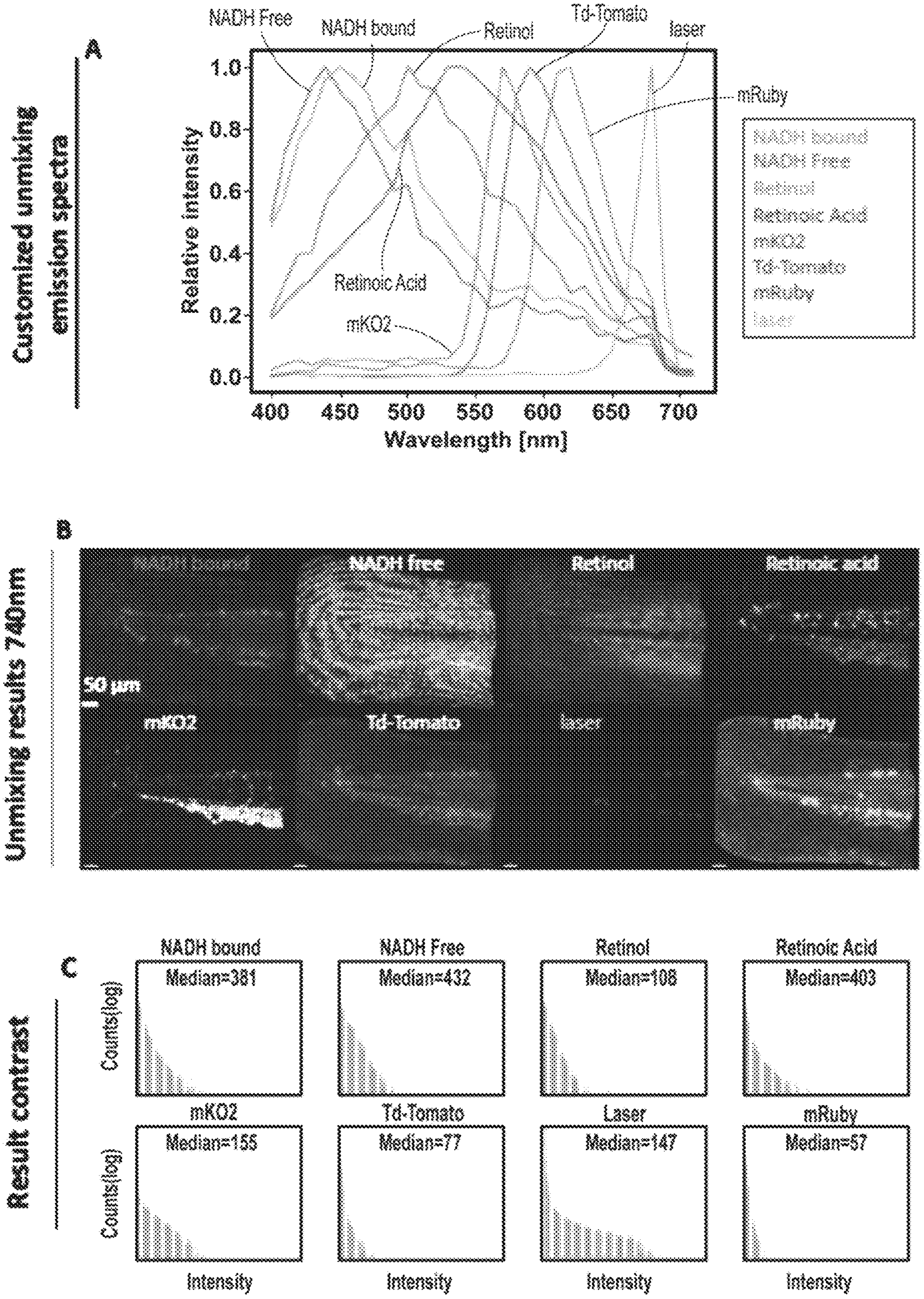
FIG. 21 illustrates HyU unmixing on low concentration signals using customized independent spectra. Results from unmixing intrinsic and extrinsic signals of a quadra-transgenic zebrafish: Gt(cltca-citrine);Tg(ubiq:lyn-tdTomato; ubiq:Lifeact-mRuby;fli1:mKO2) at a single timepoint of the dataset presented in FIG. 6 provide further information and highlight the weak expression of some extrinsic signals in this dataset. (A) Input spectra for the intrinsic signatures were directly acquired by selection of the endmembers in the phasor plot. Input spectra for the extrinsic signatures were acquired from other datasets of samples expressing those signatures individually and excited at 740 nm 2-photon, since these extrinsic signals are not strongly expressed within this dataset. (B) Renderings of unmixing results were automatically adjusted to show the best contrast. Unmixing can still be performed with spectra from weak input signatures. (C) Histogram counts of each unmixed independent spectral signature demonstrate the low signals of the extrinsic fluorescence signatures compared to the intrinsic ones. The median value of the mRuby and tdTomato channels are 57 and 77 Digital Levels respectively, considerably lower than those of the other signals.

HyU can interface with different unmixing algorithms, adapting to existing experimental pipelines. Hybridization with iterative approaches such as non-negative matrix factorization, fully constrained and non-negative least-squares were tested. Speed tests with iterative fitting unmixing algorithms demonstrate a speed increase of up to 500-fold when the HyU compressive strategy is applied. (FIG. 19, and Example 24). Due to the initial computational overhead for encoding spectra in phasors, there is a 2-fold speed reduction for HyU in comparison to standard LU. However, this may be improved with further optimizations of the HyU implementation or by implementing different types of encoding.

One restriction of HyU may derive from the mathematics of linear unmixing, where linear equations representing the unmixed channels need to be solved for the unknown contributions of each analyzed fluorophore.

To obtain a better solution from these equations and to avoid an underdetermined equation system, the maximum number of spectra for unmixing may not exceed the number of channels acquired, generally 32 for commercial microscopes.

This number could be increased; however, due to the broad and photon-starved nature of fluorescence spectra, acquisition of a larger number of channels could negatively affect the sample, imaging time and intensities. Depending on the number of labels in the specimen of interest, extending the number of labels to simultaneously unmix beyond 32 will likely require spectral resolution upsampling strategies.

Figure 22:
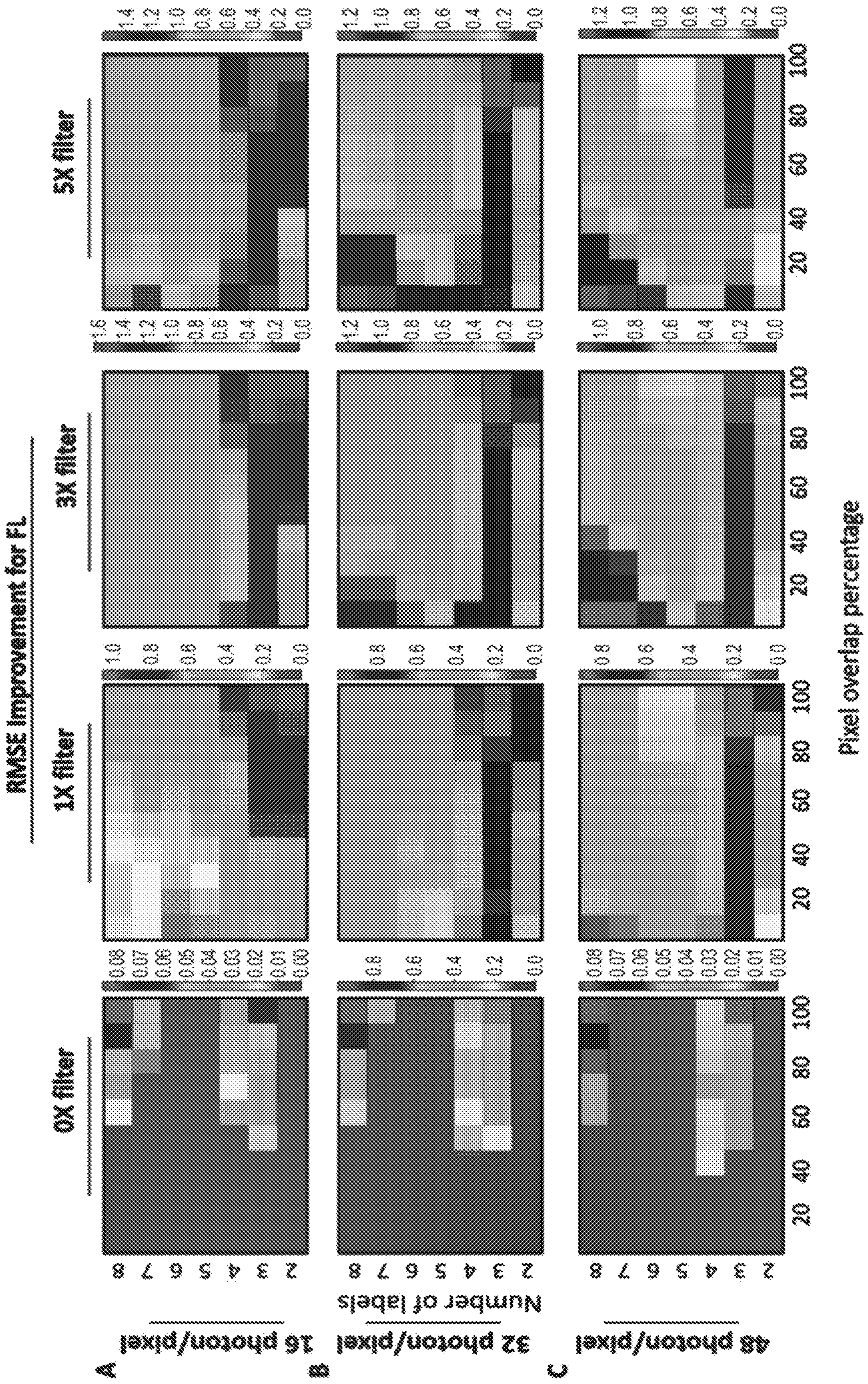
FIG. 22 illustrates a Relative Mean Square Error (RMSE) improvement for simulated fluorescent spectral combinations which highlights increased HyU performance across multiple denoising filters. Twelve matrices demonstrate the RMSE improvement of HyU with respect to LU when unmixing a collection of synthetic data with 2 to 8 extrinsic labels (Y axis of each matrix) as a function of the spatial overlap of these labels in a sample (X axis of each matrix). In the matrix, 0% overlap denotes simulations with spatially distinct fluorophores, where each pixel corresponds to a single fluorophore, while simulations with 100% overlap contain, in every pixel, a randomized ratio of the n fluorophores. Each one of the values reported in a matrix is the average of a 1024×1024×32 pixels simulation and shows the RMSE improvement of HyU to LU. Different columns in the figure report the RMSE improvement matrices with different numbers of denoising filters (0×, 1×, 3×, 5×) applied with a total number of photons per pixel at (A) 16 (B) 32 (C) 48. In the absence of denoising filters, the improvement of HyU overall is less than 8%. Denoising filters improve RMSE by over 80%. Spectra utilized for this simulation are reported in FIG. 26A.
Figure 24:
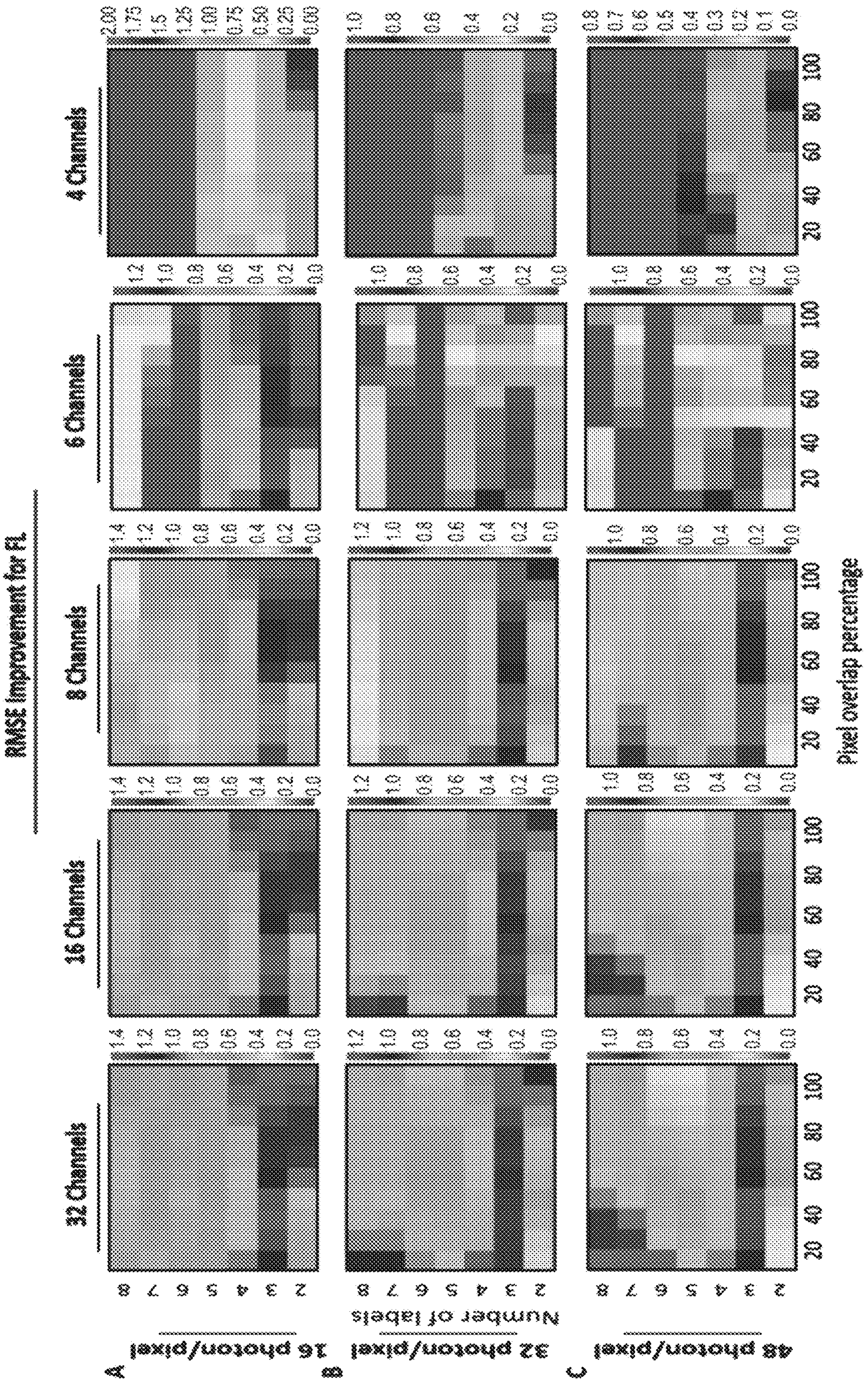
FIG. 24 illustrates an RMSE improvement for simulated fluorescent spectral combinations which highlights decreasing overall performance across decreased number of spectral channels. Fifteen matrices demonstrate the RMSE improvement of HyU with respect to LU when unmixing a collection of synthetic data with 2 to 8 extrinsic labels (Y axis of each matrix) as a function of the spatial overlap of these labels in a sample (X axis of each matrix). In the matrix, 0% overlap denotes simulations with spatially distinct fluorophores, where each pixel corresponds to a single fluorophore, while simulations with 100% overlap contain, in every pixel, a randomized ratio of the n fluorophores. Each one of the values reported in a matrix is the average of a 1024×1024×32 pixels simulation and shows the RMSE improvement of HyU to LU with 3× denoising filters. Columns in the figure represent RMSE improvement matrices across an increasingly binned number of spectral channels (32, 16, 8, 6, 4) applied with a total number of photons per pixel at (A) 16 (B) 32 (C) 48. When utilizing 32 spectral channels data, RMSE improvements reach above the previously reported 80% for highly overlapping fluorophores. Successively increasing the binning across the wavelength dimension (and therefore decreasing the number of spectral channels) shows a slow downward trend of the RMSE improvement until the 4 spectral channels matrices, where the RMSE improvement drops drastically down to below 8%, especially for more than 6 labels. Spectra utilized for this simulation are reported in FIG. 26A.
Figure 25:
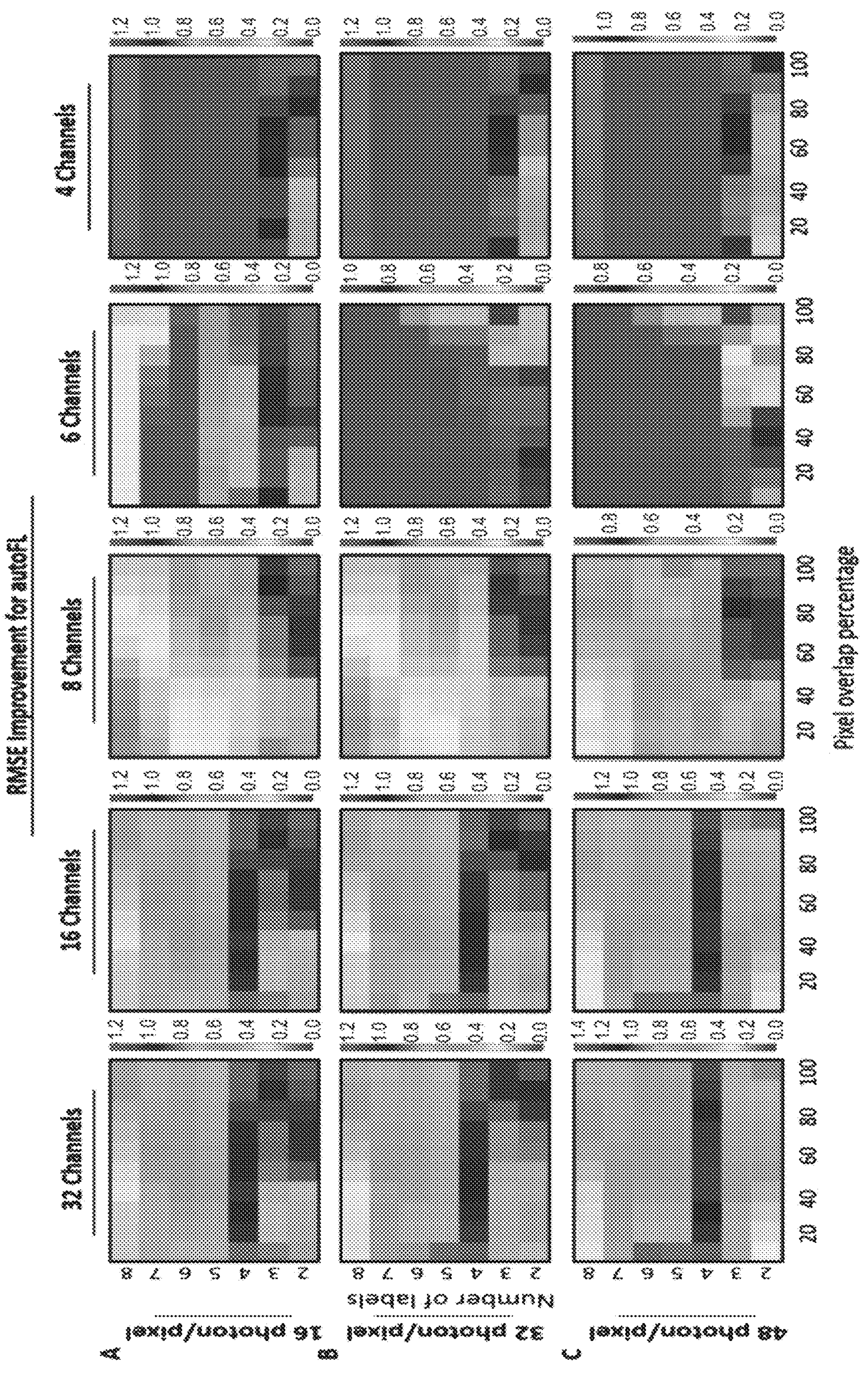
FIG. 25 illustrates an RMSE improvement for simulated fluorescent and autofluorescent spectral combinations which highlights decreasing overall performance across decreased number of spectral channels. Fifteen matrices demonstrate the RMSE improvement of HyU with respect to LU when unmixing a collection of synthetic data with 2 to 8 extrinsic and intrinsic labels (Y axis of each matrix) as a function of the spatial overlap of these labels in a sample (X axis of each matrix). In the matrix, 0% overlap denotes simulations with spatially distinct fluorophores, where each pixel corresponds to a single fluorophore, while simulations with 100% overlap contain, in every pixel, a randomized ratio of the n extrinsic and intrinsic fluorophores. Each one of the values reported in a matrix is the average of a 1024×1024×32 pixels simulation and shows the RMSE improvement of HyU to LU. Columns in the figure represent RMSE improvement matrices with 3× denoising filters across an increasingly binned number of spectral channels (32, 16, 8, 6, 4) applied with a total number of photons per pixel at (A) 16 (B) 32 (C) 48. When utilizing 32 spectral channel data, RMSE improvements reach up to the previously reported 100% for highly overlapping fluorophores. Successively increasing the binning across the wavelength dimension (and therefore decreasing the number of channels) shows a slow downward trend of the RMSE improvement until the 4 spectral channel matrices, where the RMSE improvement drops drastically down to below 25%, especially for more than 3 labels. Spectra utilized for this simulation are reported in FIG. 26B.
Figure 26:
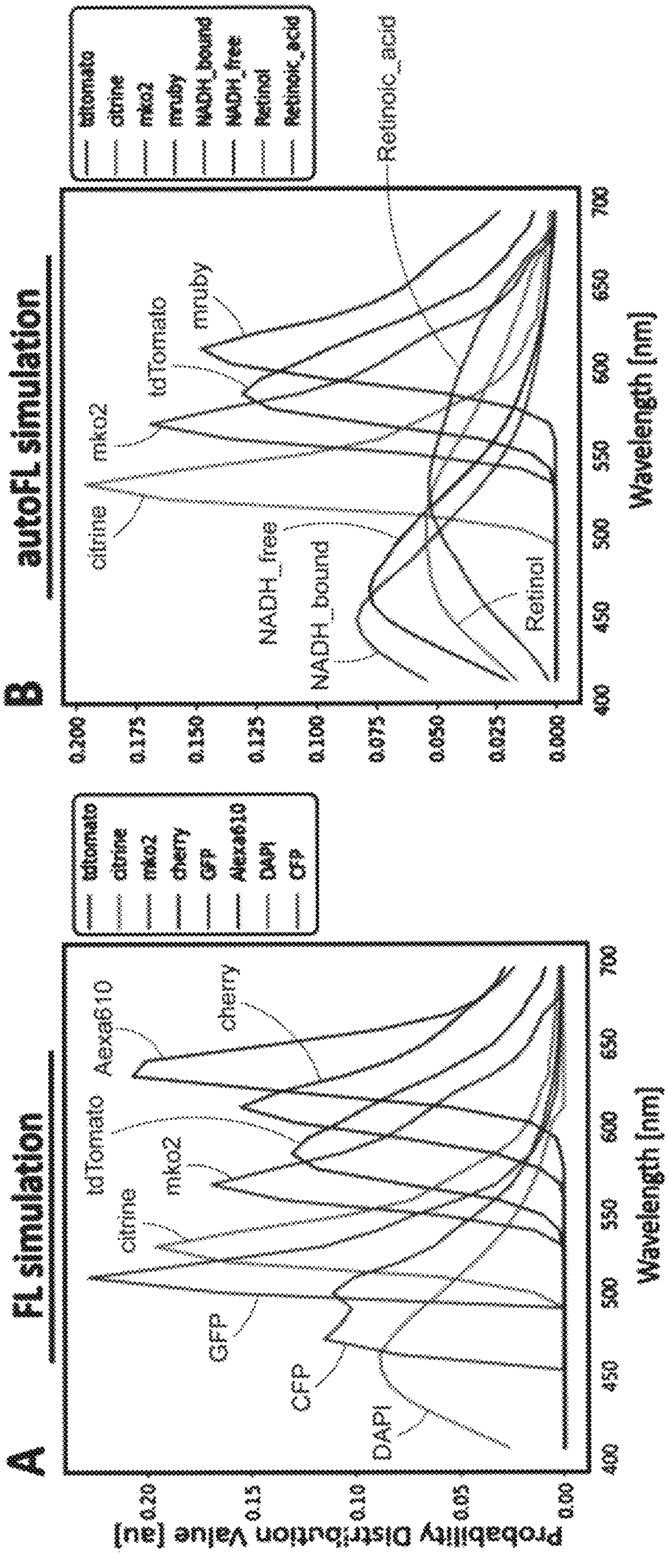
FIG. 26 illustrates an emission spectra of components in overlapping simulation. (A) Emission spectra from 8 fluorophores including tdTomato, Citrine, mKO2, mCherry, GFP, Alexa610, DAPI, and CFP used for Fluorescence (FL) overlapping simulations. (B) Emission spectra from 8 extrinsic and intrinsic fluorophores including tdTomato, Citrine, mKO2, mRuby, NADH bound, NADH free, Retinol, and Retinoic acid used for autofluorescence (autoFL) overlapping simulations.
Figure 27:
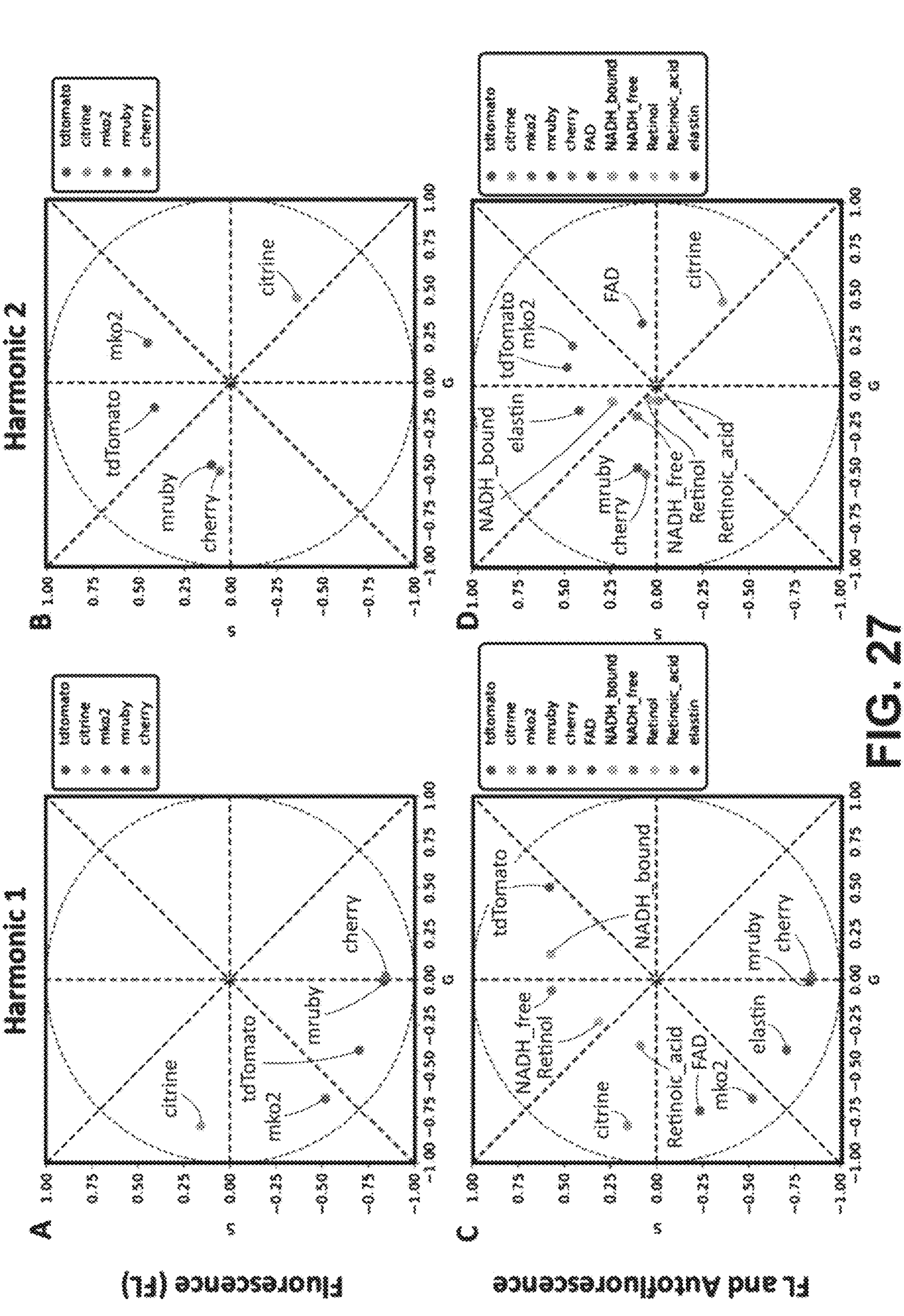
FIG. 27 illustrates pre-identified positions for common fluorophores on the phasor map. (A) Pre-identified extrinsic label positions (g,s) are denoted on the phasor plot for the first harmonic and (B) second harmonic. (C) Intrinsic label locations are further added on the phasor plot for the first harmonic and (D) second harmonic. Second harmonic generally covers a larger portion of the phasor space compared to the first harmonic. However, in the case of intrinsic signals, the locations of the pure autofluorescence spectra are on average more separated when utilizing the first harmonic. Details on the source of the pure spectra for these locations are reported in Methods—Independent Spectral Signatures.
Figure 30:
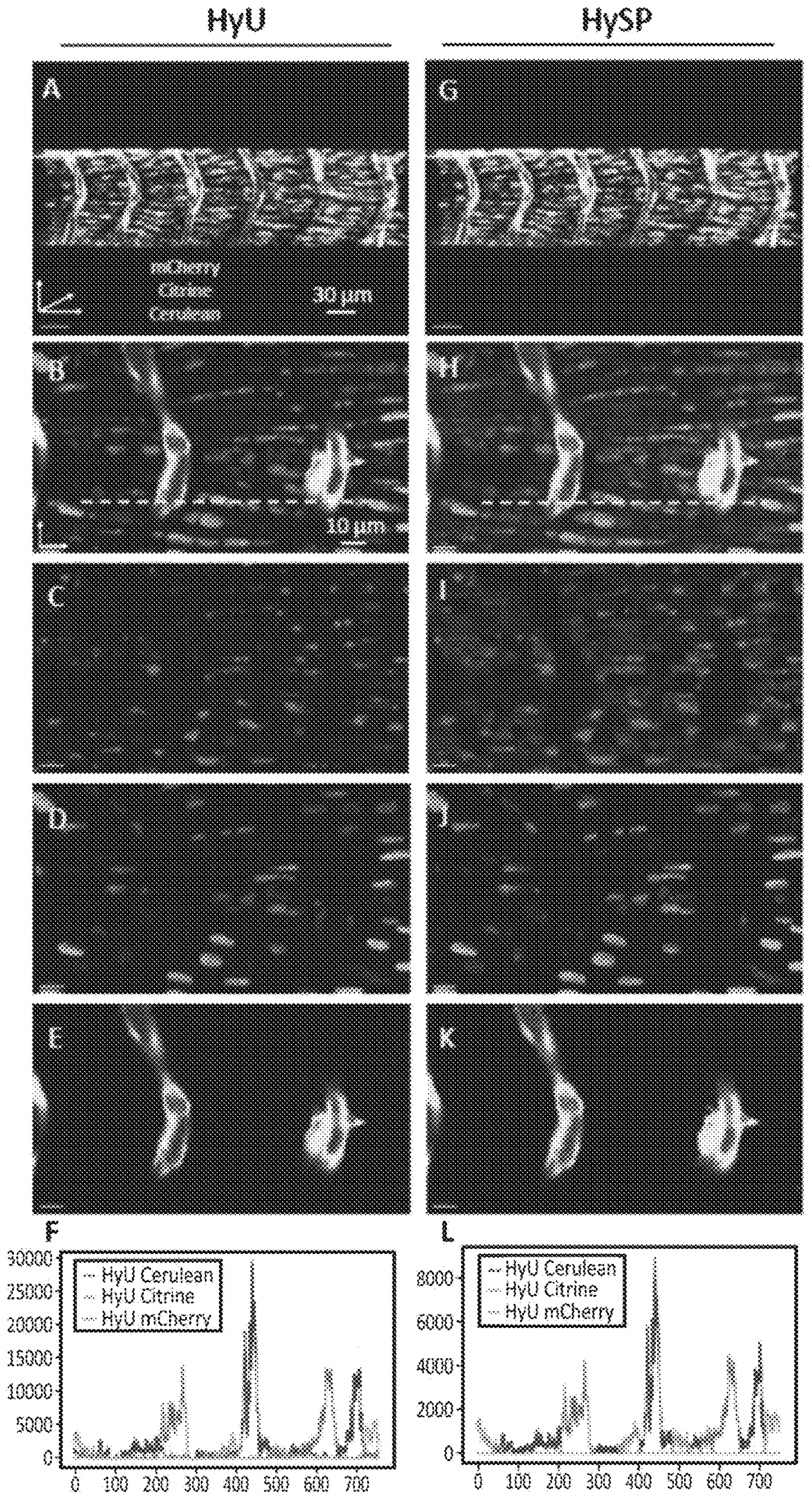
FIG. 30 illustrates an example comparison of HyU vs. Hyperspectral Phasors (HySP) results from a spectrally overlapping and spatially disperse sample. Results are presented for unmixing using HyU and HySP on a spectrally overlapping spatially disperse dataset collected from a tri-labeled transgenic zebrafish embryo obtained by injecting mRNA-encoding H2B-cerulean (cyan) in double transgenic embryos Gt(desm-citrine) ct122a/+;Tg(kdrl:eGFP) (magenta and yellow, respectively) (A-F) HyU unmixing results and (G-L) HySP unmixing results renderings for the dataset. Line profiles of (F) HySP (L) HyU analysis results (B, H dashed line) show the similarity in signal between the two methods for all channels within a non-overlapping sample. (A,F) Volumetric images show a similarity between the HyU and HySP results. This is further demonstrated for the results in a (B,H) single z-slice, for just the (C,I) Citrine channel, the (D,J) Cerulean channel, and the (E,K) mCherry channel. (F,L) Line profiles for the lines shown in B and H, respectively, also demonstrate the similar results of HyU and HySP for spatially non-overlapping samples.
Figure 36:
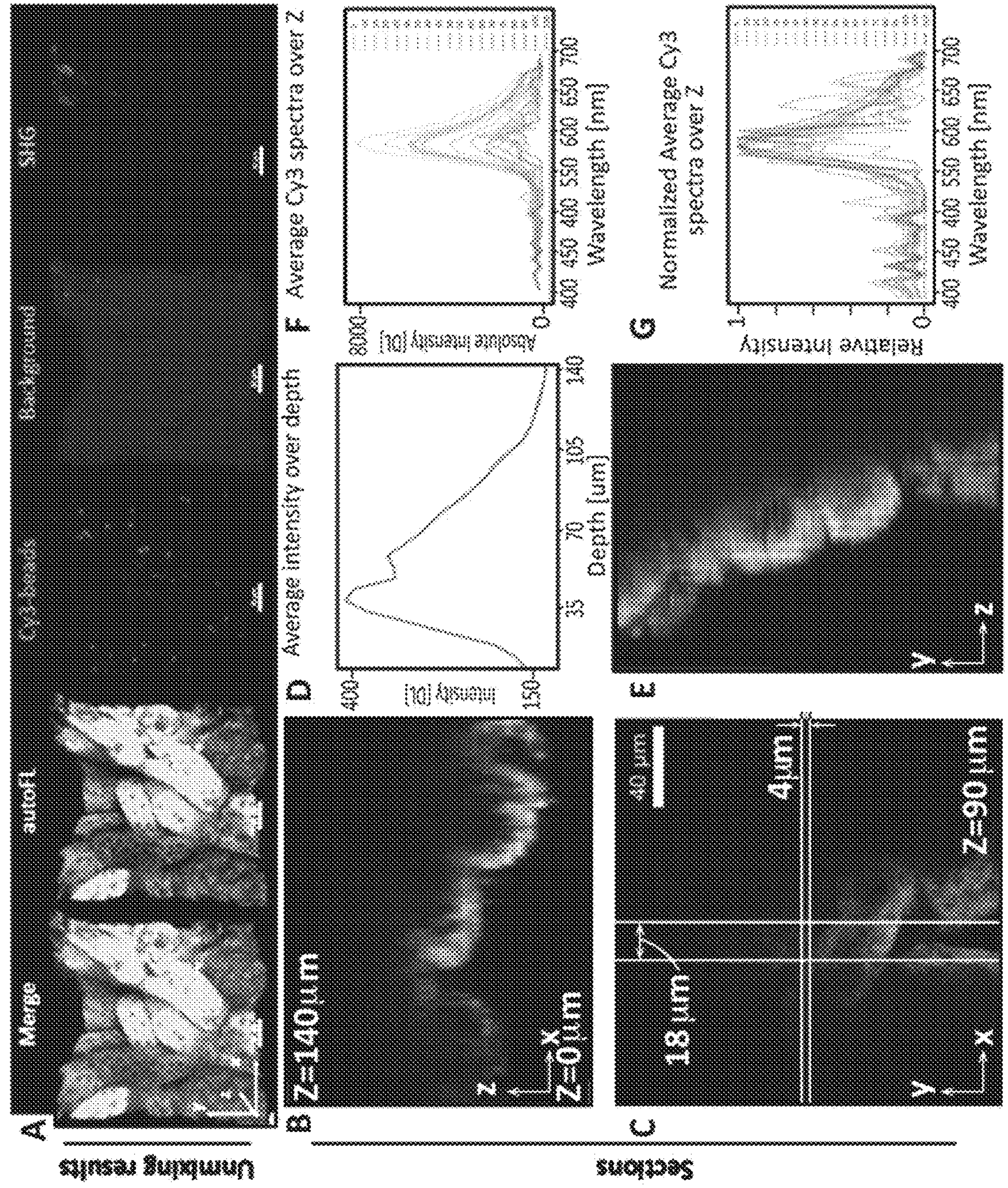
FIG. 36 illustrates extrinsic fluorescent signatures in fixed mouse tissue. The performance of HyU was evaluated in imaging fluorescent signals in a highly scattering fixed kidney tissue of a 7-month-old Balb-c mouse with embedded Cy3 fluorescent beads (Methods) imaged with 2-photon 850 nm excitation up to 150 μm deep. (A) Volumetric rendering of the unmixing results of the signals from fixative autofluorescence (autoFL), Cy3 beads, background, and Second Harmonic Generation (SHG). (B-E) Orthogonal views of the same volume for (C) single (x,y) plane of the volume at a depth of 90 μm with cross-sections (yellow hairlines in C) (B) (z,x) of 18 μm and (E) (y,z) of 4 μm respectively showing sections of the unmixed volume containing Cy3 beads at different depths up to 140 μm. (D) Average intensity value for each acquired (x,y) spectral image slice as a function of depth reveals considerable loss of fluorescent signal deeper than 110 μm. (F) Average spectra for each z-plane containing pixels with Cy3 beads signal plotted with absolute intensity (Digital Levels, DL) show decreasing intensity with depth as visible by the area under spectrum. (G) The same averaged spectra are normalized and plotted with Relative Intensity to show the consistency in the spectral shape as a function of depth in reference to Cy3 beads in solution (dashed line).

HyU improvement is related to the presence of various types of signal disruption and noise in microscopy images, such as stochastic emission, Gaussian, Poisson and digital as well as unidentified sources of spectral signatures which affect SNR in a variety of ways (FIGS. 11B-C, 12G, 34). In the multiplexing of fluorescent signals, HyU offers improved performance, quality- and speed-wise in the low-signal regime. HyU improves over previously disclosed phasor analysis (FIGS. 30,31, and Example 25) and the current gold standard conventional LU under multiple experimental conditions of low SNR (FIGS. 22-23) reduced number of channels (FIGS. 24-25) in the case of fluorescent signals as well as combination of multiple fluorescent and autofluorescent signals (FIG. 26). HyU is poised to be used in the context of in vivo imaging, harvesting information from samples labeled at endogenous-level even in scattering mammal samples (FIGS. 35-36).

The results of this example, quantitatively show that HyU, a phasor based, computational unmixing framework, may be well suited in tackling many challenges present in live imaging of multiple fluorescence labels. HyU's reduced requirements in amount of fluorescent signal permit a reduction of laser excitation load and imaging time. These features of HyU may enable multiplexed imaging of biological events with longer duration, higher speed and lower phototoxicity while providing access to information-rich imaging across different spatio-temporal scales. The reduced requirements of HyU may make it fully compatible with any commercial and common microscopes capable of spectral detection, facilitating access to the technology.

The present disclosure provides examples which demonstrate HyU's robustness, simplicity and improvement in identifying both new and known spectral signatures, and vastly improved unmixing outputs, providing a much-needed tool for delving into the many questions still surrounding studies with live imaging.

Example 3. Zebrafish Sample Preparation

Transgenic zebrafish lines were intercrossed over multiple generations to obtain embryos with multiple combinations of the transgenes. All lines were maintained as heterozygous for each transgene. Embryos were screened using a fluorescence stereo microscope (Axio Zoom, Carl Zeiss) for expression patterns of individual fluorescence proteins before imaging experiments. A confocal microscope (LSM 780, Carl Zeiss) was used to isolate Tg(ubiq:Lifeact-mRuby) lines from Tg(ubiq:lyn-tdTomato) lines by distinguishing spatially- and spectrally-overlapping signals.

For in vivo imaging, 5-6 zebrafish embryos at 18 to 72 hpf were immobilized and placed into 1% UltraPure low-melting-point agarose (catalog no. 16520-050, Invitrogen) solution prepared in 30% Danieau (17.4 mM NaCl, 210 M KCl, 120 M MgSO47H2O, 180 M Ca(NO3)2, 1.5 mM HEPES buffer in water, pH 7.6) with 0.003% PTU and 0.01% tricaine in an imaging dish with no. 1.5 coverglass bottom, (catalog no. D5040P, WillCo Wells). Following solidification of agarose at room temperature (1-2 min), the imaging dish was filled with 30% Danieau solution and 0.01% tricaine at 28.5° C.

Example 4. Fluorescent Silica Beads Characterization

One fluorescent silica beads solution (Nanocs, Inc.) labeled with Cy3 (Si500-S3-1, 0.5 mL, 1% solid, lot #1608BRX5) was characterized in its spectral fluorescence emission and physical size.

10× dilution in PBS of the beads was placed on a no. 1.5 imaging coverglass and spectrally characterized using spectral mode on a Zeiss LSM 780 laser confocal scanning microscope equipped with a 32-channel detector using 40×/1.1 W LD C-Apochromat Korr UV-VIS-IR lens utilizing a 2-photon laser at 740 nm to excite fluorescence from the beads, using a 690 nm lowpass filter to separate excitation and fluorescence. Spectra obtained from multiple beads with the same label were averaged, producing the reference spectrum reported in FIG. 36G (dashed line). Fluorescent silica bead size and concentration were determined via nanoparticle tracking analysis (NTA) on the Nanosight NS300 (Malvern Panalytical). Samples were run 5 times and results averaged for final size and concentration values reported.

Example 5. Mouse Sample Preparation

For autofluorescent measurements, mouse organ samples were collected from Balb-c mice. Following euthanasia, organs were resected and washed in Phosphate Buffered Saline (PBS) to remove residual blood and kept in PBS until imaging preparation. Organs were sectioned in order to image the internal architecture and mounted on a glass imaging dish with sufficient PBS to avoid dehydration of the sample. Following imaging, all samples were fixed in a 10% Neutral Buffered Formalin solution at 4° C.

For ex vivo bead characterization in tissue, mouse organ samples were collected from Balb-c mice. Following euthanasia, organs were resected and washed in PBS followed by incubation for at least 24 hours in 10% buffered formalin. The kidney was then removed from the fixative and sectioned into smaller ~5×5×5 mm pieces for imaging. A fluorescent silica beads working solution (Nanocs, Inc.) labeled with Cy3 (Si500-S3-1, 0.5 mL, 1% solid, lot #1608BRX5) and previously characterized was prepared using a 10× dilution of the fluorescent beads from their stock concentration. Beads were injected in the sample using 50 ul of the solution loaded into a 0.5 mL syringe with a 28 g needle. The kidney sections were then placed in imaging dishes with a small volume of PBS to keep the samples hydrated prior to imaging.

Example 6. Image Acquisition

Images were acquired on a Zeiss LSM 780 laser confocal scanning microscope equipped with a 32-channel detector using 40×/1.1 W LD C-Apochromat Korr UV-VIS-IR lens at 28° C.

Samples of Gt(cltca-Citrine), Tg(ubiq:lyn-tdTomato), Tg(fli1::mKO2), and Tg(ubiq:Lifeact-mRuby), were simultaneously imaged with 488 nm and 561 nm laser excitation, for citrine, tdTomato, mKO2, and mRuby. A narrow 488 nm/561 nm dichroic mirror was used to separate excitation and fluorescence emission. Samples were imaged with a 2-photon laser at 740 nm to excite autofluorescence, using a 690 nm lowpass filter to separate excitation and fluorescence.

Samples of mouse kidney tissue were imaged with 2-photon excitation at 740 nm or 850 nm with a 690+nm lowpass filter, at 37° C. incubation.

For all samples, detection was performed at the full available range (410.5-694.9 nm) with 8.9 nm spectral binning.

Example 7. Detailed Description of the Imaging Parameters Used for all Images of this Disclosure

TABLE 1

Example Imaging Parameters

| FIGS. | Label | Zebrafish Stage | Imaged volume [pixels] | Imaged volume [pixels] | Imaged volume [pixels] | Lateral pixel (x, y, res.) [μm] | Axial section (z res.) [μm] | Pixel dwell time [μs] | Laser Power |
|---|---|---|---|---|---|---|---|---|---|
| 2E-P, 13 | Gt(cltca-Citrine); Tg(ubiq:lyn-tdTomato; ubiq:Lifeact-mRuby; fli1:mKO2) | 10 dpf | 1024 | 1024 | 17 | 0.346 | 3.00 | 3.1 | 561 nm: 0.18% 488 nm: 5% |
| 3A F, 7, 14 | Gt(cltca-Citrine); Tg(ubiq:lyn-tdTomato; ubiq:Lifeact-mRuby; fli1:mKO2) | 2 dpf | 1024 | 512 | 31 | 0.415 | 5.00 | 3.1 | 561 nm: 0.6% 488 nm: 5.5% |
| 4 | Gt(cltca-Citrine); Tg(kdrl:mCherry; fli1: mKO2) | 5 dpf | 512 | 1024 | 26 | 0.461 | 3.00 | 2.5 | 561 nm: 2% 488nm: 4% |
| 5A, 8 | Gt(cltca-Citrine); Tg(ubiq:lyn-tdTomato; ubiq:Lifeact-mRuby) | 3 dpf | 2304 | 512 | 27 | 1.38 | 5.00 | 5.0 | 561 nm: 0.4% 488 nm: 2.8% |
| 5B-D | Gt(cltca-Citrine); Tg(ubiq:lyn-tdTomato; ubiq:Lifeact- | 3 dpf | 2560 | 2048 | 27 | 0.259 | 4.00 | 3.1 | 561 nm: 0.18% 488 nm: 5% |
| 5E-G, 32 | mRuby; fli1:mKO2) Plus strong autofl | | | | | | | | 740 nm: 4% |

TABLE 1-continued

Example Imaging Parameters

| FIGS. | Label | Zebrafish Stage | Imaged volume [pixels] | Imaged volume [pixels] | Imaged volume [pixels] | Lateral pixel (x, y, res.) [μm] | Axial section (z res.) [μm] | Pixel dwell time [μs] | Laser Power |
|---|---|---|---|---|---|---|---|---|---|
| 6, S9, 16, 17, 21 | Gt(cltca-Citrine); Tg(ubiq:lyn-tdTomato; ubiq:Lifeact-mRuby; fli1:mKO2) Plus strong autofl | 3 dpf | 768 | 512 | 17 | 0.923 | 4.00 | 6.3 | 561 nm: 0.4% 488 nm: 5% 740 nm: 3% |
| 18 | casper | 36 hpf | 6144 | 1536 | 25 | 0.461 | 6.00 | 3.1 | 740 nm: 3% |
| 28 | Wildtype | 22 hfp | 512 | 512 | 23 | 0.078 | 2 | 3.1 | 740 nm: 2.8% |
| 29, 33 | Tg(ubiq:lyn-tdTomato) | 18 hpf | 1024 | 1024 | 40 | 0.231 | 2 | 3.1 | 561 nm: 0.04% |
| 30C | Gt(desm-citrine) ct122a/+; Tg(kdrl:eGFP) | 3 dfp | 2560 | 2048 | 29 | 0.277 | 5 | 3.1 | 561 nm: 0.1% |
| 31 | Gt(cltca-Citrine); Tg(fli1:mKO2) | 5 dfp | 1024 | 1024 | 30 | 0.346 | 2 | 3.1 | 561 nm: 0.4% 488 nm: 4.5% |
| 35 | Balb-c mice | 7 months | 973 | 512 | 31 | 0.277 | 5 | 6.27 | 740 nm: 3.5% |
| 36 | Balb-c mice | 7 months | 512 | 512 | 28 | 0.346 | 5 | 6.27 | 850 nm: 4% |

*hpf = hours post fertilization
*dpf = days post fertilization

Example 8. Hyperspectral Fluorescence Image Simulation

The model simulates spectral fluorescent emission by generating a stochastic distribution of photons with profile equivalent to the pure reference spectra (as described in Example 22). The effect of photon starvation, commonly observed on microscopes, is synthetically obtained by manually reducing the number of photons in this stochastic distribution. Detection, Poisson and signal transfer noises are then added to produce 32-channel fluorescence emission spectra that closely resemble those acquired on microscopes. The simulations include accurate integration of dichroic mirrors and imaging settings.

Experimentally matching simulations. To quantify the performance of HyU vs LU for microscopy data acquired experimentally, synthetic data were generated where each input spectra was organized with intensity distributions taken from experimental data. The analog to photon counting rate was calibrated based on existing literature. Real data was discretized to photons to produce a realistic photon mask with biologically relevant distribution of signal. This provided intensities and ratios which would match those acquired from the microscope while allowing us control over the effects of photon starvation.

Overlapping simulations. Simulations to quantify the performance of HyU vs. the conventional LU with respect to the number of spectral combinations are included. These simulations were created with artificial intensity distributions so that a simulation with X % overlap and n fluorophores would have a specific percentage of pixels, X, with a randomized ratio of n input spectra. As an example, for a simulation with 6 fluorophores and 50% overlap, the simulated dataset would have 50% of the pixels contain a randomized combination of the 6 fluorophores, while the remaining pixels contain a single fluorophore. This allowed us to investigate the effects of an increasing number of spectral combinations on the compressive nature of the phasor method for HyU.

Example 9. Image Analysis: Independent Spectral Signatures

Independent spectral fingerprints can be obtained through samples, solutions, literatures, or spectral viewer websites (Thermo fisher, BD spectral viewer, Spectra analyzer). Fluorescent signals used in this paper were obtained by imaging single labelled samples in areas morphologically and physiologically known to express the specific fluorescence, see FIG. 27. For each dataset a phasor plot was computed. The 32-channel spectral fingerprint was extracted from the phasor-bin at the counts-weighted average position of the phasor cluster. Those fingerprints were compared with literature fingerprints and manually corrected to reduce noise. Further descriptions for how to identify new components can be found in Example 22 and FIGS. 17, 23.

For autofluorescent signals, spectrum for Elastin was obtained experimentally and compared with literature. Spectra for Nicotinamide Adenine Dinucleotide (NADH) free, NADH bound, Retinoic acid, Retinol and Flavin Adenine Dinucleotide (FAD) were acquired from in vitro solutions using the microscope. NADH free from B-Nicotinamide Adenine Dinucleotide (Sigma-Aldrich, St. Luis, MO, #43420) in Phosphate Buffered Saline (PBS) solution. NADH bound from B-Nicotinamide Adenine Dinucleotide and L-Lactic Dehydrogenase (Sigma-Aldrich, #43420, #L3916) in PBS. Retinoic acid from a solution of Retinoic Acid (Sigma-Aldrich, #R2625) in Dimethylsulfoxide (DMSO). Retinol from a solution of Retinol synthetic (Sigma-Aldrich, #R7632) in DMSO. FAD from Flavin Adenine Dinucleotide Disodium Salt Hydrate (Sigma-Aldrich, #F6625) in PBS.

Example 10. Phasor Analysis

For each pixel in a dataset, the Fourier coefficients of its normalized spectra define the coordinates (G(n),S(n)) in the phasor plane, where:

$$G(n)=\frac{\sum_{\lambda_s}^{\lambda_f} I(\lambda)\cos(n\omega\lambda)\Delta\lambda}{\sum_{\lambda_s}^{\lambda_f} I(\lambda)\Delta\lambda} \quad (1)$$

$$S(n)=\frac{\sum_{\lambda_s}^{\lambda_f} I(\lambda)\sin(n\omega\lambda)\Delta\lambda}{\sum_{\lambda_s}^{\lambda_f} I(\lambda)\Delta\lambda} \quad (2)$$

$$\omega=\frac{2\pi}{c} \quad (3)$$

Where $\lambda_s$ and $\lambda_f$ are starting and ending wavelengths respectively; I is the measured intensity; c is the number of spectral channels (32 in the present case), and n the harmonic number. The first harmonic (n=1) is utilized for the autofluorescent signals and the second harmonic (n=2) for fluorescent signals based on the sparsity of independent spectral components. A two-dimensional histogram with dimensions (S, G) is applied to the phasor coordinates in order to group pixels with similar spectra within a single square bin. This process can be defined as phasor encoding.

Example 11. Linear Unmixing

The hypothesis for linear unmixing in this work is that given i independent spectral fingerprints (fp), each collected spectrum (I(λ)) is a linear combination of fp, and the sum of each fp contribution (R) is 1.

$$I(\lambda)=W_1R_1fp_1+W_2R_2fp_2+\cdots+W_iR_ifp_i+N \quad (4)$$

$$\sum R_i=1 \quad (5)$$

where $R_i$ is the ratio, $W_i$ the weight, and N the noise. The acquired spectra are collected in the original spectral cube with shape (t,z,c,y,x), with t as time, c as channel and x,y,z spatial dimensions.

i spectral vectors, $fp_i$, need to be provided to the unmixing function. It is assumed that there are identical weights for all fp, and a low value for noise N. Under these conditions, $R_i$ is obtained by applying a Jacobian Matrix Inversion:

$$\begin{bmatrix} \sum_x w(x)\frac{\partial f^0}{\partial\alpha_1}\frac{\partial f^0}{\partial\alpha_1} & \sum_x w(x)\frac{\partial f^0}{\partial\alpha_1}\frac{\partial f^0}{\partial\alpha_2} & \cdots \\ \sum_x w(x)\frac{\partial f^0}{\partial\alpha_2}\frac{\partial f^0}{\partial\alpha_1} & \sum_x w(x)\frac{\partial f^0}{\partial\alpha_2}\frac{\partial f^0}{\partial\alpha_2} & \cdots \\ \vdots & \vdots & \ddots \end{bmatrix}\begin{bmatrix}\alpha_1-&\alpha_1^0\\ \alpha_2-&\alpha_{2^0}\end{bmatrix}= \quad (6)$$

-continued $$\begin{bmatrix} \sum_x w(x)\left[y(x)-f^0(x)\right]\frac{\partial f^0}{\partial\alpha_1} \\ \sum_x w(x)\left[y(x)-f^0(x)\right]\frac{\partial f^0}{\partial\alpha_1} \\ \sum_x w(x)\left[y(x)-f^0(x)\right]\frac{\partial f^0}{\partial\alpha_1} \end{bmatrix}$$

In the pixel-by-pixel linear unmixing implementation in this work, the Jacobian Matrix inversion is applied on the acquired spectrum in each pixel with dimensions (t,z,c,y,x). Resulting ratios for each spectral vector are assembled in the form of a ratio cube with shape (t,z,i,y,x) where x,y,z,t are the original image spatial and time dimensions, respectively and i is the number of input spectral vectors. The ratio cube (t,z,i,y,x) is multiplied with the integral of intensity over channel dimension of the original spectral cube, with shape (t,z,y,x), to obtain the final resulting dataset with shape (t,z,i,y,x).

Example 12. Hybrid Unmixing—Linear Unmixing

In the Hybrid Unmixing implementation, Jacobian Matrix Inversion is applied on the average spectrum of each phasor bin with dimensions (c,s,g) where g and s are the phasor histogram sizes and c is the number of spectral channels acquired. The average spectrum in each bin is calculated by using the phasor as an encoding, to reference each original pixel spectra to a bin. Resulting ratios for each component channel are assembled in the form of a phasor bin-ratio cube with shape (i,s,g) where i is the number of input independent spectra fp (Linear Unmixing section). This phasor bin-ratio cube is then referenced to the original image shape, forming a ratio cube with shape (t,z,i,y,x) where x, y, z, t are the original image dimensions. The ratio cube is multiplied with the integral of intensity over channel dimension of the original spectral cube, with shape (t,z,y,x), obtaining a final result dataset with shape (t,z,i,x,y).

Example 13. Unmixing Algorithms Used for Speed Comparisons

Unmixing algorithms utilized for speed comparisons with the HyU algorithm (FIG. 19) were plugged in the unmixing step of the analysis pipeline and sourced as follows. Non-negative Constrained Least Squares and Fully Constrained Least Squares from pysptools.abundance_maps (https://pysptools.sourceforge.io/abundance_maps.html). Robust Non-Negative Matrix Factorization[10] python implementation was obtained from (https://github.com/neel-dey/robst-nmf).

Example 14. Data Visualization

Rendering of final result datasets were performed using Imaris 9.5-9.7. In FIGS. 2-3, contrast settings (minimum, maximum, gamma) for each channel were set to be equal to provide reasonable comparison between HyU and LU results. Gamma was set to 1, no minimum threshold was applied, and the maximum for each channel was set to ⅓ of the maximum intensity. The images were rendered using Maximum Intensity Projection (MIP), and for improving display, they were digitally resampled in the z-direction, maintaining a fixed xy ratio to attenuate the gap generated from sparse sampling z-wise on the microscope.

Example 15. Box Plot Generation

All box plots were generated using standard plotting methods. The center line corresponds to the median, the lower box border corresponds to the first quartile, and the upper box border corresponds to the third quartile. The lower- and upper-whiskers correspond to one and a half times the interquartile range below and above the first and third quartiles respectively.

Example 16. Timelapse Registration

A customized python script (Supplementary Code) was first utilized to pad the number of z slices across multiple time points, obtaining equally sized volumes. The "Correct 3D drift" plug (https://imagej.net/Correct_3D_Drift) in FIJI (https://imagej.net/Fiji) was used to register the data.

Example 17. Timelapse Statistics

Box plots and line plots for timelapses were generated using ImarisVantage in Imaris 9.5-9.7. Box plot elements follow the same guidelines as described above. Line plots are connected box plots for each time point with the solid line denoting the median values, and the shaded region denoting the first and third quartiles.

Example 18. Mean Square Error

For synthetic data, a ground truth is available for comparison of unmixing fidelity between HyU and LU. fp contributions, or ratios, were used for quantification, owing to the arbitrary nature of intensity values in microscopy data. Mean Square Error (MSE) is used for determining the quality of the ratios in synthetic data. MSE can be defined as the square difference of the ratio recovered by an unmixing algorithm ($r_{unmixed}$) and the ground truth ratio (r) divided by the total number of pixels (n).

$$MSE = \frac{1}{n}|r_{unmixed} - r|^2 \tag{7}$$

To simplify comparison between different unmixing algorithms, Relative Mean Square Error (RMSE) can be defined as:

$$RMSE = \left(\frac{MSE_{LU}}{MSS_{HyU}} - 1\right) * 100\% \tag{8}$$

RMSE measures the improvement in MSE when using HyU as compared to the conventional LU.

Example 19. Residuals

For experimental data, in the absence of ground truth, the performance of the results returned by the unmixing algorithms are quantified with the following measurements: Average Relative Residual, Residual Image Map, Residual Phasor Map, and finally, Residual Intensity Histogram.

Residual (R) is calculated as:

$$\text{For image: } R(x, y, c, z, t) = I_{Raw\ Image}(x, y, c, z, t) - I_{Unmixed\ Image}(x, y, c, z, t) \tag{9}$$

$$\text{For phasor: } R(g, s, c) = I_{Raw\ Image}(g, s, c) - I_{Unmixed\ Image}(g, s, c) \tag{10}$$

The spectral intensity difference between the unmixed image and original image for each pixel or phasor bin depend on the following descriptions of the intensity image (I), where:

$$I_{Raw\ Image} = \sum_i r * fp_i + N \tag{11}$$

$$I_{Unmixed\ Image} = \sum_i r_{unmixed} * fpi \tag{12}$$

The original spectrum ($I_{Raw\ Image}$) is the combination of each independent spectral component (fp) with its ratio (r) plus noise (N). The recovered spectrum is obtained by the multiplication of recovered ratios ($r_{unmixed}$) with each corresponding individual component.

Relative Residual (RR) is calculated as the sum of the residual values over C channels and normalized to the sum of the original intensity values over C channels (with C=32 in for example).

$$RR(x, y, z, t) = \frac{\sum_{C=1}^{C} R(x, y, c, z, t)}{\sum_{C=1}^{C} I_{Raw\ Image}(x, y, c, z, t)} \tag{13}$$

$$RR(g, s) = \frac{\sum_{c=1}^{C} R(q, s, c)}{\sum_{c=1}^{C} I_{Raw\ Image}(q.s.c)} \tag{14}$$

The Average Relative Residual (FIG. 11) provides a single comparison value for evaluating the performance of different processing methods on the same data, such as the application of multiple filters, applying of various threshold values, and variations in the number of components estimated. Average Relative Residual ($RR_{avg}$) is defined as the average of the relative residual for every pixel in the image or every phasor bin in the phasor histogram.

$$\text{For image: } RR_{avg} = \frac{\sum_t \sum_z \sum_y \sum_x RR}{xyzt} \tag{15}$$

$$\text{For phasor: } RR_{avg} = \frac{\sum_s \sum_g RR}{gs} \tag{16}$$

The Residual Image Map visualizes the residual values for each pixel of the image (FIG. 10). Regions with higher residual values appear to characterize portions of the dataset with increased amount of noise or where an unexpected spectral signature is present.

Residual Image Maps ($R_{img\ map}$(x,y)) project the Relative Residual (RR) cube to the 2D image shape for each voxel, providing an estimated visualization of an algorithm ratio recovery performance in the spatial context of the original image.

$$R_{img\ map}(x, y) = \sum_{z,t} RR(x, y, z, t) * 100 \tag{17}$$

Residual Phasor Map visualizes residuals for each bin of the phasor histogram (FIG. 10). These maps allow for insights on where HyU unmixing results have reduced performance in phasor domain and indicate phasor locations of unexpected additional spectral components (FIG. 11).

$$R_{ph\ map}(g, s) = RR(g, s) * 100 \tag{18}$$

The Residual Intensity Histogram $R_{Int\ Hist}$(p,rr) (FIGS. 3 *g,h*, and 10*d*) calculates the distribution of the relative residual in relation to intensity overall all pixels or all phasor bins. Higher residuals appear to be present in regions with lower signal intensity and SNR, providing degraded performance.

$$\text{For image: } R_{Int\ Hist}(p, rr) = \text{count}(P(x, y, z, t), RR(x, y, z, t))_{p,rr} \tag{19}$$

$$\text{For phasor: } RR_{Int\ Hist}(p, rr) = \text{count}(P(g, s), RR(g, s))_{p,rr} \tag{20}$$

$$P = \frac{\sum_{c=1}^{C} I_{Raw\ Image}}{4 * sf} \tag{21}$$

Where p is a bin of the histogram P, rr is a bin of RR, and sf is the factor which converts the number of photons to digital intensity levels.

Example 20. Image Contrast

Image contrast measures the distinguishability of a detail against the background. Percent contrast can refer the relationship between the highest and lowest intensity in the image.

$$\text{Contrast} = \frac{I_s - I_B}{I_B} \tag{22}$$

Where the Intensity of signal average (Is) is the average of top 20% intensities in the image. The Intensity of background average (IB), the average of bottom 20% image intensities.

Example 21. Spectral Signal to Noise Ratio

Since each synthetic dataset has a ground truth, the SNR can be calculated by comparing the simulated image to the ground truth. Since these are hyperspectral images, the definition of SNR can be extended to the wavelength dimension of the data and use the term Spectral SNR. Two types of Spectral SNR can include Absolute Spectral SNR and Relative Spectral SNR.

Spectral SNR can be calculated as follows for each single spectrum simulation. First, for each pixel and channel, the absolute value of the difference is taken between the ground truth intensity and the simulated intensity. Then the mean is calculated over all of the pixels for each channel. Finally, the sum is taken over all of the channels and divided by either 32 for the absolute SNR, or the number of channels with signal for the relative SNR. The number of channels with signal is calculated by checking if there is a statistically significative number of pixels in a single channel with a pixel SNR value greater than zero.

$$\text{Absolute } SNR = \frac{\sum_{c=1}^{32} \frac{\sum_{n=1}^{P} \frac{i_{gnd}}{i_{sim} - i_{gnd}}}{P}}{32} \tag{23}$$

$$\text{Relative } SNR = \frac{\sum_{c=1}^{C} \frac{\sum_{n=1}^{P} \frac{i_{gnd}}{i_{sim} - i_{gnd}}}{P}}{C} \tag{24}$$

Where $i_{gnd}$ is the intensity per pixel per channel for the ground truth data, $i_{sim}$ is the intensity per pixel per channel for the simulated (noisy) data, P is the total number of pixels, and C is the number of channels with signal.

Example 22. Identification of Spectra and New Components with HyU

Figure 17:
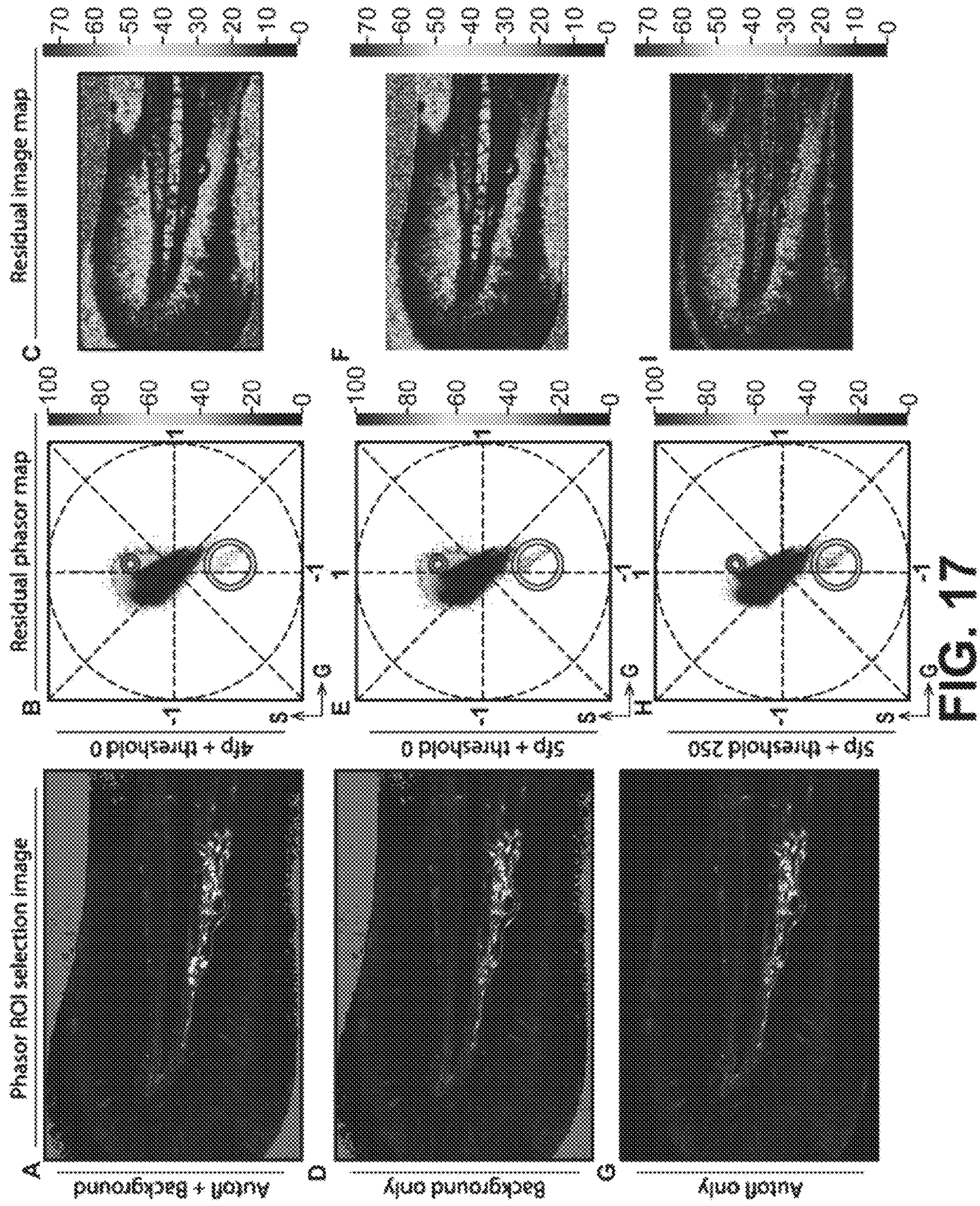
FIG. 17 illustrates a residual maps which can facilitate identification of independent spectral components. Experimental fluorescence microscopy data often includes unexpected autofluorescence signals. Residual Maps (Methods) provide additional information to account for these signals and properly adjust HyU analysis. (A) Average intensity image with pixels pseudo-colored in cyan (autofluorescence) and magenta (background) according to the ROIs selections on the (B) Residual Phasor Map, computed from the HyU of 4 input spectra with a threshold of zero. The pseudo-colored areas of the image match those presenting high residual values in the (C) Residual Image Map. Changing the unmixing input to include the unexpected autofluorescent spectrum (cyan) and performing the Residual Phasor map selections produces the (D) background pseudo-colored (magenta) image. The inclusion of autofluorescence as an independent spectral component in the unmixing decreases the number of pixels corresponding to the autofluorescent signal (cyan ROI) in the (E) Residual Phasor Map, thereby matching with the (F) Residual Image Map, which no longer presents high residuals in the center portion of the image. Increasing the threshold to 250 removes the pixels with high residuals corresponding to the background, removing them from the (G) average intensity image, (H) Residual Phasor Map, and (I) Residual Image Map.

Identification of independent spectral components has been an adversity for unmixing hyperspectral data. First, the collected spectra may be distorted by reduced SNR. Secondly, excitation of intrinsic signals causes uncertainty of biological sample. Favorably, HyU simplifies this process by adapting Phasor approach and achieving semi- or full-automation process for spectra identification and selection. In HyU, spectra can be loaded from an existing library, virtually automating the analysis process. Pre-identified cursors are generated from common fluorophores such as mKO2, tdTomato, mRuby, Citrine. Obtaining fluorescence spectra from experimental samples has some advantages compared to utilizing spectra from an existing library, as they account for a multitude of experimental and instrumental settings. Imaging settings such as different types of lenses or optical filters (FIGS. 10C-D) together with factors within the microenvironment of samples, such as pH or temperature have the potential to alter the fluorescence spectral emissions. In the presence of unexpected fluorescent signals, spectra can also be selected and visualized directly from the phasor. Phasors facilitate the identification of unexpected independent components and their distinction from the multiple system noises. A noise-free spectrum will appear as a single point on the phasor plot, while a spectrum affected by instrument and electronic noises will mainly appear as a gaussian distribution, centered on the original spectral signal. Conversely, a randomized noise across the multiple spectral channels will not produce a clustered aggregate of spectra on the phasor. A constant spectral noise, with a distinct spectrum (e.g. a constant light leakage into the system), would produce a distinct phasor cluster and could be selected for unmixing. The phasor plot representation is a 2D-histogram and provides insights into the frequency of occurrence for these signals. These unexpected independent components in samples often appear as "tails" on the phasor distributions (FIG. 17C). In the example HyU graphical interface, clicking on the phasor visualizes the spectra within a small area (9×9 bins by default, with size adjustable from the interface) of the phasor histogram (FIG. 1D). The examples shown and/or discussed in FIGS. 15-17, identify 5 distinct endmembers on the Phasor (FIG. 16C), visualize their spectra identifying Citrine, mRuby, Td-Tomato, mKO2, and one strong autofluorescence signature. The use of Residual Phasor Map (FIG. 17B) allows for identification of areas in the phasor with high amount of residuals, likely corresponding to a missing endmember in the unmixing. Residual Image Maps (FIG. 17C) provide a rapid overview of residuals in the image data, for identification of location in the dataset of the missing endmember.

Example 23. HyU in Autofluorescent Data

Figure 23:
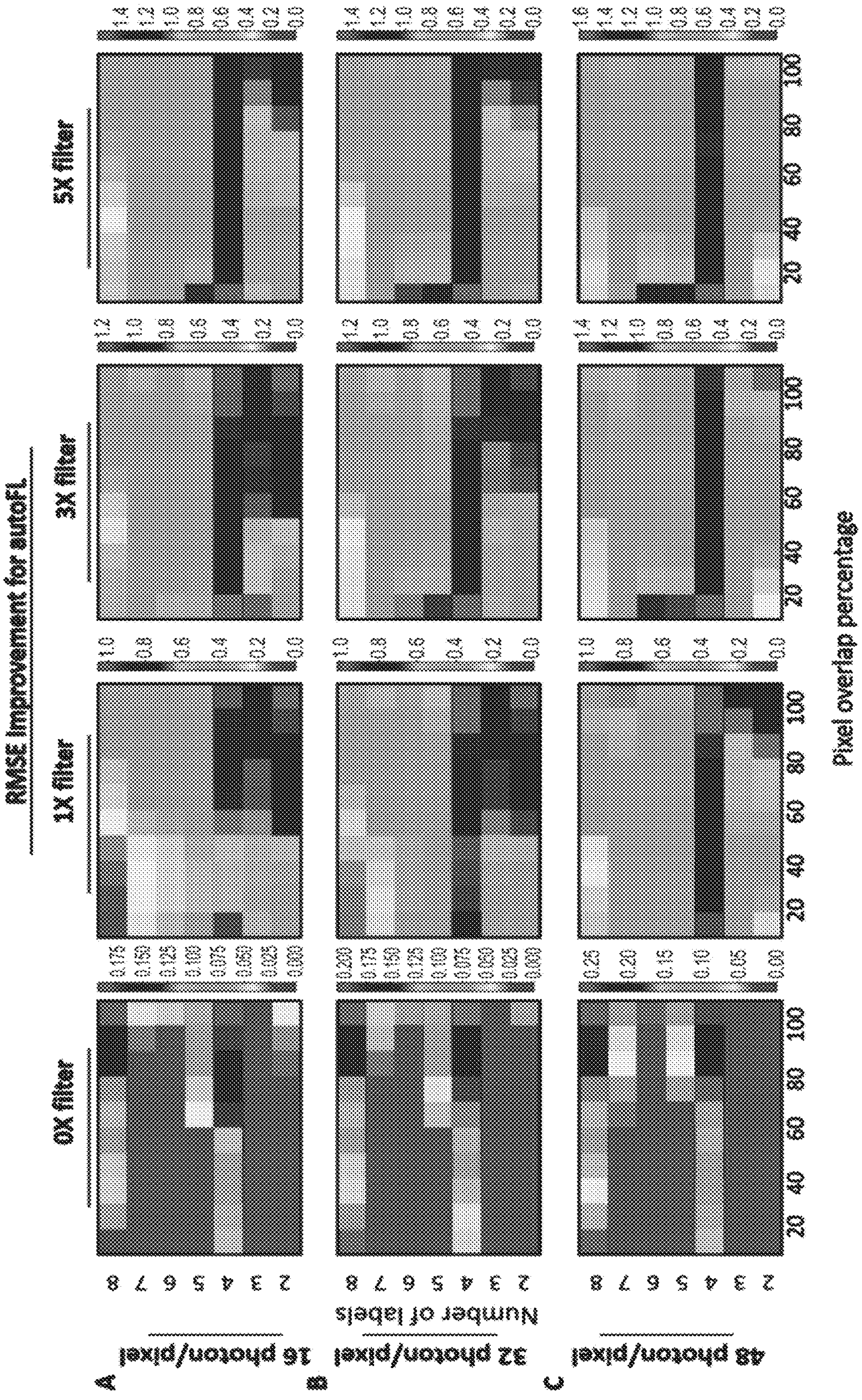
FIG. 23 illustrates an RMSE improvement for simulated fluorescent and autofluorescent spectral combinations which highlights increased HyU performance across multiple denoising filters. Twelve matrices demonstrate the RMSE improvement of HyU with respect to LU when unmixing a collection of synthetic data with 2 to 8 extrinsic and intrinsic labels (Y axis of each matrix) as a function of the spatial overlap of these labels in a sample (X axis of each matrix). In the matrix, 0% overlap denotes simulations with spatially distinct fluorophores, where each pixel corresponds to a single fluorophore, while simulations with 100% overlap have, in every pixel, a randomized ratio of the n extrinsic and intrinsic fluorophores. Each one of the values reported in a matrix is the average of a 1024×1024×32 pixels simulation and shows the RMSE improvement of HyU to LU. Different columns in the figure report the RMSE improvement matrices with different numbers of denoising filters (0×, 1×, 3×, 5×) applied with a total number of photons per pixel at (A) 16 (B) 32 (C) 48. In the absence of denoising filters, the improvement of HyU overall is less than 25%. Denoising filters improve RMSE by over 100%. Spectra utilized for this simulation are reported in FIG. 26B.

Cellular metabolism is a key regulator of cell function and plays an essential role in the development of numerous diseases. Understanding of cellular metabolic pathways is critical for the development and assessment of novel therapies and diagnostics. A number of metabolites have been reported in literature to be fluorescent and to change their spectra according to their biochemical configurations. For example, the measurement of NADH in its free and bound state is possible thanks to a shift in the emission spectra when NADH is bound to enzymes such as Lactate Dehydrogenase (LDH). Likewise, retinol and retinoic are known to have different autofluorescent spectra. A map of the phasor position for common autofluorescence from pure solutions is reported in FIG. 27B. Imaging autofluorescent data, with regard to cell metabolism, requires accounting for complex and dynamic changes of metabolic pathways which can occur in a broad range of times, from seconds to years. These autofluorescent signals are often weak in nature and do not rapidly replenish after photobleaching. Laser power may be reduced to avoid rapid autofluorescence spectral signal bleaching, as well to reduce photo-damage. Additional factors known to affect emission spectra include pH and temperature, pixel-wise concentration of the fluorophore, excitation power, developmental stage and region of the sample imaged. An example for the latter is reported in FIG. 18, where signals in the sample present strong localized differences. One example of the effects of different 2-photon excitation power and different levels of pixel-wise concentration is reported in FIGS. 5-6. In these images, samples at similar developmental stages are imaged utilizing different pixel size (0.259 μm and 0.923 μm lateral resolutions) and laser power (4% and 3% @740 nm 2-photon) resulting in laser power densities of ~$4.7\cdot10^{-6}$ mW/mm$^2$. This different laser power causes some lower-concentration intrinsic fluorophores to not be excited, in this case mRuby is visible in FIG. 5 but not in FIG. 6. In both of these images, FAD is not excited in measurable quantity, whereas in FIG. 28, where the laser power density is $1.4\cdot10^{-3}$ mW/mm$^2$, FAD contribution is measurable and unmixed. HyU is well posed for the analysis of intrinsically low autofluorescence owing to its ability to operate at low SNR. FIG. 18, illustrates unmixing of multiple autofluorescent signals based on spectra acquired from in vitro solutions. FIG. 23, 25 present a simulated overview of the improvement of HyU over Linear Unmixing for autofluorescence data, as a function of number of labels, percentage of pixels containing mixed ratio of fluorophores, number of denoising filters applied and number of channels under different levels of Signal to Noise.

Example 24. Reduced Computational Costs During Unmixing

An advantage of HyU is speed. HyU provides substantial speed boosts when comparing to other pixel-based unmixing algorithms. The exception is for the conventional LU vs HyU owing to the highly optimized computational implementation of the functions which are utilized in the conventional LU. This speed boost occurs because unmixing is performed at a phasor-histogram level, where a single bin corresponds to a multitude of image pixels. For algorithms other than standard LU, HyU provides up to ~500-fold improvement in speed at comparable coding language and computing hardware, processing 2 GB in less than 100 seconds (FIG. 19).

This improvement provides a solution for open image-analysis challenges in multiplexing fluorescence. First, the increased size of HFI data, resulting from continuously higher throughput and resolution microscopes, scaled with the number of spectral channels. Second, the number of datasets, owing to experimental reproducibility and biological variability.

Example 25. Improvements of HyU Over the Standard Phasor Analysis

Linearity of combinations is the general assumption for most of the spectral analysis algorithms in Hyperspectral Fluorescence Imaging (HFI). Each pixel is assumed to contain a linear combination of the independent spectral signatures, or endmembers, contained in the sample. This assumption requires knowledge, or identification, of the independent spectra within the sample. In standard linear unmixing algorithms, the extraction of relative amounts of spectra (ratios) is conducted on a pixel-by-pixel basis, at the expense of computational costs. Disrupted experimental signals, in the case of lower Signal to Noise Ratio (SNR) spectra, complicate the detection of spectral endmembers and reduce the accuracy of ratio determination. These standard unmixing algorithms, however, have the advantage of being unsupervised with the possibility of automating the analysis process.

Figure 31:
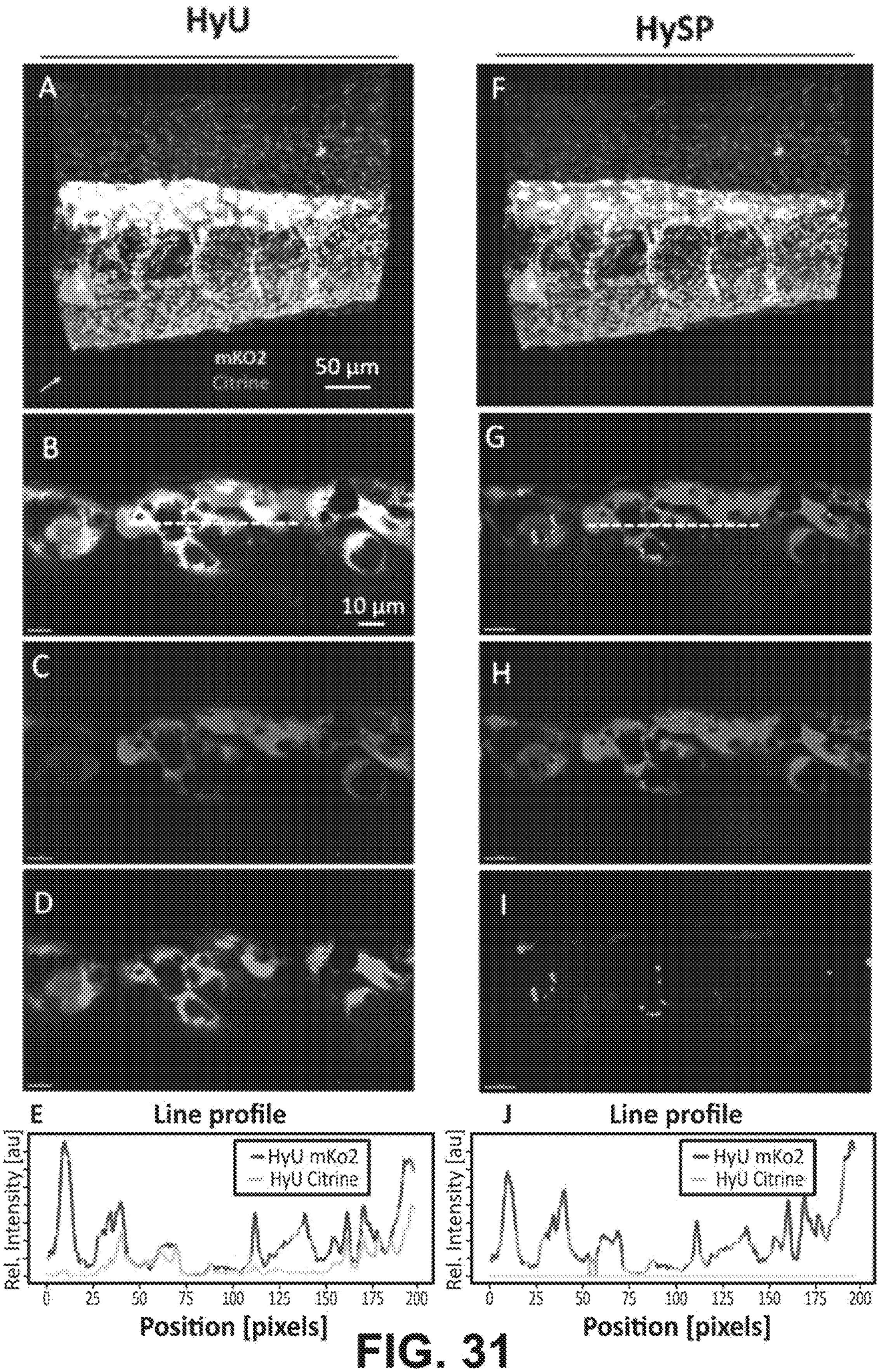
FIG. 31 illustrates an example comparison of HyU vs. HySP results from a spectrally overlapping and spatially non-disperse sample. Results for unmixing using HyU and HySP on a spectrally overlapping and spatially non-disperse dataset collected from a 5 dpf dual-labeled transgenic zebrafish embryo: Gt(cltca-citrine);Tg(fli1:mKO2), presenting frequent combinations of signals in pixels across the dataset. (A-E) HyU unmixing results and (F-K) HySP unmixing results for the dataset. (A,F) Volumetric images show the expected signal overlaps between channels for the HyU result and a more distinct separation in the HySP result. This is further demonstrated for the results in a (B,G) single z-slice, for just the (C,H) mKO2 channel, and the (D,I) Citrine channel. (E,J) Line profiles for the lines shown in B and G, respectively, demonstrate the fractional nature of HyU results compared to the winner-takes-all analysis of HySP.

The phasor approach has become a popular dimensionality reduction approach for the analysis of both fluorescence lifetime and spectral image analysis. Phasors provide key advantages, including spectral compression, denoising, and computational reduction for both pre-processing[3] and unmixing of HFI datasets. Phasor analysis overcomes the challenge of low SNR data analysis that limits standard unmixing algorithms, providing a multiplexing solution to a need. The phasor transform is a lossy encoder that in principle carries a reduced percentage of the information compared to the original clean data. In the imaging of fluorescent signals, where signal to noise often decreases to lower digits, the encoding loss is less relevant compared to the noise of the fluorescent signals. This fundamental advantage of increasing SNR in noisy data has made the phasor method a valuable tool for fluorescence microscopy, both for Lifetime and Spectral Fluorescence Microscopy. This point is reported by multiple groups using phasors and, more recently, nicely described in the work of Scipioni et al. Standard Phasor analysis is fully supervised and requires a manual selection of regions or points on a graphical representation of the transformed spectra, called the phasor plot. Each selection of a region in the phasor plot associates pixels containing similar spectra to the same fluorophore, forming an output channel that contains wavelength integral of intensities with unitary ratiometric value. This "winner takes all" approach is suitable when fluorophores for each single excitation light are spectrally overlapping and spatially disperse (FIG. 30), but requires separate acquisition of different excitation wavelengths for demultiplexing spatially and spectrally overlapping fluorophores (FIG. 31).

HyU uses the phasor transform to group pixels with similar spectral shape within each phasor histogram bin.

This approach maintains the advantage of compressing, denoising and simplifying identification of clean endmember fluorescent spectra. However, HyU improves on the robustness of the analysis. The denoised signals are maintained in a hybrid phasor and wavelength domain, and therefore can be unmixed with a multitude of standard unmixing algorithms (FIG. 19), such as Linear Unmixing or Fully Constrained Least Squares. These standard unmixing approaches can operate without supervision and provide for each pixel the ratios for a set of spectral signals, overcoming some of the limitations of phasor, but generally do not perform well in experimental conditions with reduced and compromised signals, such as in fluorescence, and require extensive computational time for high spectral-count datasets. HyU provides wavelength-based denoised spectra that enable these standard algorithms to outperform their pixel-by-pixel typical application in quality of the results (FIGS. 22-25), owing to cleaner and better defined fluorescent spectra in each phasor bin, and, generally, in speed, owing to the phasor dimensionality reduction. HyU performs well for single excitation light when fluorophores are spectrally overlapping both when they are spatially disperse or co-localized, providing a ratio for each independent spectrum currently unmixed. HyU may have reasonable performance for up to 8 different fluorophores per dataset, for each single excitation wavelength. In an experiment with a carefully chosen palette of labels, where octuples of fluorophores can be excited by a single wavelength, with an instrument capable of spectral acquisition with 5 standard and sufficiently spectrally separated excitation wavelengths in 5 sequential acquisitions (one for each excitation light), HyU could, in principle, unmix 40 signals. This performance however decreases with the number of channels (FIGS. 24-25) showing a small deterioration at 8 channels and limitations at 4.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed herein. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and implementations have been disclosed herein, other aspects and implementations will be apparent to those skilled in the art. The various aspects and implementations disclosed herein are for purposes of illustration and are not intended to be limiting.

All references cited herein, including but not limited to published and unpublished applications, patents, and literature references, are incorporated herein by reference for the subject matter referenced, and in their entirety and are hereby made a part of this specification. To the extent publications and patents or patent applications incorporated by reference contradict the disclosure contained in the specification, the specification is intended to supersede and/or take precedence over any such contradictory material.

In this disclosure, the indefinite article "a" and phrases "one or more" and "at least one" are synonymous and mean "at least one".

Relational terms such as "first" and "second" and the like may be used solely to distinguish one entity or action from another, without necessarily requiring or implying any actual relationship or order between them. The terms "comprises," "comprising," and any other variation thereof when used in connection with a list of elements in the specification or claims are intended to indicate that the list is not exclusive and that other elements may be included. Similarly, an element preceded by an "a" or an "an" does not, without further constraints, preclude the existence of additional elements of the identical type.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

The phrase "means for" when used in a claim is intended to and should be interpreted to embrace the corresponding structures and materials that have been described and their equivalents. Similarly, the phrase "step for" when used in a claim is intended to and should be interpreted to embrace the corresponding acts that have been described and their equivalents. The absence of these phrases from a claim means that the claim is not intended to and should not be interpreted to be limited to these corresponding structures, materials, or acts, or to their equivalents.

In at least some of the previously described implementations, one or more elements used in an implementation can interchangeably be used in another implementation unless such a replacement is not technically feasible. It will be appreciated by those skilled in the art that various other omissions, additions and modifications may be made to the methods and structures described herein without departing from the scope of the claimed subject matter. All such modifications and changes are intended to fall within the scope of the disclosed subject matter.

The scope of protection is limited solely by the claims that now follow. That scope is intended and should be interpreted to be as broad as is consistent with the ordinary meaning of the language that is used in the claims when interpreted in light of this specification and the prosecution history that follows, except where specific meanings have been set forth, and to encompass all structural and functional equivalents.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to implementations containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

None of the claims are intended to embrace subject matter that fails to satisfy the requirement of Sections 101, 102, or 103 of the Patent Act, nor should they be interpreted in such a way. Any unintended coverage of such subject matter is hereby disclaimed. Except as just stated in this paragraph, nothing that has been stated or illustrated is intended or should be interpreted to cause a dedication of any component, step, feature, object, benefit, advantage, or equivalent to the public, regardless of whether it is or is not recited in the claims.

The abstract is provided to help the reader quickly ascertain the nature of the technical disclosure. It is submitted with the understanding that it will not be used to interpret or limit the scope or meaning of the claims. In addition, various features in the foregoing detailed description are grouped together in various implementations to streamline the disclosure. This method of disclosure should not be interpreted as requiring claimed implementations to require more features than are expressly recited in each claim. Rather, as the following claims reflect, inventive subject matter lies in less than all features of a single disclosed implementation. Thus, the following claims are hereby incorporated into the detailed description, with each claim standing on its own as separately claimed subject matter.

We claim:

1. A hyperspectral imaging system for generating a representative image of a target, which is configured to use a hybrid unmixing technique (HyU), comprising:

an image forming system;

wherein the image forming system has a configuration that:

acquires a detected radiation of the target, wherein the detected radiation comprises at least two target waves, each target wave having a detected intensity and a different detected wavelength;

forms a target image using the detected target radiation, wherein the target image comprises at least two image pixels, and wherein each image pixel corresponds to one physical point on the target;

forms at least one intensity spectrum for each image pixel using the detected intensity and the detected wavelength of each target wave;

transforms the intensity spectrum of each image pixel using a Fourier transform into a complex-valued function based on the intensity spectrum of each image pixel, wherein each complex-valued function has at least one real component and at least one imaginary component;

forms one phasor point on a phasor plane for each image pixel by plotting a value of the real component against a value of the imaginary component, wherein the value of the real component is referred to as the real value hereafter, and wherein the value of the imaginary component is referred to as the imaginary value hereafter;

forms a phasor histogram comprising at least two phasor bins, wherein each phasor bin comprises at least one phasor point;

aggregates the detected spectra belonging to the image pixels of each phasor bin;

generates a representative intensity spectrum for each phasor bin;

unmixes representative intensity spectra of the phasor bins by using an unmixing technique, thereby determining an abundance of each spectral endmember of the detected radiation;

determines an abundance of each spectral endmember in the representative intensity spectra and the detected intensity belonging to the image pixel; and generates a representative intensity image of the target representing the abundance of each spectral endmember.

2. The hyperspectral imaging system of claim 1, wherein the hyperspectral imaging system further comprises an optics system; wherein:

the optics system comprises at least one optical component;

wherein the at least one optical component comprises at least one optical detector;

wherein the at least one optical detector has a configuration that:

detects electromagnetic radiation absorbed, transmitted, refracted, reflected, and/or emitted from at least one physical point on the target, thereby forming the target radiation; wherein the target radiation comprises at least two target waves, each target wave having an intensity and a different wavelength; and detects the intensity and the wavelength of each target wave; and transmits the detected target radiation, and each target wave's detected intensity and detected wavelength to the image forming system to be acquired.

3. The hyperspectral imaging system of claim 1, wherein the image forming system further comprises a control system, a hardware processor, a memory, and a display; wherein the image forming system has a further configuration that displays the representative image of the target on the image forming system's display.

4. The hyperspectral imaging system of claim 1, wherein the unmixing technique is a linear unmixing technique.

5. The hyperspectral imaging system of claim 1, wherein the unmixing technique is a fully constrained least squares unmixing technique, a matrix inversion unmixing technique, non-negative matrix factorization unmixing technique, geometric unmixing technique, Bayesian unmixing technique, sparse unmixing technique, or any combination thereof.

6. The hyperspectral imaging system of claim 1, wherein the image forming system has a further configuration that applies a denoising filter to reduce a Poisson noise and/or instrumental noise of the detected radiation.

7. The hyperspectral imaging system of claim 1, wherein the image forming system has a further configuration that applies a denoising filter on the real component and/or the imaginary component of each complex-valued function at least once so as to produce a denoised real value and a denoised imaginary value for each image pixel.

8. The hyperspectral imaging system of claim 1, wherein the image forming system has a further configuration that:

applies a denoising filter on the real component and/or the imaginary component of each complex-valued function at least once so as to produce a denoised real value and a denoised imaginary value for each image pixel; wherein the denoising filter is applied:

after the image forming system transforms the formed intensity spectrum belonging to each image pixel using the Fourier transform into the complex-valued function; and/or before the image forming system forms one phasor point on the phasor plane for each image pixel; and uses the denoised real value as the real value for each image pixel and the denoised imaginary value for each image pixel as the imaginary value to form one phasor point on the phasor plane for each image pixel.

9. The hyperspectral imaging system of claim 1, wherein the image forming system has a further configuration that applies a denoising filter to the value of the real component and/or the value of the imaginary component after the image forming system forms one phasor point on the phasor plane for each image pixel.

10. The hyperspectral imaging system of claim 1, wherein the image forming system has a further configuration that aggregates the detected spectra belonging to the image pixels of each phasor bin; and wherein the detected spectra belonging to the same phasor bin have essentially similar spectral shape or substantially same spectral shape.

11. The hyperspectral imaging system of claim 1, wherein:

the image forming system has a further configuration that aggregates the detected spectra belonging to the image pixels of each phasor bin;

each detected spectrum belonging to the image pixels of the same bin have at least two detected intensities and a detected wavelength for each detected intensity; and wherein the relative detected intensity values of each spectrum belonging to the same spectral bin are substantially same to those of the other spectra aggregated in the same bin.

12. The hyperspectral imaging system of claim 1, wherein the image forming system has a further configuration that:

forms at least two phasor bins by discretizing a phasor plot along its real dimension and its imaginary dimension, wherein each phasor bin has a phasor bin area on each phasor plot; and aggregates the detected spectra belonging to the image pixels of each phasor bin.

13. The hyperspectral imaging system of claim 1, wherein the image forming system has a further configuration that:

forms at least four phasor bins by discretizing a phasor plot along its real dimension and its imaginary dimension, wherein each phasor bin has a phasor bin area on each phasor plot, wherein the phasor bin area is 4/(total number of phasor bins), and wherein the total number of phasor bins is a product of number of discretizations along real dimension of the phasor plot and number of discretizations along imaginary dimension of the phasor plot; and aggregates the detected spectra belonging to the image pixels of each phasor bin.

14. The hyperspectral imaging system of claim 1, wherein the image forming system uses at least one harmonic of the Fourier transform to generate the representative image of the target.

15. The hyperspectral imaging system of claim 1, wherein the image forming system uses at least a first harmonic and/or a second harmonic of the Fourier transform to generate the representative image of the target.

16. The hyperspectral imaging system of claim 1, wherein the image forming system uses only a first harmonic or only a second harmonic of the Fourier transform to generate the representative image of the target.

17. The hyperspectral imaging system of claim 1, wherein the image forming system uses only a first harmonic and only a second harmonic of the Fourier transform to generate the representative image of the target.

18. The hyperspectral imaging system of claim 1, wherein the at least one optical component further comprises at least one illumination source to illuminate the target, wherein the illumination source generates an illumination source radiation that comprises at least one illumination wave.

19. The hyperspectral imaging system of claim 1, wherein the detected target radiation is a fluorescence radiation.

20. A method for generating a representative image of a target, the method comprising:

forming at least one intensity spectrum for image pixels of a target image, wherein the target image is based on a detected radiation;

implementing a hyperspectral phasor system configured to:

form one phasor point on a phasor plane for each image pixel;

form a phasor histogram comprising at least two phasor bins, wherein each phasor bin comprises at least one phasor point;

aggregate the detected spectra of the image pixels of the at least two phasor bins; and generate at least one representative intensity spectrum for the at least two phasor bins;

implementing an unmixing system configured to:

unmix the at least one representative intensity spectrum of the at least two phasor bins using one or more unmixing techniques; and generating a representative intensity image of the target based on at least the representative intensity spectra and a detected intensity corresponding to the detected radiation.

* * * * *